US009101160B2

(12) United States Patent
Prakash et al.

(10) Patent No.: US 9,101,160 B2
(45) Date of Patent: *Aug. 11, 2015

(54) CONDIMENTS WITH HIGH-POTENCY SWEETENER

(75) Inventors: Indra Prakash, Alpharetta, GA (US); Grant E. DuBois, Roswell, GA (US)

(73) Assignee: The Coca-Cola Company, Atlanta, GA (US)

(*) Notice: Subject to any disclaimer, the term of this patent is extended or adjusted under 35 U.S.C. 154(b) by 916 days.

This patent is subject to a terminal disclaimer.

(21) Appl. No.: 11/556,062

(22) Filed: Nov. 2, 2006

(65) Prior Publication Data

US 2007/0116834 A1 May 24, 2007

Related U.S. Application Data

(60) Provisional application No. 60/739,302, filed on Nov. 23, 2005, provisional application No. 60/739,124, filed on Nov. 23, 2005, provisional application No. 60/805,216, filed on Jun. 19, 2006, provisional application No. 60/805,209, filed on Jun. 19, 2006.

(51) Int. Cl.
*A23L 1/236* (2006.01)
*A23D 7/00* (2006.01)
*A23D 9/00* (2006.01)
*A23L 1/24* (2006.01)

(52) U.S. Cl.
CPC . *A23L 1/236* (2013.01); *A23D 7/00* (2013.01); *A23D 9/00* (2013.01); *A23L 1/24* (2013.01); *A23L 1/243* (2013.01)

(58) Field of Classification Search
CPC ........... A23L 1/236; A23L 1/24; A23L 1/243; A23D 7/00; A23D 9/00
USPC .................................. 426/548, 589, 615, 638
See application file for complete search history.

(56) References Cited

U.S. PATENT DOCUMENTS

| 3,320,074 A | 5/1967 | Gebhardt |
| 3,489,572 A | 1/1970 | Kracauer |
| 3,608,069 A | 9/1971 | Fuller |
| 3,615,597 A | 10/1971 | Durst et al. |
| 3,615,700 A | 10/1971 | Kornfeld |
| 3,625,711 A | 12/1971 | Eisenstadt |
| 3,647,482 A | 3/1972 | Yueh |
| 3,647,483 A | 3/1972 | Eisenstadt |
| 3,656,973 A | 4/1972 | Paterson et al. |
| 3,699,132 A | 10/1972 | Acton et al. |
| 3,717,477 A | 2/1973 | Nonomiya et al. |
| 3,725,453 A | 4/1973 | Lapidus et al. |
| 3,751,270 A | 8/1973 | Rizzi |
| 3,773,526 A | 11/1973 | Bliznak |
| 3,875,311 A | 4/1975 | Eisenstadt |
| 3,875,312 A | 4/1975 | Eisenstadt |
| 3,886,295 A | 5/1975 | Burke et al. |
| 3,899,592 A | 8/1975 | Suarez et al. |
| 3,901,978 A | 8/1975 | Nelson et al. |
| 3,908,026 A | 9/1975 | Neely et al. |
| 3,908,028 A | 9/1975 | Neely et al. |
| 3,920,815 A | 11/1975 | Harvey et al. |
| 3,922,369 A | 11/1975 | Glicksman et al. |
| 3,934,047 A | 1/1976 | Schade |
| 3,934,048 A | 1/1976 | Furda |
| 3,946,121 A | 3/1976 | Eisenstadt |
| 3,966,993 A | 6/1976 | Luck |
| 3,971,857 A | 7/1976 | Fruda |
| 3,972,860 A | 8/1976 | Moriarty et al. |
| 3,974,299 A | 8/1976 | Crosby et al. |
| 3,976,790 A | 8/1976 | Crosby et al. |
| 3,978,034 A | 8/1976 | Sheehan et al. |
| 3,985,913 A | 10/1976 | Johnson et al. |
| 4,001,456 A | 1/1977 | Glicksman |
| 4,007,288 A | 2/1977 | Glicksman et al. |
| 4,009,292 A | 2/1977 | Finucane |
| 4,022,924 A | 5/1977 | Mitchell et al. |
| 4,045,581 A | 8/1977 | Mackay et al. |

(Continued)

FOREIGN PATENT DOCUMENTS

| AU | 612738 | 6/1989 |
| AU | 5654000 A | 3/2001 |

(Continued)

OTHER PUBLICATIONS

Geuns, Jan M.C., "Review: The safety of stevioside used as a sweetener", in Proceedings of the first symposium 'The Safety of Stevioside', p. 85-127 (2004).*
Couzy, Francois, "International Search Report and Written Opinion of the International Searching Authority," Aug. 31, 2007, PCT/US2006/044576, European Patent Office, Rijswijk, The Netherlands.
Heirbaut, Marc, "International Search Report and Written Opinion of the International Searching Authority," Jan. 2, 2008, PCT/US2006/044725, European Patent Office, Rijswijk, The Netherlands.
Heirbaut, Marc, "International Search Report and Written Opinion of the International Searching Authority," Jan. 2, 2008, PCT/US2006/044797, European Patent Office, Rijswijk, The Netherlands.
Tatadhani, M. and Subhash, R., "Preliminary studies on *Stevia rebaudiana* leaves: proximal composition, mineral analysis and phytochemical screening," J. Med. Sci. 6(3): 321-326 (2006).
Parpinello, G. P. et al., "Stevioside as a replacement of sucrose in peach juice: sensory evaluation", *Journal of Sensory Studies* 2001, vol. 16, pp. 471-484.

(Continued)

*Primary Examiner* — Leslie Wong
(74) *Attorney, Agent, or Firm* — King & Spalding

(57) ABSTRACT

The present invention relates generally to condiment compositions comprising non-caloric or low-caloric high-potency sweeteners and methods for making and using them. In particular, the present invention relates to different condiment compositions comprising at least one non-caloric or low-caloric natural and/or synthetic high potency sweetener, at least one sweet taste improving composition, and a condiment base. The present invention also relates to condiment compositions and methods that can improve the tastes of non-caloric or low-caloric natural and/or synthetic, high-potency sweeteners by imparting a more sugar-like taste or characteristic. In particular, the condiment compositions and methods provide a more sugar-like temporal profile, including sweetness onset and sweetness linger, and/or a more sugar-like flavor profile.

6 Claims, 5 Drawing Sheets

(56) References Cited

U.S. PATENT DOCUMENTS

| | | | |
|---|---|---|---|
| 4,051,268 A | 9/1977 | Shires et al. |
| 4,064,274 A | 12/1977 | Mackay et al. |
| 4,065,579 A | 12/1977 | Mackay et al. |
| 4,082,858 A | 4/1978 | Morita et al. |
| 4,084,010 A | 4/1978 | Takemoto et al. |
| 4,085,227 A | 4/1978 | Mackay et al. |
| 4,085,232 A | 4/1978 | Eisenstadt |
| 4,093,752 A | 6/1978 | Withycombe et al. |
| 4,096,285 A | 6/1978 | Burge et al. |
| 4,103,036 A | 7/1978 | Sprecker et al. |
| 4,117,015 A | 9/1978 | Hall et al. |
| 4,119,738 A | 10/1978 | Wagner et al. |
| 4,122,120 A | 10/1978 | Sprecker et al. |
| 4,122,205 A | 10/1978 | Burge et al. |
| 4,146,650 A | 3/1979 | Dick, Jr. et al. |
| 4,154,862 A | 5/1979 | Gentili et al. |
| 4,158,068 A | 6/1979 | Luck et al. |
| 4,176,201 A | 11/1979 | Cook |
| 4,204,007 A | 5/1980 | Wang et al. |
| 4,219,571 A | 8/1980 | Miyake |
| 4,228,198 A | 10/1980 | Burge et al. |
| 4,235,942 A | 11/1980 | Heller et al. |
| 4,254,154 A | 3/1981 | Eisenstadt |
| 4,254,155 A | 3/1981 | Dwivedi et al. |
| 4,256,641 A | 3/1981 | Batcho et al. |
| 4,262,032 A | 4/1981 | Levin |
| 4,277,511 A | 7/1981 | Bliznak et al. |
| 4,283,434 A | 8/1981 | Dubois et al. |
| 4,290,957 A | 9/1981 | DuBois et al. |
| 4,292,336 A | 9/1981 | Latymer |
| 4,304,794 A | 12/1981 | Dwivedi et al. |
| 4,316,847 A | 2/1982 | Batcho et al. |
| 4,332,830 A | 6/1982 | Dubois |
| 4,338,346 A | 7/1982 | Brand |
| 4,348,333 A | 9/1982 | DuBois |
| 4,348,416 A | 9/1982 | Boden |
| 4,353,889 A | 10/1982 | Dubois |
| 4,361,697 A | 11/1982 | Dobberstein et al. |
| 4,381,402 A | 4/1983 | Dubois |
| 4,394,399 A | 7/1983 | Keyser et al. |
| 4,399,162 A | 8/1983 | Okada |
| 4,399,163 A | 8/1983 | Brennan et al. |
| 4,402,990 A | 9/1983 | Dubois |
| 4,404,367 A | 9/1983 | Stephenson et al. |
| T104004 I4 | 3/1984 | Lipinski |
| 4,439,460 A | 3/1984 | Tsau et al. |
| 4,440,855 A | 4/1984 | Horwath et al. |
| 4,454,290 A | 6/1984 | Dubois |
| 4,454,328 A | 6/1984 | Brennan et al. |
| 4,467,033 A | 8/1984 | Horwath et al. |
| 4,492,755 A | 1/1985 | Horwath et al. |
| 4,495,170 A | 1/1985 | Beyts et al. |
| 4,497,835 A | 2/1985 | Winston |
| 4,517,379 A | 5/1985 | Brennan et al. |
| RE31,954 E | 7/1985 | Fine et al. |
| 4,528,205 A | 7/1985 | Turrisi |
| 4,536,396 A | 8/1985 | Stephens, Jr. et al. |
| 4,537,763 A | 8/1985 | Miyake et al. |
| 4,544,565 A | 10/1985 | Barnett |
| 4,544,566 A | 10/1985 | Barnett et al. |
| 4,545,999 A | 10/1985 | Riemer et al. |
| 4,546,000 A | 10/1985 | Zanno et al. |
| 4,547,377 A | 10/1985 | Ogawa et al. |
| 4,547,584 A | 10/1985 | Riemer et al. |
| 4,551,342 A | 11/1985 | Nakel et al. |
| 4,556,565 A | 12/1985 | Arima et al. |
| 4,557,927 A | 12/1985 | Miyake et al. |
| 4,564,528 A | 1/1986 | Seltzman et al. |
| 4,571,308 A | 2/1986 | Zanno et al. |
| 4,571,345 A | 2/1986 | Verlander et al. |
| 4,572,799 A | 2/1986 | Zanno et al. |
| 4,574,091 A | 3/1986 | Steensen et al. |
| 4,579,748 A | 4/1986 | Riemer et al. |
| 4,590,160 A | 5/1986 | Nishihashi et al. |
| 4,599,403 A | 7/1986 | Kumar |
| 4,602,095 A | 7/1986 | Zanno et al. |
| 4,603,011 A | 7/1986 | Roy et al. |
| 4,603,012 A | 7/1986 | Zanno et al. |
| 4,612,202 A | 9/1986 | Engel et al. |
| 4,612,942 A | 9/1986 | Dobberstein et al. |
| 4,613,512 A | 9/1986 | Barnett et al. |
| 4,619,782 A | 10/1986 | Zanno et al. |
| 4,619,833 A | 10/1986 | Anderson |
| 4,619,834 A | 10/1986 | Zanno et al. |
| 4,622,232 A | 11/1986 | Zanno et al. |
| 4,622,233 A | 11/1986 | Torres |
| 4,622,417 A | 11/1986 | Barnett et al. |
| 4,622,418 A | 11/1986 | Barnett et al. |
| 4,623,543 A | 11/1986 | Motegi et al. |
| 4,626,441 A | 12/1986 | Wokstein |
| 4,626,442 A | 12/1986 | Zanno et al. |
| 4,627,987 A | 12/1986 | Barnett et al. |
| 4,631,195 A | 12/1986 | Colliopoulos |
| 4,633,006 A | 12/1986 | Barnett et al. |
| 4,634,792 A | 1/1987 | Zanno et al. |
| 4,636,396 A | 1/1987 | Zanno et al. |
| 4,638,071 A | 1/1987 | Barnett et al. |
| 4,642,240 A | 2/1987 | Barnett et al. |
| 4,645,678 A | 2/1987 | Nofre et al. |
| 4,650,688 A | 3/1987 | Roy et al. |
| 4,652,457 A | 3/1987 | Zanno et al. |
| 4,652,676 A | 3/1987 | Zanno et al. |
| 4,654,219 A | 3/1987 | Barnett et al. |
| 4,654,439 A | 3/1987 | Roy et al. |
| 4,664,929 A | 5/1987 | Barnett et al. |
| 4,666,129 A | 5/1987 | Dobson |
| 4,666,729 A | 5/1987 | Roy et al. |
| 4,676,989 A | 6/1987 | Barnett et al. |
| 4,677,126 A | 6/1987 | Janusz et al. |
| 4,678,674 A | 7/1987 | Zanno et al. |
| 4,678,675 A | 7/1987 | Zanno et al. |
| 4,684,666 A | 8/1987 | Haas |
| 4,690,827 A | 9/1987 | Kupper et al. |
| 4,692,512 A | 9/1987 | Janusz |
| 4,692,513 A | 9/1987 | Blum et al. |
| 4,698,231 A | 10/1987 | Barnett et al. |
| 4,701,552 A | 10/1987 | Zanno et al. |
| 4,714,619 A | 12/1987 | Seltzman et al. |
| 4,722,844 A | 2/1988 | Ozawa et al. |
| 4,731,246 A | 3/1988 | Chavkin et al. |
| 4,737,375 A | 4/1988 | Nakel et al. |
| 4,738,854 A | 4/1988 | Friello et al. |
| 4,738,856 A | 4/1988 | Clark |
| 4,741,910 A | 5/1988 | Karwowski et al. |
| 4,752,485 A | 6/1988 | Sharma et al. |
| 4,758,438 A | 7/1988 | Stroz et al. |
| 4,758,443 A | 7/1988 | Roy et al. |
| 4,760,175 A | 7/1988 | Zanno et al. |
| 4,766,246 A | 8/1988 | Zanno et al. |
| 4,770,889 A | 9/1988 | Sakai et al. |
| 4,772,482 A | 9/1988 | Olinger et al. |
| 4,781,927 A | 11/1988 | Zanno et al. |
| 4,786,722 A | 11/1988 | Zehner |
| 4,788,073 A | 11/1988 | Zanno et al. |
| 4,788,332 A | 11/1988 | Zanno et al. |
| 4,797,298 A | 1/1989 | Brennan et al. |
| 4,803,082 A | 2/1989 | Cherukuri et al. |
| 4,804,548 A | 2/1989 | Sharma et al. |
| 4,804,782 A | 2/1989 | Brennan et al. |
| 4,814,172 A | 3/1989 | Chavkin et al. |
| 4,820,528 A | 4/1989 | Stroz et al. |
| 4,822,635 A | 4/1989 | Zanno et al. |
| 4,826,824 A | 5/1989 | Schiffman |
| 4,828,857 A | 5/1989 | Sharma et al. |
| 4,830,853 A | 5/1989 | Murthy et al. |
| 4,839,184 A | 6/1989 | Cherukuri et al. |
| 4,849,238 A | 7/1989 | Wakabayashi et al. |
| 4,851,221 A | 7/1989 | Park et al. |
| 4,855,454 A | 8/1989 | Brennan et al. |
| 4,863,752 A | 9/1989 | Beyts |
| 4,870,190 A | 9/1989 | Brennan et al. |
| 4,871,570 A | 10/1989 | Barnett et al. |
| 4,873,112 A | 10/1989 | Mitchell et al. |
| 4,877,895 A | 10/1989 | Nofrem et al. |

(56) References Cited

U.S. PATENT DOCUMENTS

| | | |
|---|---|---|
| 4,882,157 A | 11/1989 | Yang et al. |
| 4,882,159 A | 11/1989 | Yang et al. |
| 4,883,685 A | 11/1989 | Kondou |
| 4,883,888 A | 11/1989 | Gardlik |
| 4,894,464 A | 1/1990 | Brennan et al. |
| 4,902,525 A | 2/1990 | Kondou |
| 4,915,969 A | 4/1990 | Beyts |
| 4,917,913 A | 4/1990 | Buckholz et al. |
| 4,921,939 A | 5/1990 | Nofre et al. |
| 4,927,646 A | 5/1990 | Jenner et al. |
| 4,931,293 A | 6/1990 | Cherukuri et al. |
| 4,933,190 A | 6/1990 | Cherukuri et al. |
| 4,946,988 A | 8/1990 | Hill et al. |
| 4,956,191 A | 9/1990 | Ueda et al. |
| 4,959,225 A | 9/1990 | Cherukuri et al. |
| 4,960,603 A | 10/1990 | Buckholz et al. |
| 4,963,382 A | 10/1990 | Arena et al. |
| 4,966,783 A | 10/1990 | Buckholz et al. |
| 4,966,845 A | 10/1990 | Stack |
| 4,973,486 A | 11/1990 | Matsumoto et al. |
| 4,981,698 A | 1/1991 | Cherukuri et al. |
| 4,986,994 A | 1/1991 | Baccus |
| 4,988,527 A | 1/1991 | Buckholz et al. |
| 4,988,532 A | 1/1991 | Buckholz et al. |
| 4,990,354 A | 2/1991 | Bakal et al. |
| 4,992,279 A | 2/1991 | Palmer et al. |
| 4,997,667 A | 3/1991 | Nofre et al. |
| 4,999,207 A | 3/1991 | Buckholz et al. |
| 5,000,965 A | 3/1991 | Killeen et al. |
| 5,004,595 A | 4/1991 | Cherukuri et al. |
| 5,013,716 A | 5/1991 | Cherukuri et al. |
| 5,017,400 A | 5/1991 | Olinger et al. |
| 5,023,329 A | 6/1991 | Neiditch et al. |
| 5,034,214 A | 7/1991 | Palmer et al. |
| 5,043,169 A | 8/1991 | Cherukuri et al. |
| 5,043,181 A | 8/1991 | Chiang |
| 5,049,402 A | 9/1991 | Tamaki et al. |
| RE33,719 E | 10/1991 | Levin |
| 5,057,328 A | 10/1991 | Cherukuri et al. |
| 5,059,416 A | 10/1991 | Cherukuri et al. |
| 5,059,428 A | 10/1991 | Wong et al. |
| 5,061,320 A | 10/1991 | Goodacre et al. |
| 5,061,496 A | 10/1991 | Cherukuri et al. |
| 5,064,658 A | 11/1991 | Cherukuri et al. |
| 5,069,924 A | 12/1991 | Baccus, Jr. |
| 5,077,073 A | 12/1991 | Ennis et al. |
| 5,080,910 A | 1/1992 | Cherukuri et al. |
| 5,080,916 A | 1/1992 | Kondou |
| 5,087,460 A | 2/1992 | Cherukuri et al. |
| 5,091,015 A | 2/1992 | Bunick et al. |
| 5,098,730 A | 3/1992 | Pepper et al. |
| 5,104,674 A | 4/1992 | Chen et al. |
| 5,106,632 A | 4/1992 | Wong et al. |
| 5,108,763 A | 4/1992 | Chau et al. |
| 5,110,612 A | 5/1992 | Quarles et al. |
| 5,112,610 A | 5/1992 | Kienle |
| 5,126,158 A | 6/1992 | Sharkasi |
| 5,156,866 A | 10/1992 | Sato et al. |
| 5,164,214 A | 11/1992 | Wild |
| 5,198,427 A | 3/1993 | Kinghorn et al. |
| 5,204,115 A | 4/1993 | Olinger et al. |
| 5,219,573 A | 6/1993 | Tarka, Jr. et al. |
| 5,221,624 A | 6/1993 | Blair et al. |
| 5,225,591 A | 7/1993 | Sweeny et al. |
| 5,232,735 A | 8/1993 | Kurtz et al. |
| 5,242,693 A | 9/1993 | Kurihara et al. |
| 5,246,725 A | 9/1993 | Fisher et al. |
| 5,279,849 A | 1/1994 | Fuisz et al. |
| 5,286,509 A | 2/1994 | D'Angelo et al. |
| 5,290,605 A | 3/1994 | Shapira |
| 5,298,272 A | 3/1994 | Goodman et al. |
| 5,300,309 A | 4/1994 | Foguet et al. |
| 5,310,570 A | 5/1994 | Kwapong et al. |
| 5,326,580 A | 7/1994 | Hellekant et al. |
| 5,336,513 A | 8/1994 | Riemer |
| 5,346,998 A | 9/1994 | Hellekant et al. |
| 5,358,729 A | 10/1994 | Ohkuma et al. |
| 5,364,652 A | 11/1994 | Ohkuma et al. |
| 5,366,747 A | 11/1994 | Buckholz, Jr. et al. |
| 5,368,879 A | 11/1994 | White et al. |
| 5,380,540 A | 1/1995 | Yamanaka et al. |
| 5,380,541 A | 1/1995 | Beyts et al. |
| 5,387,431 A | 2/1995 | Fuisz et al. |
| 5,411,755 A | 5/1995 | Downton et al. |
| 5,429,836 A | 7/1995 | Fuisz |
| 5,433,965 A | 7/1995 | Fischer et al. |
| 5,434,061 A | 7/1995 | Ishiguro et al. |
| 5,437,879 A | 8/1995 | Kabse et al. |
| 5,437,880 A | 8/1995 | Takaichi et al. |
| 5,445,837 A | 8/1995 | Burkes et al. |
| 5,455,049 A | 10/1995 | Anaebonam et al. |
| 5,455,235 A | 10/1995 | Takaichi et al. |
| 5,463,118 A | 10/1995 | Yuasa et al. |
| 5,464,619 A | 11/1995 | Kuznicki et al. |
| 5,468,506 A | 11/1995 | Andon |
| 5,472,716 A | 12/1995 | Kwapong et al. |
| 5,472,732 A | 12/1995 | Ohkuma et al. |
| 5,472,863 A | 12/1995 | Maruta |
| 5,473,097 A | 12/1995 | Kishimoto et al. |
| 5,480,668 A | 1/1996 | Nofre et al. |
| 5,484,593 A | 1/1996 | Iwasaki et al. |
| 5,492,715 A | 2/1996 | Greenland et al. |
| 5,498,702 A | 3/1996 | Mitchell et al. |
| 5,501,797 A | 3/1996 | Meindersma et al. |
| 5,510,123 A | 4/1996 | Mitchell et al. |
| 5,527,555 A | 6/1996 | Hellekant et al. |
| 5,527,689 A | 6/1996 | Irino et al. |
| 5,536,526 A | 7/1996 | Virtanen et al. |
| 5,543,554 A | 8/1996 | Ohura et al. |
| 5,554,400 A | 9/1996 | Stipp |
| 5,562,941 A | 10/1996 | Levy |
| 5,565,435 A | 10/1996 | Yoneyama et al. |
| 5,576,039 A | 11/1996 | Lewis |
| 5,576,042 A | 11/1996 | Fuisz |
| 5,597,608 A | 1/1997 | Fuisz |
| 5,620,707 A | 4/1997 | Sanker et al. |
| 5,626,879 A | 5/1997 | Anaebonam et al. |
| 5,629,411 A | 5/1997 | Ishiguro et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,633,006 A | 5/1997 | Catania et al. |
| 5,635,610 A | 6/1997 | Ishiguro et al. |
| 5,635,611 A | 6/1997 | Ishiguro et al. |
| 5,637,618 A | 6/1997 | Kurtz et al. |
| 5,637,754 A | 6/1997 | Rijkers et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,654,311 A | 8/1997 | Kurtz et al. |
| 5,665,755 A | 9/1997 | Kurtz et al. |
| 5,681,569 A | 10/1997 | Kuznicki et al. |
| 5,683,720 A | 11/1997 | Myers et al. |
| 5,693,485 A | 12/1997 | Harada et al. |
| 5,700,792 A | 12/1997 | Kurtz et al. |
| 5,703,053 A | 12/1997 | Kurtz et al. |
| 5,709,876 A | 1/1998 | Fuisz |
| 5,720,974 A | 2/1998 | Makino et al. |

(56) References Cited

U.S. PATENT DOCUMENTS

| | | | |
|---|---|---|---|
| 5,731,025 A | 3/1998 | Mitchell |
| 5,733,883 A | 3/1998 | Rijkers et al. |
| 5,739,409 A | 4/1998 | Fischer et al. |
| 5,741,537 A | 4/1998 | Hellekant et al. |
| 5,746,369 A | 5/1998 | McDermott |
| 5,747,300 A | 5/1998 | Nishimoto et al. |
| 5,766,622 A | 6/1998 | Nelson |
| 5,766,636 A | 6/1998 | Turk et al. |
| PP10,562 P | 8/1998 | Sys et al. |
| PP10,563 P | 8/1998 | Brandle et al. |
| PP10,564 P | 8/1998 | Marsolais et al. |
| 5,795,612 A | 8/1998 | Takemoto et al. |
| 5,827,562 A | 10/1998 | Fry et al. |
| 5,830,523 A | 11/1998 | Takaichi et al. |
| 5,843,748 A | 12/1998 | Nakada et al. |
| 5,843,758 A | 12/1998 | Russell et al. |
| 5,846,568 A | 12/1998 | Olinger et al. |
| 5,849,223 A | 12/1998 | Myers et al. |
| 5,855,948 A | 1/1999 | Mills et al. |
| 5,859,343 A | 1/1999 | Sun et al. |
| 5,866,608 A | 2/1999 | Kurtz et al. |
| 5,876,976 A | 3/1999 | Richards et al. |
| 5,879,733 A | 3/1999 | Ekanayake et al. |
| 5,902,628 A | 5/1999 | Shamil |
| 5,910,436 A | 6/1999 | Nakada et al. |
| 5,912,030 A | 6/1999 | Huzinec et al. |
| 5,916,371 A | 6/1999 | Chaen et al. |
| 5,925,378 A | 7/1999 | Carnazzo |
| 5,948,460 A | 9/1999 | Kang et al. |
| 5,955,136 A | 9/1999 | Laaman et al. |
| 5,962,678 A * | 10/1999 | Payzant et al. ............... 536/128 |
| 5,972,120 A | 10/1999 | Kutowy et al. |
| 5,973,005 A | 10/1999 | D'Amelio, Sr. et al. |
| 5,973,212 A | 10/1999 | De Sadeleer et al. |
| 5,976,602 A | 11/1999 | Baron et al. |
| 5,976,603 A | 11/1999 | Kota et al. |
| 5,993,879 A | 11/1999 | Trinnaman |
| 5,993,882 A | 11/1999 | Hanger et al. |
| 5,993,889 A | 11/1999 | Nakada et al. |
| 5,994,559 A | 11/1999 | Abushanab et al. |
| 6,007,848 A | 12/1999 | Hendrick et al. |
| 6,008,250 A | 12/1999 | Kurtz et al. |
| 6,015,792 A | 1/2000 | Kurtz et al. |
| 6,019,851 A | 2/2000 | Pittet et al. |
| 6,031,157 A | 2/2000 | Morita et al. |
| 6,037,375 A | 3/2000 | Sakamoto et al. |
| 6,045,850 A | 4/2000 | Kondou |
| 6,048,999 A | 4/2000 | Pajor et al. |
| 6,051,758 A | 4/2000 | Sun et al. |
| 6,063,428 A | 5/2000 | Ekanayake et al. |
| 6,066,345 A | 5/2000 | de Cock |
| 6,080,561 A | 6/2000 | Morita et al. |
| 6,083,549 A | 7/2000 | Harada et al. |
| 6,103,240 A | 8/2000 | Zhou |
| 6,106,883 A | 8/2000 | Sokolik et al. |
| 6,123,980 A | 9/2000 | Pearson et al. |
| 6,139,895 A | 10/2000 | Zablocki et al. |
| 6,149,941 A | 11/2000 | Schwarz et al. |
| 6,156,332 A | 12/2000 | Bakal et al. |
| 6,168,811 B1 | 1/2001 | Clark et al. |
| 6,177,064 B1 | 1/2001 | De Troostembergh et al. |
| 6,180,155 B1 | 1/2001 | Lotz et al. |
| 6,180,157 B1 | 1/2001 | Fotos et al. |
| 6,180,159 B1 | 1/2001 | Villagran et al. |
| 6,187,336 B1 | 2/2001 | Okumura et al. |
| 6,214,402 B1 | 4/2001 | Fotos et al. |
| 6,238,722 B1 | 5/2001 | Meadows |
| 6,242,029 B1 | 6/2001 | Pittet et al. |
| 6,245,373 B1 | 6/2001 | Baron et al. |
| 6,245,376 B1 | 6/2001 | Pittet et al. |
| 6,248,390 B1 | 6/2001 | Stillman |
| 6,255,557 B1 | 7/2001 | Brandle |
| 6,262,019 B1 | 7/2001 | Keller et al. |
| 6,264,999 B1 | 7/2001 | Yatka et al. |
| 6,265,012 B1 | 7/2001 | Shamil |
| 6,268,009 B1 | 7/2001 | Ekanayake et al. |
| 6,274,707 B1 | 8/2001 | Markley et al. |
| 6,287,620 B1 | 9/2001 | Van Den Ouweland et al. |
| 6,290,997 B1 | 9/2001 | Villagran et al. |
| 6,294,190 B1 | 9/2001 | Nakahara et al. |
| 6,322,806 B1 | 11/2001 | Ream et al. |
| 6,322,835 B1 | 11/2001 | De Soete et al. |
| 6,346,284 B1 | 2/2002 | Briend et al. |
| 6,358,544 B1 | 3/2002 | Henry, Jr. et al. |
| 6,365,216 B1 | 4/2002 | Dron et al. |
| 6,365,217 B2 | 4/2002 | Fotos et al. |
| 6,368,651 B1 | 4/2002 | Gerlat et al. |
| 6,379,735 B1 | 4/2002 | Yukio et al. |
| 6,383,778 B1 | 5/2002 | Zuker et al. |
| 6,399,142 B1 | 6/2002 | Silver |
| 6,407,227 B1 | 6/2002 | Nurmi et al. |
| 6,413,561 B1 | 7/2002 | Sass et al. |
| 6,419,978 B1 | 7/2002 | Silver |
| 6,423,358 B1 | 7/2002 | Barndt et al. |
| 6,432,464 B1 | 8/2002 | Andersen et al. |
| 6,432,470 B2 | 8/2002 | Chaen et al. |
| 6,458,395 B1 | 10/2002 | Emoto |
| 6,461,658 B1 | 10/2002 | Merkel et al. |
| 6,461,659 B1 | 10/2002 | Zhou |
| 6,472,000 B1 | 10/2002 | Gudas et al. |
| 6,506,434 B1 | 1/2003 | Towb et al. |
| 6,534,107 B1 | 3/2003 | Ma et al. |
| 6,540,978 B1 | 4/2003 | Margolskee et al. |
| 6,544,573 B1 | 4/2003 | Pajela et al. |
| 6,569,488 B1 | 5/2003 | Silver |
| 6,579,535 B2 | 6/2003 | Valentine et al. |
| 6,599,534 B2 | 7/2003 | Felisaz et al. |
| 6,599,553 B2 | 7/2003 | Kealey et al. |
| 6,616,955 B2 | 9/2003 | Nunes et al. |
| 6,652,891 B2 | 11/2003 | Selzer |
| 6,652,901 B2 | 11/2003 | Ishii |
| 6,673,380 B2 | 1/2004 | Yang et al. |
| 6,682,766 B2 | 1/2004 | Blumenstein-Stahl et al. |
| 6,692,577 B2 | 2/2004 | Heikkila et al. |
| 6,706,304 B1 | 3/2004 | Ishida et al. |
| 6,713,116 B1 | 3/2004 | Aldrich et al. |
| 6,723,170 B2 | 4/2004 | Ohashi et al. |
| 6,730,336 B2 | 5/2004 | Villagran et al. |
| 6,734,343 B1 | 5/2004 | Gressel et al. |
| 6,749,879 B2 | 6/2004 | Broz |
| 6,759,069 B2 | 7/2004 | Gray |
| 6,770,264 B2 | 8/2004 | Stier et al. |
| 6,773,730 B1 | 8/2004 | Liu et al. |
| 6,773,743 B1 | 8/2004 | Singer |
| 6,777,397 B2 | 8/2004 | Zehner et al. |
| 6,783,789 B2 | 8/2004 | Mutilangi et al. |
| 6,808,733 B2 | 10/2004 | Barndt et al. |
| 6,814,958 B1 * | 11/2004 | Sekimoto ..................... 424/58 |
| 6,821,547 B2 | 11/2004 | Shah et al. |
| 6,838,107 B1 | 1/2005 | Bakal et al. |
| 6,849,623 B2 | 2/2005 | Burgard |
| 6,855,359 B2 | 2/2005 | Khare |
| 6,855,360 B2 | 2/2005 | Salito et al. |
| 6,858,244 B2 | 2/2005 | Kuroda et al. |
| 6,868,366 B1 | 3/2005 | Eisenzopf |
| 6,899,911 B2 | 5/2005 | Dewis |
| 6,914,151 B1 | 7/2005 | Kawahara et al. |
| 6,924,371 B2 | 8/2005 | Karki et al. |
| 6,949,264 B1 | 9/2005 | McGrew et al. |
| 6,965,055 B2 | 11/2005 | Mori et al. |
| 6,984,732 B2 | 1/2006 | Catani et al. |
| 6,986,906 B2 | 1/2006 | Selzer et al. |
| 6,987,183 B2 | 1/2006 | Heikkila et al. |
| 6,998,144 B2 | 2/2006 | Merkel et al. |
| 6,998,480 B2 | 2/2006 | Catani et al. |
| 7,008,485 B2 | 3/2006 | Heikkila et al. |
| 7,018,667 B2 | 3/2006 | Merkel et al. |
| 7,022,239 B2 | 4/2006 | Heikkila et al. |
| 7,026,003 B2 | 4/2006 | Tomiyama et al. |
| 7,029,717 B1 | 4/2006 | Ojima et al. |
| 7,029,718 B2 | 4/2006 | Ohishi et al. |
| 7,045,166 B2 | 5/2006 | Silver |
| 7,049,435 B2 | 5/2006 | Catani et al. |
| 7,063,735 B2 | 6/2006 | Fristad et al. |

(56) References Cited

U.S. PATENT DOCUMENTS

| | | | |
|---|---|---|---|
| 7,067,150 B2 * | 6/2006 | Farber et al. ................. 424/488 |
| 7,074,453 B2 | 7/2006 | Yusuf et al. |
| 7,090,883 B2 | 8/2006 | Phipps |
| 7,101,572 B2 | 9/2006 | Santos et al. |
| 7,122,218 B2 | 10/2006 | Yamamoto et al. |
| 7,175,872 B2 | 2/2007 | Hofmann et al. |
| 7,186,431 B1 | 3/2007 | Silver |
| 7,198,804 B2 | 4/2007 | Cho et al. |
| 7,199,124 B2 | 4/2007 | Ohkawa et al. |
| 7,205,410 B2 | 4/2007 | Bosmans et al. |
| 7,208,186 B2 | 4/2007 | Norman et al. |
| 7,208,460 B2 | 4/2007 | Shefer et al. |
| 7,208,503 B2 | 4/2007 | Stokbroekx et al. |
| 7,211,422 B2 | 5/2007 | Kubota et al. |
| 7,217,817 B1 | 5/2007 | Enoki et al. |
| 7,223,416 B2 | 5/2007 | Peyman |
| 7,223,417 B2 | 5/2007 | Calton et al. |
| 7,223,570 B2 | 5/2007 | Aga et al. |
| 7,223,791 B2 | 5/2007 | Maekawa et al. |
| 7,226,625 B2 | 6/2007 | Subbiah |
| 7,226,626 B2 | 6/2007 | Yatcilla et al. |
| 7,229,641 B2 | 6/2007 | Cherukuri |
| 7,229,658 B1 | 6/2007 | Inoue et al. |
| 7,230,079 B2 | 6/2007 | Okamoto et al. |
| 7,232,581 B2 | 6/2007 | Mikkelsen et al. |
| 7,232,585 B2 | 6/2007 | Quan et al. |
| 7,238,514 B2 | 7/2007 | Matsuda et al. |
| 7,238,716 B2 | 7/2007 | Momose et al. |
| 7,241,411 B2 | 7/2007 | Berry et al. |
| 7,241,468 B2 | 7/2007 | Naber et al. |
| 7,241,606 B2 | 7/2007 | Kubota et al. |
| 7,241,785 B2 | 7/2007 | Momose et al. |
| 7,241,805 B2 | 7/2007 | Oberegger et al. |
| 7,243,910 B2 | 7/2007 | Bagley |
| 7,244,455 B2 | 7/2007 | Kiefer et al. |
| 7,244,462 B2 | 7/2007 | Amino et al. |
| 7,244,463 B2 | 7/2007 | Wadsworth et al. |
| 7,244,584 B2 | 7/2007 | Zuker et al. |
| 7,244,848 B2 | 7/2007 | Meerpoel et al. |
| 7,247,323 B2 | 7/2007 | George et al. |
| 7,247,324 B1 | 7/2007 | Wehling et al. |
| 7,247,325 B2 | 7/2007 | Baik et al. |
| 7,267,835 B2 | 9/2007 | Kitazume et al. |
| 7,288,270 B1 | 10/2007 | Sekharam et al. |
| 7,815,956 B2 | 10/2010 | Lee et al. |
| 7,851,005 B2 | 12/2010 | Bingley et al. |
| 2001/0000231 A1 | 4/2001 | Fotos et al. |
| 2001/0006694 A1 | 7/2001 | Fry |
| 2001/0024642 A1 | 9/2001 | Ream et al. |
| 2001/0033888 A1 | 10/2001 | Ohashi et al. |
| 2001/0048952 A1 | 12/2001 | Siskind |
| 2002/0001651 A1 | 1/2002 | Norris et al. |
| 2002/0001652 A1 | 1/2002 | Dron |
| 2002/0004092 A1 | 1/2002 | Riha |
| 2002/0006466 A1 | 1/2002 | Chaen |
| 2002/0025366 A1 | 2/2002 | Jager |
| 2002/0031522 A1 | 3/2002 | Baltimore |
| 2002/0044960 A1 | 4/2002 | Cherukuri |
| 2002/0051752 A1 | 5/2002 | Chiesi et al. |
| 2002/0051811 A1 | 5/2002 | Bakal |
| 2002/0058101 A1 | 5/2002 | Ohashi |
| 2002/0065245 A1 | 5/2002 | Brouwers |
| 2002/0068123 A1 | 6/2002 | Verhagen |
| 2002/0081361 A1 | 6/2002 | Towb |
| 2002/0090435 A1 | 7/2002 | Dewis |
| 2002/0090436 A1 | 7/2002 | Schroeder |
| 2002/0098272 A1 | 7/2002 | Silver |
| 2002/0110632 A1 | 8/2002 | Nunes et al. |
| 2002/0127319 A1 | 9/2002 | Gare |
| 2002/0132037 A1 | 9/2002 | Zhou |
| 2002/0132780 A1 | 9/2002 | Heisey et al. |
| 2002/0136802 A1 | 9/2002 | Mehansho et al. |
| 2002/0159956 A1 | 10/2002 | Ream et al. |
| 2002/0160090 A1 | 10/2002 | Lee |
| 2002/0160091 A1 | 10/2002 | Burgard |
| 2002/0165169 A1 | 11/2002 | Kim et al. |
| 2002/0187180 A1 | 12/2002 | Calton |
| 2002/0187219 A1 | 12/2002 | Yang et al. |
| 2002/0187232 A1 | 12/2002 | Lee |
| 2002/0187233 A1 | 12/2002 | Mann |
| 2002/0187239 A1 | 12/2002 | Miljkovic et al. |
| 2002/0188019 A1 | 12/2002 | Ley |
| 2002/0192350 A1 | 12/2002 | Hynes et al. |
| 2002/0192355 A1 | 12/2002 | Serpelloni |
| 2002/0193342 A1 | 12/2002 | Hamman et al. |
| 2002/0197371 A1 | 12/2002 | Lee et al. |
| 2002/0197372 A1 | 12/2002 | Janssen et al. |
| 2002/0197376 A1 | 12/2002 | Broz |
| 2003/0003212 A1 | 1/2003 | Chien |
| 2003/0008046 A1 | 1/2003 | Gerlat |
| 2003/0008057 A1 | 1/2003 | Hynes et al. |
| 2003/0008843 A1 | 1/2003 | Shaw Craig et al. |
| 2003/0008865 A1 | 1/2003 | Burgard |
| 2003/0021874 A1 | 1/2003 | Nunes et al. |
| 2003/0026879 A1 | 2/2003 | Mutilangi |
| 2003/0031772 A1 | 2/2003 | Zehner |
| 2003/0032600 A1 | 2/2003 | Ulrich et al. |
| 2003/0035875 A1 * | 2/2003 | Dulebohn et al. ............ 426/548 |
| 2003/0044502 A1 | 3/2003 | Ishii |
| 2003/0049208 A1 | 3/2003 | Ream et al. |
| 2003/0049352 A1 | 3/2003 | Mehansho et al. |
| 2003/0059511 A1 | 3/2003 | Ishii |
| 2003/0059519 A1 | 3/2003 | Merkel |
| 2003/0060428 A1 | 3/2003 | Hermansen et al. |
| 2003/0064104 A1 | 4/2003 | Stillman |
| 2003/0064146 A1 | 4/2003 | Yusuf et al. |
| 2003/0068429 A1 | 4/2003 | Frippiat et al. |
| 2003/0077368 A1 | 4/2003 | Serpelloni |
| 2003/0077369 A1 | 4/2003 | Jager et al. |
| 2003/0077374 A1 | 4/2003 | Ohishi et al. |
| 2003/0087019 A1 | 5/2003 | Malkki et al. |
| 2003/0095929 A1 | 5/2003 | Stier et al. |
| 2003/0096047 A1 | 5/2003 | Riha |
| 2003/0099760 A1 | 5/2003 | Okai |
| 2003/0108627 A1 | 6/2003 | Selzer et al. |
| 2003/0118654 A1 | 6/2003 | Santos |
| 2003/0124200 A1 | 7/2003 | Stone |
| 2003/0129217 A1 | 7/2003 | Festo |
| 2003/0138519 A1 | 7/2003 | Hill et al. |
| 2003/0138538 A1 | 7/2003 | Kitazume et al. |
| 2003/0152524 A1 | 8/2003 | Eshita |
| 2003/0152684 A1 * | 8/2003 | Saito et al. .................... 426/548 |
| 2003/0157229 A1 | 8/2003 | Blumenstein et al. |
| 2003/0161879 A1 | 8/2003 | Ohmori et al. |
| 2003/0165603 A1 | 9/2003 | Burklow et al. |
| 2003/0165604 A1 | 9/2003 | Tsubaki |
| 2003/0170365 A1 | 9/2003 | Huang |
| 2003/0171574 A1 | 9/2003 | Catani et al. |
| 2003/0171575 A1 | 9/2003 | Catani et al. |
| 2003/0190396 A1 | 10/2003 | Merkel |
| 2003/0207003 A1 | 11/2003 | Silver |
| 2003/0211214 A1 | 11/2003 | Riha et al. |
| 2003/0224094 A1 | 12/2003 | Bakal |
| 2003/0224097 A1 | 12/2003 | Neri |
| 2003/0228393 A1 | 12/2003 | Zhao |
| 2003/0228403 A1 | 12/2003 | Amino et al. |
| 2003/0235606 A1 | 12/2003 | Nussen |
| 2003/0236399 A1 | 12/2003 | Zheng et al. |
| 2004/0018290 A1 | 1/2004 | Jin |
| 2004/0022914 A1 | 2/2004 | Allen |
| 2004/0047921 A1 | 3/2004 | Simmons |
| 2004/0058050 A1 | 3/2004 | Guo |
| 2004/0076728 A2 | 4/2004 | Merkel et al. |
| 2004/0081712 A1 | 4/2004 | Hermansen et al. |
| 2004/0086605 A1 | 5/2004 | Sox |
| 2004/0096547 A1 | 5/2004 | Ferruzzi |
| 2004/0101491 A1 | 5/2004 | Stier |
| 2004/0105928 A1 | 6/2004 | Ishii |
| 2004/0115329 A1 | 6/2004 | Tamiya et al. |
| 2004/0120900 A1 | 6/2004 | Arsenault |
| 2004/0137094 A1 | 7/2004 | Mower et al. |
| 2004/0137111 A1 | 7/2004 | Yang |
| 2004/0142084 A1 | 7/2004 | Knueven |
| 2004/0146465 A1 | 7/2004 | Fujisawa |

(56) References Cited

U.S. PATENT DOCUMENTS

| | | |
|---|---|---|
| 2004/0151815 A1 | 8/2004 | Jensen |
| 2004/0156924 A1 | 8/2004 | Selzer et al. |
| 2004/0161422 A1 | 8/2004 | Ranganathan |
| 2004/0161524 A1 | 8/2004 | Sakai et al. |
| 2004/0166181 A1 | 8/2004 | Hegenauer et al. |
| 2004/0170735 A2 | 9/2004 | Merkel et al. |
| 2004/0175418 A1 | 9/2004 | Ferguson |
| 2004/0191400 A1 | 9/2004 | Catani et al. |
| 2004/0197401 A1 | 10/2004 | Calton et al. |
| 2004/0197453 A1 | 10/2004 | Hirao et al. |
| 2004/0213881 A1 | 10/2004 | Chien et al. |
| 2004/0213882 A1 | 10/2004 | Lauridsen |
| 2004/0228957 A1 | 11/2004 | Schmidt |
| 2004/0234648 A1 | 11/2004 | Mazurek et al. |
| 2004/0237663 A1 | 12/2004 | Farber et al. |
| 2004/0253327 A1 | 12/2004 | Niazi et al. |
| 2004/0254367 A1 | 12/2004 | Oku et al. |
| 2004/0258831 A1 | 12/2004 | Zhao et al. |
| 2005/0002992 A1 | 1/2005 | McCleary |
| 2005/0008732 A1 | 1/2005 | Gebreselassie et al. |
| 2005/0013902 A1 | 1/2005 | Pearce |
| 2005/0013915 A1 | 1/2005 | Riha |
| 2005/0013916 A1 | 1/2005 | Rathjen |
| 2005/0019412 A1 | 1/2005 | Bosch et al. |
| 2005/0020508 A1 | 1/2005 | Amino et al. |
| 2005/0025720 A1 | 2/2005 | Bailey |
| 2005/0025812 A1 | 2/2005 | Forest |
| 2005/0037121 A1 | 2/2005 | Rathjen |
| 2005/0037993 A1 | 2/2005 | Craig et al. |
| 2005/0038126 A1 | 2/2005 | Hermansen et al. |
| 2005/0042271 A1 | 2/2005 | Xiong et al. |
| 2005/0069616 A1 | 3/2005 | Lee |
| 2005/0084582 A1 | 4/2005 | Saelzer |
| 2005/0106305 A1 | 5/2005 | Abraham et al. |
| 2005/0112177 A1 | 5/2005 | Dopson et al. |
| 2005/0112240 A1 | 5/2005 | Grossman et al. |
| 2005/0112260 A1 | 5/2005 | Abraham et al. |
| 2005/0118284 A1 | 6/2005 | Khare |
| 2005/0118317 A1 | 6/2005 | Amino et al. |
| 2005/0136169 A1 | 6/2005 | Haung et al. |
| 2005/0137246 A1 | 6/2005 | Amino et al. |
| 2005/0152851 A1 | 7/2005 | Kaminski |
| 2005/0152997 A1 | 7/2005 | Selzer et al. |
| 2005/0155519 A1 | 7/2005 | Hansson et al. |
| 2005/0158444 A1 | 7/2005 | Koski |
| 2005/0170041 A1 | 8/2005 | Abraham et al. |
| 2005/0175755 A1 | 8/2005 | Nagashima et al. |
| 2005/0177886 A1 | 8/2005 | Margolskee |
| 2005/0184176 A1 | 8/2005 | Kuhn et al. |
| 2005/0191396 A1 | 9/2005 | Seltzer |
| 2005/0196503 A1 | 9/2005 | Srivastava |
| 2005/0202145 A1 | 9/2005 | Dorr et al. |
| 2005/0208108 A1 | 9/2005 | Jannusch et al. |
| 2005/0208192 A1 | 9/2005 | Nakakura et al. |
| 2005/0211239 A1 | 9/2005 | Koivikko |
| 2005/0214412 A1 | 9/2005 | Koo et al. |
| 2005/0214425 A1 | 9/2005 | Vazirani |
| 2005/0214426 A1 | 9/2005 | Saelzer |
| 2005/0215493 A1 | 9/2005 | Miyake et al. |
| 2005/0220868 A1 | 10/2005 | Lahl |
| 2005/0220964 A1 | 10/2005 | Rizo et al. |
| 2005/0226983 A1 | 10/2005 | Bakal |
| 2005/0226990 A1 | 10/2005 | Pellecer |
| 2005/0233046 A1 | 10/2005 | Krawczk et al. |
| 2005/0233052 A1 | 10/2005 | Sheng et al. |
| 2005/0238779 A1 | 10/2005 | Isoya |
| 2005/0238786 A1 | 10/2005 | Isoya et al. |
| 2005/0244538 A1 | 11/2005 | Andersen et al. |
| 2005/0245759 A1 | 11/2005 | Mori et al. |
| 2005/0249843 A1 | 11/2005 | Wallis |
| 2005/0249846 A1 | 11/2005 | Evans |
| 2005/0260322 A1 | 11/2005 | Takaichi et al. |
| 2005/0260328 A1 | 11/2005 | Lutz et al. |
| 2005/0272939 A1 | 12/2005 | Amino et al. |
| 2005/0276839 A1 | 12/2005 | Rifkin |
| 2005/0281929 A1 | 12/2005 | Sox |
| 2005/0287231 A1 | 12/2005 | Nussen |
| 2006/0002983 A1 | 1/2006 | Matsumoto et al. |
| 2006/0003053 A1 | 1/2006 | Ekanayake et al. |
| 2006/0013842 A1 | 1/2006 | Matkin et al. |
| 2006/0014208 A1 | 1/2006 | Zoller |
| 2006/0014819 A1 | 1/2006 | Mori |
| 2006/0019011 A1 | 1/2006 | Nerenberg |
| 2006/0024244 A1 | 2/2006 | Gebreselassie et al. |
| 2006/0024245 A1 | 2/2006 | Gebreselassie et al. |
| 2006/0024335 A1 | 2/2006 | Roger |
| 2006/0025584 A1 | 2/2006 | Eroma |
| 2006/0029719 A1 | 2/2006 | Catani |
| 2006/0034894 A1 | 2/2006 | Lakkis et al. |
| 2006/0034936 A1 | 2/2006 | Lakkis |
| 2006/0034993 A1 | 2/2006 | Saelzer |
| 2006/0045934 A1 | 3/2006 | Kabse et al. |
| 2006/0045953 A1 | 3/2006 | Tachdjian |
| 2006/0051456 A1 | 3/2006 | Kabse et al. |
| 2006/0051480 A1 | 3/2006 | Miles |
| 2006/0057247 A1 | 3/2006 | Nguyen et al. |
| 2006/0062747 A1 | 3/2006 | Rathjen |
| 2006/0062814 A1 | 3/2006 | Stier |
| 2006/0062872 A1 | 3/2006 | Gebreselassie et al. |
| 2006/0062884 A1 | 3/2006 | Benedict, III |
| 2006/0063737 A1 | 3/2006 | Holmdahl et al. |
| 2006/0068072 A9 | 3/2006 | Lee |
| 2006/0068073 A1 | 3/2006 | Catani et al. |
| 2006/0073254 A1 | 4/2006 | Catani |
| 2006/0073255 A1 | 4/2006 | Catani |
| 2006/0074249 A1 | 4/2006 | Kawahara |
| 2006/0083695 A1 | 4/2006 | Mori |
| 2006/0083837 A1 | 4/2006 | Monfre |
| 2006/0083838 A1 | 4/2006 | Jackson |
| 2006/0083839 A1 | 4/2006 | Sox |
| 2006/0086048 A1 | 4/2006 | Romley |
| 2006/0088635 A1 | 4/2006 | Goldman |
| 2006/0088636 A1 | 4/2006 | Goldman |
| 2006/0088637 A1 | 4/2006 | Goldman |
| 2006/0093720 A1 | 5/2006 | Tatz |
| 2006/0096587 A1 | 5/2006 | Brouns et al. |
| 2006/0105021 A1 | 5/2006 | Steele et al. |
| 2006/0110519 A1 | 5/2006 | Lauber |
| 2006/0127452 A1 | 6/2006 | Muller |
| 2006/0134197 A1 | 6/2006 | Uchida et al. |
| 2006/0134291 A1 | 6/2006 | Rathjen |
| 2006/0134292 A1 | 6/2006 | Abelyan et al. |
| 2006/0134294 A1 | 6/2006 | McKee |
| 2006/0134300 A1 | 6/2006 | Newman |
| 2006/0140989 A1 | 6/2006 | Harris et al. |
| 2006/0141119 A1 | 6/2006 | Yamamoto |
| 2006/0142555 A1 | 6/2006 | Jonnala |
| 2006/0159818 A1 | 7/2006 | Kunieda |
| 2006/0165864 A1 | 7/2006 | Ueno et al. |
| 2006/0188548 A1 | 8/2006 | Mattson et al. |
| 2006/0188627 A1 | 8/2006 | Brouns |
| 2006/0193957 A1 | 8/2006 | Chapello |
| 2006/0193958 A1 | 8/2006 | Chapello |
| 2006/0240143 A1 | 10/2006 | Andersen et al. |
| 2006/0240163 A1 | 10/2006 | Catani et al. |
| 2006/0246174 A1 | 11/2006 | Andersen et al. |
| 2006/0246207 A1 | 11/2006 | Silver |
| 2006/0257524 A1 | 11/2006 | Mikkelsen et al. |
| 2006/0257543 A1 | 11/2006 | Tachdjian et al. |
| 2006/0263411 A1 | 11/2006 | Tachdjian et al. |
| 2006/0286188 A1 | 12/2006 | Mower et al. |
| 2006/0286202 A1 | 12/2006 | Boghani et al. |
| 2006/0286203 A1 | 12/2006 | Boghani et al. |
| 2006/0286237 A1 | 12/2006 | Reiss et al. |
| 2006/0286239 A1 | 12/2006 | Rasouli et al. |
| 2006/0286259 A1 | 12/2006 | Hargreaves |
| 2007/0001561 A1 | 1/2007 | Sabo et al. |
| 2007/0003670 A1 | 1/2007 | Jendrysik et al. |
| 2007/0003679 A1 | 1/2007 | Shimizu et al. |
| 2007/0003680 A1 | 1/2007 | Tachdjian et al. |
| 2007/0009638 A1 | 1/2007 | Takemori et al. |
| 2007/0014909 A1 | 1/2007 | Mai et al. |
| 2007/0014910 A1 | 1/2007 | Altemueller et al. |
| 2007/0020368 A1 | 1/2007 | Maiullo et al. |

(56) References Cited

U.S. PATENT DOCUMENTS

| | | |
|---|---|---|
| 2007/0026121 A1 | 2/2007 | Benedict, III et al. |
| 2007/0031561 A1 | 2/2007 | Lakkis et al. |
| 2007/0031582 A1 | 2/2007 | Burger et al. |
| 2007/0036733 A1 | 2/2007 | Spence et al. |
| 2007/0048425 A1 | 3/2007 | Schwarz et al. |
| 2007/0054021 A1 | 3/2007 | Noomen et al. |
| 2007/0054023 A1 | 3/2007 | Bingley et al. |
| 2007/0059408 A1 | 3/2007 | Catani et al. |
| 2007/0059409 A1 | 3/2007 | Catani et al. |
| 2007/0059418 A1 | 3/2007 | Catani et al. |
| 2007/0059419 A1 | 3/2007 | Catani et al. |
| 2007/0059420 A1 | 3/2007 | Catani |
| 2007/0059421 A1 | 3/2007 | Catani et al. |
| 2007/0077201 A1 | 4/2007 | Reading et al. |
| 2007/0077210 A1 | 4/2007 | Gebreselassie et al. |
| 2007/0077308 A1 | 4/2007 | Giner |
| 2007/0077331 A1 | 4/2007 | Kiefer et al. |
| 2007/0077339 A1 | 4/2007 | Robbins |
| 2007/0082048 A1 | 4/2007 | Warner |
| 2007/0082102 A1 | 4/2007 | Magomet et al. |
| 2007/0082103 A1 | 4/2007 | Magomet et al. |
| 2007/0082104 A1 | 4/2007 | De Baets |
| 2007/0082105 A1 | 4/2007 | Robbins |
| 2007/0082106 A1 | 4/2007 | Lee et al. |
| 2007/0082116 A1 | 4/2007 | Sanders |
| 2007/0082888 A1 | 4/2007 | Meerpoel et al. |
| 2007/0082905 A1 | 4/2007 | DeVries et al. |
| 2007/0087038 A1 | 4/2007 | Richardson et al. |
| 2007/0087066 A1 | 4/2007 | Gerson et al. |
| 2007/0087108 A1 | 4/2007 | Wadsworth et al. |
| 2007/0092554 A1 | 4/2007 | Lindberg et al. |
| 2007/0092561 A1 | 4/2007 | Milne |
| 2007/0092587 A1 | 4/2007 | Ohnogi et al. |
| 2007/0092600 A1 | 4/2007 | Miyai et al. |
| 2007/0092623 A1 | 4/2007 | Shimizu et al. |
| 2007/0092624 A1 | 4/2007 | Iwasaki et al. |
| 2007/0098650 A1 | 5/2007 | Miller et al. |
| 2007/0098826 A1 | 5/2007 | Shin et al. |
| 2007/0098844 A1 | 5/2007 | Carroll et al. |
| 2007/0098845 A1 | 5/2007 | Soper et al. |
| 2007/0098867 A1 | 5/2007 | Singer |
| 2007/0099827 A1 | 5/2007 | Uotani et al. |
| 2007/0099869 A1 | 5/2007 | Oku et al. |
| 2007/0099934 A1 | 5/2007 | Lieven et al. |
| 2007/0104659 A1 | 5/2007 | Yasuda et al. |
| 2007/0104709 A1 | 5/2007 | Li et al. |
| 2007/0104829 A1 | 5/2007 | Soper et al. |
| 2007/0104848 A1 | 5/2007 | Thrasher et al. |
| 2007/0104851 A1 | 5/2007 | Iwasaki et al. |
| 2007/0110684 A1 | 5/2007 | Jensen et al. |
| 2007/0110689 A1 | 5/2007 | Feldschuh |
| 2007/0110833 A1 | 5/2007 | Jin et al. |
| 2007/0110834 A1 | 5/2007 | Jin et al. |
| 2007/0110868 A1 | 5/2007 | Lee et al. |
| 2007/0110874 A1 | 5/2007 | Fang et al. |
| 2007/0113840 A1 | 5/2007 | Koivikko |
| 2007/0116764 A1 | 5/2007 | Marunaka |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0116851 A1 | 5/2007 | Shi et al. |
| 2007/0118916 A1 | 5/2007 | Puzio et al. |
| 2007/0122360 A1 | 5/2007 | Oniki et al. |
| 2007/0122400 A1 | 5/2007 | Kubo et al. |
| 2007/0122455 A1 | 5/2007 | Myers et al. |
| 2007/0122456 A1 | 5/2007 | Lindberg |
| 2007/0122471 A1 | 5/2007 | Murakawa et al. |
| 2007/0122490 A1 | 5/2007 | Peshoff |
| 2007/0122504 A1 | 5/2007 | Moon et al. |
| 2007/0122507 A1 | 5/2007 | Palu et al. |
| 2007/0122508 A1 | 5/2007 | Kim et al. |
| 2007/0122535 A1 | 5/2007 | Stouffs et al. |
| 2007/0128130 A1 | 6/2007 | Kropf et al. |
| 2007/0128273 A1 | 6/2007 | Miura et al. |
| 2007/0128285 A1 | 6/2007 | Jin et al. |
| 2007/0128299 A1 | 6/2007 | Nagai et al. |
| 2007/0128301 A1 | 6/2007 | Saltzman et al. |
| 2007/0128311 A1 | 6/2007 | Prakash et al. |
| 2007/0128323 A1 | 6/2007 | Tsujii et al. |
| 2007/0128332 A1 | 6/2007 | Toves |
| 2007/0129283 A1 | 6/2007 | McKinney et al. |
| 2007/0129402 A1 | 6/2007 | Ueki et al. |
| 2007/0129430 A1 | 6/2007 | Miyata et al. |
| 2007/0134168 A1 | 6/2007 | Dodds et al. |
| 2007/0134171 A1 | 6/2007 | Dodds et al. |
| 2007/0134353 A1 | 6/2007 | Kang et al. |
| 2007/0134389 A1 | 6/2007 | Pei et al. |
| 2007/0134390 A1 | 6/2007 | Prakash et al. |
| 2007/0134391 A1 | 6/2007 | Prakash et al. |
| 2007/0134400 A1 | 6/2007 | Kealey et al. |
| 2007/0134404 A1 | 6/2007 | Lacy et al. |
| 2007/0134493 A1 | 6/2007 | Meghpara |
| 2007/0134999 A1 | 6/2007 | Ficht et al. |
| 2007/0138538 A1 | 6/2007 | Kitazume et al. |
| 2007/0140984 A1 | 6/2007 | Kusano et al. |
| 2007/0140998 A1 | 6/2007 | Kato et al. |
| 2007/0141161 A1 | 6/2007 | Shaw et al. |
| 2007/0141186 A1 | 6/2007 | Shin |
| 2007/0141198 A1 | 6/2007 | Yang |
| 2007/0141200 A1 | 6/2007 | Mikkelsen |
| 2007/0141203 A1 | 6/2007 | Cook |
| 2007/0141204 A1 | 6/2007 | Xiong et al. |
| 2007/0141217 A1 | 6/2007 | Benedict et al. |
| 2007/0144544 A1 | 6/2007 | Cai et al. |
| 2007/0148103 A1 | 6/2007 | Harvey |
| 2007/0148105 A1 | 6/2007 | Spector |
| 2007/0148108 A1 | 6/2007 | Sakamoto et al. |
| 2007/0148230 A1 | 6/2007 | Fujiwara et al. |
| 2007/0148235 A1 | 6/2007 | Nakagami et al. |
| 2007/0148252 A1 | 6/2007 | Shaw et al. |
| 2007/0148283 A1 | 6/2007 | Harvey et al. |
| 2007/0148284 A1 | 6/2007 | Jani et al. |
| 2007/0148285 A1 | 6/2007 | Yang |
| 2007/0148286 A1 | 6/2007 | Jani et al. |
| 2007/0148303 A1 | 6/2007 | Yeager et al. |
| 2007/0148305 A1 | 6/2007 | Sherwood et al. |
| 2007/0148307 A1 | 6/2007 | Sherwood et al. |
| 2007/0148308 A1 | 6/2007 | Niwa |
| 2007/0148321 A1 | 6/2007 | Ashida et al. |
| 2007/0149608 A1 | 6/2007 | Yasuma et al. |
| 2007/0154575 A1 | 7/2007 | Shimoda et al. |
| 2007/0154580 A1 | 7/2007 | Palu et al. |
| 2007/0154614 A1 | 7/2007 | Sherwood et al. |
| 2007/0155707 A1 | 7/2007 | Dasse et al. |
| 2007/0155747 A1 | 7/2007 | Dasse et al. |
| 2007/0155780 A1 | 7/2007 | Nakata et al. |
| 2007/0155796 A1 | 7/2007 | Fujishima |
| 2007/0155808 A1 | 7/2007 | Yasuma et al. |
| 2007/0160589 A1 | 7/2007 | Mattson |
| 2007/0160687 A1 | 7/2007 | Kim et al. |
| 2007/0160698 A1 | 7/2007 | Waga et al. |
| 2007/0160699 A1 | 7/2007 | Kim |
| 2007/0160700 A1 | 7/2007 | Palu et al. |

(56) References Cited

U.S. PATENT DOCUMENTS

| | | |
|---|---|---|
| 2007/0160702 A1 | 7/2007 | Wehling et al. |
| 2007/0160703 A1 | 7/2007 | Wehling et al. |
| 2007/0160704 A1 | 7/2007 | Lu et al. |
| 2007/0160707 A1 | 7/2007 | Garcia |
| 2007/0160731 A1 | 7/2007 | Rathjen et al. |
| 2007/0160734 A1 | 7/2007 | Van Bokkelen et al. |
| 2007/0160738 A1 | 7/2007 | Van Bokkelen et al. |
| 2007/0161053 A1 | 7/2007 | Li et al. |
| 2007/0166243 A1 | 7/2007 | Yoshida et al. |
| 2007/0166246 A1 | 7/2007 | Takagaki et al. |
| 2007/0166407 A1 | 7/2007 | Tanaka et al. |
| 2007/0166416 A1 | 7/2007 | Palu et al. |
| 2007/0172510 A1 | 7/2007 | Melton |
| 2007/0172515 A1 | 7/2007 | Fuisz |
| 2007/0172541 A1 | 7/2007 | Donaire et al. |
| 2007/0178123 A1 | 8/2007 | Levenson et al. |
| 2007/0178174 A1 | 8/2007 | Kim et al. |
| 2007/0178181 A1 | 8/2007 | Jensen et al. |
| 2007/0178187 A1 | 8/2007 | Shetty |
| 2007/0178188 A1 | 8/2007 | Shetty |
| 2007/0178193 A1 | 8/2007 | Chang et al. |
| 2007/0185312 A1 | 8/2007 | Zuker et al. |
| 2007/0196539 A1 | 8/2007 | Yang et al. |
| 2007/0196558 A1 | 8/2007 | Yamaguchi et al. |
| 2007/0207093 A1 | 9/2007 | Bryant et al. |
| 2007/0212460 A1 | 9/2007 | Inoue et al. |
| 2007/0224321 A1 | 9/2007 | Prakash et al. |
| 2007/0225348 A1 | 9/2007 | Edens et al. |
| 2007/0231367 A1 | 10/2007 | Fukui |
| 2007/0237859 A1 | 10/2007 | De Albertis et al. |
| 2007/0275147 A1 | 11/2007 | Prakash et al. |
| 2007/0292582 A1 | 12/2007 | Prakash et al. |
| 2008/0051341 A1 | 2/2008 | Hermansen et al. |
| 2008/0107788 A1 | 5/2008 | Silver |
| 2009/0202697 A1 | 8/2009 | Erickson et al. |

FOREIGN PATENT DOCUMENTS

| | | |
|---|---|---|
| AU | 0744656 | 2/2002 |
| AU | 2004202670 | 1/2005 |
| AU | 783688 | 11/2005 |
| AU | 783688 B2 | 11/2005 |
| AU | 0784422 | 3/2006 |
| AU | 2005211541 | 4/2006 |
| AU | 2002255076 | 1/2007 |
| AU | 2007100471 | 8/2007 |
| AU | 2002305211 | 9/2007 |
| AU | 2002355946 | 9/2007 |
| AU | 2007216740 | 10/2007 |
| AU | 2006201821 | 11/2007 |
| BE | 1015783 | 8/2005 |
| CA | 2042920 C | 11/1991 |
| CA | 1310963 C | 12/1992 |
| CA | 2199806 | 3/1996 |
| CA | 2185510 A1 | 3/1998 |
| CA | 2238559 A1 | 11/1998 |
| CA | 2322825 | 6/1999 |
| CA | 2319059 AA | 8/1999 |
| CA | 2478619 | 9/1999 |
| CA | 2278083 A1 | 1/2001 |
| CA | 2278083 A3 | 1/2001 |
| CA | 2398445 | 8/2001 |
| CA | 2441940 | 10/2002 |
| CA | 2442204 | 10/2002 |
| CA | 2429962 | 11/2003 |
| CA | 2493320 | 2/2004 |
| CA | 2598109 | 9/2006 |
| CA | 2602498 | 11/2006 |
| CA | 2605564 | 11/2006 |
| CA | 2605573 | 11/2006 |
| CA | 2613722 | 2/2007 |
| CA | 2580429 | 9/2007 |
| CH | 515685 A | 11/1971 |
| CN | 1074350 A | 7/1993 |
| CN | 1082844 A | 3/1994 |
| CN | 1084703 | 4/1994 |
| CN | 1089096 | 7/1994 |
| CN | 1090478 A | 8/1994 |
| CN | 1092621 A | 9/1994 |
| CN | 1094592 A | 11/1994 |
| CN | 1113122 A | 12/1995 |
| CN | 1136417 A | 11/1996 |
| CN | 1147917 A | 4/1997 |
| CN | 1148476 | 4/1997 |
| CN | 1166301 A | 12/1997 |
| CN | 1192447 A | 9/1998 |
| CN | 1238341 A | 12/1999 |
| CN | 1243835 A | 2/2000 |
| CN | 1314085 | 9/2001 |
| CN | 1078217 C | 1/2002 |
| CN | 1435203 A | 8/2003 |
| CN | 1440691 | 9/2003 |
| CN | 1449691 | 10/2003 |
| CN | 1490013 A | 4/2004 |
| CN | 1505938 A | 6/2004 |
| CN | 1524448 | 9/2004 |
| CN | 1539432 A | 10/2004 |
| CN | 1644109 | 7/2005 |
| CN | 1666640 A | 9/2005 |
| CN | 1695602 A | 11/2005 |
| DE | 10008279 | 8/2001 |
| DE | 20115366 | 2/2002 |
| DE | 102005024183 A1 | 12/2005 |
| EP | 0009325 | 4/1980 |
| EP | 0060903 | 9/1982 |
| EP | 0154235 A2 | 9/1985 |
| EP | 0157873 B2 | 10/1985 |
| EP | 0185442 A2 | 6/1986 |
| EP | 0199257 A2 | 10/1986 |
| EP | 0199258 A2 | 10/1986 |
| EP | 0207515 A1 | 1/1987 |
| EP | 0207516 A1 | 1/1987 |
| EP | 0224106 | 6/1987 |
| EP | 0246177 A2 | 11/1987 |
| EP | 0254401 A2 | 1/1988 |
| EP | 0255343 A2 | 2/1988 |
| EP | 0256475 A2 | 2/1988 |
| EP | 0257626 A1 | 3/1988 |
| EP | 0259996 | 3/1988 |
| EP | 0313234 | 4/1989 |
| EP | 0396214 A2 | 4/1989 |
| EP | 0325790 A2 | 8/1989 |
| EP | 0346866 | 12/1989 |
| EP | 0354680 | 2/1990 |
| EP | 0375239 * | 6/1990 |
| EP | 0375239 A2 | 6/1990 |
| EP | 0386963 A2 | 9/1990 |
| EP | 0390438 | 10/1990 |
| EP | 0398466 A2 | 11/1990 |
| EP | 0413539 | 2/1991 |
| EP | 0415635 A1 | 3/1991 |
| EP | 0418616 | 3/1991 |
| EP | 0420539 A2 | 4/1991 |
| EP | 0426428 | 5/1991 |
| EP | 0210695 B1 | 9/1991 |
| EP | 0447359 A1 | 9/1991 |
| EP | 0452262 A3 | 10/1991 |
| EP | 0455600 A1 | 11/1991 |
| EP | 0457724 A1 | 11/1991 |
| EP | 0458750 A1 | 11/1991 |
| EP | 0459952 A3 | 12/1991 |
| EP | 0301653 B1 | 1/1992 |
| EP | 0464833 B | 1/1992 |
| EP | 0470259 B | 2/1992 |
| EP | 0267809 B1 | 3/1992 |
| EP | 0483755 A2 | 5/1992 |
| EP | 0485170 A1 | 5/1992 |
| EP | 0493919 A | 7/1992 |
| EP | 0497439 A1 | 8/1992 |
| EP | 0500977 A1 | 9/1992 |
| EP | 0366251 B1 | 12/1992 |
| EP | 0407453 B1 | 1/1993 |
| EP | 0310341 B1 | 3/1993 |

(56) References Cited

FOREIGN PATENT DOCUMENTS

| | | |
|---|---|---|
| EP | 0531935 A2 | 3/1993 |
| EP | 0314626 B1 | 5/1993 |
| EP | 0290843 B1 | 7/1993 |
| EP | 0553777 A | 8/1993 |
| EP | 0478580 B1 | 10/1993 |
| EP | 0420402 B1 | 11/1993 |
| EP | 0470259 B1 | 1/1994 |
| EP | 0587904 A1 | 3/1994 |
| EP | 0464833 B1 | 6/1994 |
| EP | 0599646 A2 | 6/1994 |
| EP | 0334617 B1 | 9/1994 |
| EP | 0555237 B1 | 1/1995 |
| EP | 0371584 B1 | 2/1995 |
| EP | 0416718 B1 | 3/1995 |
| EP | 0507598 B1 | 6/1995 |
| EP | 0657169 | 6/1995 |
| EP | 0382578 B1 | 9/1995 |
| EP | 0680971 A1 | 11/1995 |
| EP | 0287957 B2 | 8/1996 |
| EP | 0727149 A2 | 8/1996 |
| EP | 0727150 A2 | 8/1996 |
| EP | 0727151 A2 | 8/1996 |
| EP | 0727152 A2 | 8/1996 |
| EP | 0728419 A2 | 8/1996 |
| EP | 0396741 B1 | 9/1996 |
| EP | 0335265 B1 | 10/1996 |
| EP | 0779296 A2 | 6/1997 |
| EP | 0792589 A | 9/1997 |
| EP | 0845217 A1 | 6/1998 |
| EP | 0540460 B1 | 7/1998 |
| EP | 0861035 B | 9/1998 |
| EP | 0862864 | 9/1998 |
| EP | 0862864 A | 9/1998 |
| EP | 0472500 B1 | 11/1998 |
| EP | 0684772 B1 | 7/1999 |
| EP | 0605261 B1 | 9/1999 |
| EP | 0941671 A2 | 9/1999 |
| EP | 0941671 A3 | 9/1999 |
| EP | 0777421 B1 | 10/1999 |
| EP | 0956780 A1 | 11/1999 |
| EP | 0960571 A2 | 12/1999 |
| EP | 0968232 B1 | 1/2000 |
| EP | 0974349 A1 | 1/2000 |
| EP | 0390299 B2 | 7/2000 |
| EP | 1040766 B | 10/2000 |
| EP | 1041897 B | 10/2000 |
| EP | 1041898 | 10/2000 |
| EP | 1046347 A1 | 10/2000 |
| EP | 1049388 A1 | 11/2000 |
| EP | 1060674 A2 | 12/2000 |
| EP | 0582396 B1 | 1/2001 |
| EP | 1080645 A1 | 3/2001 |
| EP | 0684995 B1 | 6/2001 |
| EP | 0748814 B1 | 6/2001 |
| EP | 0814674 B1 | 6/2001 |
| EP | 1111065 A2 | 6/2001 |
| EP | 0762836 B1 | 7/2001 |
| EP | 0882408 B1 | 11/2001 |
| EP | 0514937 B1 | 12/2001 |
| EP | 1163901 A | 12/2001 |
| EP | 0964621 B1 | 2/2002 |
| EP | 1177728 A1 | 2/2002 |
| EP | 1179300 A1 | 2/2002 |
| EP | 0968231 B1 | 6/2002 |
| EP | 1210880 A1 | 6/2002 |
| EP | 1224868 | 7/2002 |
| EP | 0871378 B1 | 8/2002 |
| EP | 0750849 B1 | 9/2002 |
| EP | 1250845 | 10/2002 |
| EP | 0768041 B1 | 12/2002 |
| EP | 1264896 A1 | 12/2002 |
| EP | 1267815 B1 | 1/2003 |
| EP | 1272151 B1 | 1/2003 |
| EP | 0967888 | 3/2003 |
| EP | 1077726 B1 | 3/2003 |
| EP | 1293251 A1 | 3/2003 |
| EP | 0981533 B1 | 4/2003 |
| EP | 1196050 B1 | 4/2003 |
| EP | 0963707 B1 | 5/2003 |
| EP | 1045644 B1 | 5/2003 |
| EP | 1139794 B1 | 9/2003 |
| EP | 1340431 A1 | 9/2003 |
| EP | 1077034 B1 | 10/2003 |
| EP | 0988796 B1 | 11/2003 |
| EP | 1385394 B | 2/2004 |
| EP | 1399034 B | 3/2004 |
| EP | 1407679 A1 | 4/2004 |
| EP | 1416450 A1 | 5/2004 |
| EP | 1421859 A1 | 5/2004 |
| EP | 0889694 B1 | 6/2004 |
| EP | 1426043 | 6/2004 |
| EP | 1295533 B1 | 7/2004 |
| EP | 1440623 A1 | 7/2004 |
| EP | 1449832 A1 | 8/2004 |
| EP | 0979037 B1 | 9/2004 |
| EP | 1460081 A1 | 9/2004 |
| EP | 0794259 B1 | 10/2004 |
| EP | 1109461 B1 | 10/2004 |
| EP | 1469081 | 10/2004 |
| EP | 0861035 B1 | 12/2004 |
| EP | 0945074 B1 | 4/2005 |
| EP | 1526779 B | 5/2005 |
| EP | 1529776 A2 | 5/2005 |
| EP | 1576890 A1 | 9/2005 |
| EP | 1354067 B1 | 10/2005 |
| EP | 1591021 A1 | 11/2005 |
| EP | 0841397 B1 | 1/2006 |
| EP | 1415545 B1 | 1/2006 |
| EP | 1487846 B1 | 1/2006 |
| EP | 1616570 A1 | 1/2006 |
| EP | 1618799 | 1/2006 |
| EP | 1629730 A1 | 1/2006 |
| EP | 1623629 | 2/2006 |
| EP | 1623630 A | 2/2006 |
| EP | 1639901 A | 3/2006 |
| EP | 1042963 B1 | 4/2006 |
| EP | 1643220 A1 | 4/2006 |
| EP | 1649759 A1 | 4/2006 |
| EP | 1657246 A1 | 5/2006 |
| EP | 1669080 A | 6/2006 |
| EP | 1673985 A | 6/2006 |
| EP | 1673986 A2 | 6/2006 |
| EP | 1674474 A1 | 6/2006 |
| EP | 1391154 B1 | 10/2006 |
| EP | 1721620 | 11/2006 |
| EP | 1245578 B1 | 4/2007 |
| EP | 1361264 B1 | 4/2007 |
| EP | 1653810 B1 | 4/2007 |
| EP | 1772058 A1 | 4/2007 |
| EP | 1772461 A1 | 4/2007 |
| EP | 1776871 A2 | 4/2007 |
| EP | 1776944 A1 | 4/2007 |
| EP | 1777296 A2 | 4/2007 |
| EP | 0919208 B1 | 5/2007 |
| EP | 1265494 B1 | 5/2007 |
| EP | 1297749 B1 | 5/2007 |
| EP | 1392291 B1 | 5/2007 |
| EP | 1545230 B1 | 5/2007 |
| EP | 1782832 A1 | 5/2007 |
| EP | 1787991 A1 | 5/2007 |
| EP | 1790334 A2 | 5/2007 |
| EP | 1790687 A2 | 5/2007 |
| EP | 1219630 B1 | 6/2007 |
| EP | 1335020 B1 | 6/2007 |
| EP | 1641784 B1 | 6/2007 |
| EP | 1792581 A1 | 6/2007 |
| EP | 1793005 A1 | 6/2007 |
| EP | 1795204 A1 | 6/2007 |
| EP | 1797769 A2 | 6/2007 |
| EP | 1797770 A2 | 6/2007 |
| EP | 1245582 B1 | 7/2007 |
| EP | 1355886 B1 | 7/2007 |
| EP | 1377280 B1 | 7/2007 |
| EP | 1803452 A1 | 7/2007 |

(56) References Cited

FOREIGN PATENT DOCUMENTS

| | | |
|---|---|---|
| EP | 1803709 A1 | 7/2007 |
| EP | 1806059 A2 | 7/2007 |
| EP | 1806125 A1 | 7/2007 |
| EP | 1806133 A1 | 7/2007 |
| EP | 1806341 A2 | 7/2007 |
| EP | 1808497 A1 | 7/2007 |
| EP | 1810677 A1 | 7/2007 |
| EP | 1813156 A1 | 8/2007 |
| EP | 1856967 A | 11/2007 |
| EP | 1364587 A1 | 9/2008 |
| FR | 2778822 A | 11/1999 |
| GB | 780886 | 8/1957 |
| GB | 2292314 | 2/1996 |
| GB | 2380936 | 4/2003 |
| GB | 2418856 | 4/2006 |
| JP | 51019169 | 2/1976 |
| JP | 52041275 | 3/1977 |
| JP | 52057366 A2 | 5/1977 |
| JP | 52120171 | 10/1977 |
| JP | 52122676 | 10/1977 |
| JP | 52143256 A2 | 11/1977 |
| JP | 53148575 | 12/1978 |
| JP | 54002381 | 1/1979 |
| JP | 54147976 A2 | 11/1979 |
| JP | 55013017 A2 | 1/1980 |
| JP | 55013043 A2 | 1/1980 |
| JP | 55015747 A2 | 2/1980 |
| JP | 55050866 A2 | 4/1980 |
| JP | 55071448 A2 | 5/1980 |
| JP | 55074778 | 6/1980 |
| JP | 55088675 | 7/1980 |
| JP | 55092400 A | 7/1980 |
| JP | 55114271 | 9/1980 |
| JP | 56011772 A2 | 2/1981 |
| JP | 56011774 A | 2/1981 |
| JP | 56055174 | 5/1981 |
| JP | 56109551 A2 | 8/1981 |
| JP | 56121453 A | 9/1981 |
| JP | 56121454 | 9/1981 |
| JP | 56121455 A | 9/1981 |
| JP | 56144038 | 11/1981 |
| JP | 57086264 A | 5/1982 |
| JP | 57141248 | 9/1982 |
| JP | 57183705 A2 | 11/1982 |
| JP | 57206389 A2 | 12/1982 |
| JP | 57206603 A2 | 12/1982 |
| JP | 58005160 | 1/1983 |
| JP | 58031961 A2 | 2/1983 |
| JP | 58040064 | 3/1983 |
| JP | 58040064 A2 | 3/1983 |
| JP | 58116674 A | 7/1983 |
| JP | 58141760 A2 | 8/1983 |
| JP | 58216663 | 12/1983 |
| JP | 59034826 A2 | 2/1984 |
| JP | 59045848 | 3/1984 |
| JP | 59051265 | 3/1984 |
| JP | 59071662 | 4/1984 |
| JP | 59120073 | 7/1984 |
| JP | 59154957 | 9/1984 |
| JP | 60019474 A | 1/1985 |
| JP | 60019475 A | 1/1985 |
| JP | 60027360 | 2/1985 |
| JP | 60037950 | 2/1985 |
| JP | 60075252 | 4/1985 |
| JP | 60098968 A2 | 6/1985 |
| JP | 60130509 | 7/1985 |
| JP | 60160823 A2 | 8/1985 |
| JP | 60188035 | 9/1985 |
| JP | 60188035 A | 9/1985 |
| JP | 60199364 | 10/1985 |
| JP | 60221056 A | 11/1985 |
| JP | 61005759 A | 1/1986 |
| JP | 61005760 A | 1/1986 |
| JP | 61108332 | 5/1986 |
| JP | 61202667 A2 | 9/1986 |
| JP | 61257928 | 11/1986 |
| JP | 61260052 | 11/1986 |
| JP | 62-079752 | 4/1987 |
| JP | 62083852 A2 | 4/1987 |
| JP | 62091161 | 4/1987 |
| JP | 62091161 A | 4/1987 |
| JP | 62151498 A | 7/1987 |
| JP | 63087959 A | 4/1988 |
| JP | 63-258557 | 10/1988 |
| JP | 63304964 | 12/1988 |
| JP | 63304964 A2 | 12/1988 |
| JP | 01063356 A2 | 3/1989 |
| JP | 02257851 | 10/1990 |
| JP | 02261359 A | 10/1990 |
| JP | 3067560 A | 3/1991 |
| JP | 3180155 A2 | 8/1991 |
| JP | 3251160 | 11/1991 |
| JP | 04091753 A2 | 3/1992 |
| JP | 4135460 | 5/1992 |
| JP | 04135460 A | 5/1992 |
| JP | 04148659 A | 5/1992 |
| JP | 04282398 A | 10/1992 |
| JP | 5199855 | 8/1993 |
| JP | 05207861 A2 | 8/1993 |
| JP | 58149655 | 9/1993 |
| JP | 06133724 | 5/1994 |
| JP | 06192283 A | 7/1994 |
| JP | 06073468 B4 | 9/1994 |
| JP | 6276997 A2 | 10/1994 |
| JP | 07031407 A | 2/1995 |
| JP | 07143860 A | 6/1995 |
| JP | 2006174844 | 6/1995 |
| JP | 07177862 A2 | 7/1995 |
| JP | 08000214 | 1/1996 |
| JP | 08000214 A | 1/1996 |
| JP | 8089207 | 4/1996 |
| JP | 08089207 A | 4/1996 |
| JP | 8109193 A2 | 4/1996 |
| JP | 8140566 | 6/1996 |
| JP | 08256725 A | 10/1996 |
| JP | 8256725 A | 10/1996 |
| JP | 9051777 A | 2/1997 |
| JP | 9052825 | 2/1997 |
| JP | 09052825 A | 2/1997 |
| JP | 2006061160 | 3/1997 |
| JP | 2007082491 | 3/1997 |
| JP | 09104625 A2 | 4/1997 |
| JP | 09107913 A2 | 4/1997 |
| JP | 09173009 A | 7/1997 |
| JP | 09173009 A2 | 7/1997 |
| JP | 9194370 | 7/1997 |
| JP | 09194370 A | 7/1997 |
| JP | 09194370 A2 | 7/1997 |
| JP | 9220069 A | 8/1997 |
| JP | 9238641 A | 9/1997 |
| JP | 10136952 A | 5/1998 |
| JP | 10136953 A | 5/1998 |
| JP | 10150958 A | 6/1998 |
| JP | 10150958 A | 6/1998 |
| JP | 10150958 A2 | 6/1998 |
| JP | 10248501 A2 | 9/1998 |
| JP | 10262599 | 10/1998 |
| JP | 10271928 A2 | 10/1998 |
| JP | 10276710 | 10/1998 |
| JP | 10276712 A | 10/1998 |
| JP | 10-304829 A | 11/1998 |
| JP | 10313819 A | 12/1998 |
| JP | 10337154 | 12/1998 |
| JP | 11075762 A | 2/1999 |
| JP | 11100395 A2 | 4/1999 |
| JP | 11113492 | 4/1999 |
| JP | 11113493 | 4/1999 |
| JP | 11-123069 | 5/1999 |
| JP | 11123069 A | 5/1999 |
| JP | 11243859 | 9/1999 |
| JP | 11243906 | 9/1999 |
| JP | 11243906 A2 | 9/1999 |
| JP | 11-346708 | 12/1999 |
| JP | 11346708 | 12/1999 |

(56) References Cited

FOREIGN PATENT DOCUMENTS

| | | |
|---|---|---|
| JP | 2000004852 A2 | 1/2000 |
| JP | 2000007547 | 1/2000 |
| JP | 2000032859 A2 | 2/2000 |
| JP | 2000037178 A2 | 2/2000 |
| JP | 2000037178 A2 | 2/2000 |
| JP | 2000236842 | 9/2000 |
| JP | 2000262216 A2 | 9/2000 |
| JP | 2000290199 | 10/2000 |
| JP | 2001112433 | 4/2001 |
| JP | 2001120218 | 5/2001 |
| JP | 2001120218 A | 5/2001 |
| JP | 2001161308 A2 | 6/2001 |
| JP | 2001161309 A | 6/2001 |
| JP | 2001211854 A | 8/2001 |
| JP | 2001245640 A2 | 9/2001 |
| JP | 2001252040 A2 | 9/2001 |
| JP | 2001258502 | 9/2001 |
| JP | 4287658 | 10/2001 |
| JP | 2001292722 A | 10/2001 |
| JP | 2001321115 A2 | 11/2001 |
| JP | 2001333729 | 12/2001 |
| JP | 2002017317 A | 1/2002 |
| JP | 2002034502 | 2/2002 |
| JP | 2002045145 A | 2/2002 |
| JP | 2002097143 | 4/2002 |
| JP | 2002101844 | 4/2002 |
| JP | 2002142711 | 5/2002 |
| JP | 2002171930 A2 | 6/2002 |
| JP | 2002234844 | 8/2002 |
| JP | 2002262822 A2 | 9/2002 |
| JP | 2002281932 | 10/2002 |
| JP | 2003009878 A2 | 1/2003 |
| JP | 2003093014 | 4/2003 |
| JP | 2003093014 A | 4/2003 |
| JP | 2003164268 A2 | 6/2003 |
| JP | 2003180288 | 7/2003 |
| JP | 2003192607 A | 7/2003 |
| JP | 2003210147 A2 | 7/2003 |
| JP | 2003246729 | 9/2003 |
| JP | 2003300996 A | 10/2003 |
| JP | 2004033226 | 2/2004 |
| JP | 2004073197 | 3/2004 |
| JP | 2004083529 A | 3/2004 |
| JP | 2004089028 | 3/2004 |
| JP | 2004149481 | 5/2004 |
| JP | 2004149481 A | 5/2004 |
| JP | 2005336078 | 5/2004 |
| JP | 2004331576 A | 11/2004 |
| JP | 2004344071 | 12/2004 |
| JP | 2004344071 A | 12/2004 |
| JP | 2006238826 | 3/2005 |
| JP | 2005168458 | 6/2005 |
| JP | 2005269938 A | 6/2005 |
| JP | 2005200330 A | 7/2005 |
| JP | 2005237303 | 9/2005 |
| JP | 2005237303 A | 9/2005 |
| JP | 2005261395 A | 9/2005 |
| JP | 2005278467 | 10/2005 |
| JP | 2005295953 | 10/2005 |
| JP | 2006204287 | 10/2005 |
| JP | 2005320281 A | 11/2005 |
| JP | 2006/081544 A | 3/2006 |
| JP | 2006345854 | 5/2006 |
| JP | 2006223104 | 8/2006 |
| JP | 2006238828 | 9/2006 |
| JP | 2006314240 A | 11/2006 |
| JP | 2007014212 | 1/2007 |
| JP | 2008000147 | 1/2008 |
| JP | 2008000148 | 1/2008 |
| KR | 960016568 B1 | 12/1996 |
| KR | 2003073901 A | 9/2003 |
| KR | 2003077349 A | 10/2003 |
| KR | 2004092232 | 11/2004 |
| KR | 20050007255 | 1/2005 |
| KR | 2005065486 A | 6/2005 |
| KR | 2005/088031 | 9/2005 |
| KR | 2006064589 A | 6/2006 |
| RU | 2169480 C2 | 6/2001 |
| RU | 2248708 | 3/2005 |
| RU | 2263499 C1 | 11/2005 |
| RU | 2270255 C2 | 2/2006 |
| UA | 62095 | 12/2003 |
| WO | WO8500809 A1 | 2/1985 |
| WO | WO8501862 | 5/1985 |
| WO | WO 86/01690 A1 | 3/1986 |
| WO | WO 86/03378 A1 | 8/1986 |
| WO | WO 87/00732 A1 | 2/1987 |
| WO | WO 88/08256 A1 | 11/1988 |
| WO | WO 88/08674 A1 | 11/1988 |
| WO | WO 89/03182 A1 | 4/1989 |
| WO | WO8904609 | 6/1989 |
| WO | WO 89/09288 A1 | 10/1989 |
| WO | WO 90/15545 A1 | 12/1990 |
| WO | WO9103147 | 3/1991 |
| WO | WO 91/04342 A1 | 4/1991 |
| WO | WO9118523 A1 | 12/1991 |
| WO | WO 92/00950 A1 | 1/1992 |
| WO | WO 92/00953 A1 | 1/1992 |
| WO | WO9202145 | 2/1992 |
| WO | WO 92/03065 A1 | 3/1992 |
| WO | WO 92/06601 A1 | 4/1992 |
| WO | WO 92/07473 A1 | 5/1992 |
| WO | WO 92/11084 A1 | 7/1992 |
| WO | WO 93/00828 A2 | 1/1993 |
| WO | WO9310677 A1 | 6/1993 |
| WO | WO 93/13677 A1 | 7/1993 |
| WO | WO9321785 | 11/1993 |
| WO | WO 94/00028 A2 | 1/1994 |
| WO | WO9402441 A1 | 2/1994 |
| WO | WO9406412 | 3/1994 |
| WO | WO 94/08471 A1 | 4/1994 |
| WO | WO 94/12058 A1 | 6/1994 |
| WO | WO 94/18855 A | 9/1994 |
| WO | WO9418855 | 9/1994 |
| WO | WO 9418855 A1 | 9/1994 |
| WO | WO 95/03050 A2 | 2/1995 |
| WO | WO9503785 A1 | 2/1995 |
| WO | WO 95/17104 A | 6/1995 |
| WO | WO9517418 A2 | 6/1995 |
| WO | WO9517829 | 7/1995 |
| WO | WO9527408 A1 | 10/1995 |
| WO | WO 95/31547 A1 | 11/1995 |
| WO | WO 95/33385 A1 | 12/1995 |
| WO | WO 96/00509 A1 | 1/1996 |
| WO | WO 96/08976 A1 | 3/1996 |
| WO | WO 96/08979 A1 | 3/1996 |
| WO | WO9617527 A1 | 6/1996 |
| WO | WO 96/22701 A1 | 8/1996 |
| WO | WO 96/26650 A1 | 9/1996 |
| WO | WO9626649 A1 | 9/1996 |
| WO | WO 96/39048 A1 | 12/1996 |
| WO | WO9700945 | 1/1997 |
| WO | WO 97/15200 A1 | 5/1997 |
| WO | WO 97/15201 A1 | 5/1997 |
| WO | WO9741839 A1 | 11/1997 |
| WO | WO9742333 | 11/1997 |
| WO | WO 97/48288 A1 | 12/1997 |
| WO | WO 98/02050 A1 | 1/1998 |
| WO | WO 98/03082 | 1/1998 |
| WO | WO9804156 | 2/1998 |
| WO | WO9806436 A2 | 2/1998 |
| WO | WO 98/14179 A1 | 4/1998 |
| WO | WO9820753 A1 | 5/1998 |
| WO | WO9823166 A1 | 6/1998 |
| WO | WO 98/27832 | 7/1998 |
| WO | WO9827832 | 7/1998 |
| WO | WO 98/39350 A1 | 9/1998 |
| WO | WO9841096 | 9/1998 |
| WO | WO9849905 A3 | 2/1999 |
| WO | WO 99/15032 A1 | 4/1999 |
| WO | WO 99/20127 A1 | 4/1999 |
| WO | WO 99/27803 | 6/1999 |
| WO | WO 99/27804 | 6/1999 |
| WO | WO 99/30577 A1 | 6/1999 |

(56) References Cited

FOREIGN PATENT DOCUMENTS

| | | |
|---|---|---|
| WO | WO 99/30578 A1 | 6/1999 |
| WO | WO9930576 | 6/1999 |
| WO | WO9934689 A1 | 7/1999 |
| WO | WO9938390 A1 | 8/1999 |
| WO | WO 99/43312 A1 | 9/1999 |
| WO | WO9949724 A1 | 10/1999 |
| WO | WO9952556 A1 | 10/1999 |
| WO | WO 99/55320 A | 11/1999 |
| WO | WO0001253 A1 | 1/2000 |
| WO | WO 00/11967 A1 | 3/2000 |
| WO | WO 00/15049 A1 | 3/2000 |
| WO | WO 00/15050 A1 | 3/2000 |
| WO | WO 00/24272 A | 5/2000 |
| WO | WO0036933 | 6/2000 |
| WO | WO 00/43416 A1 | 7/2000 |
| WO | WO 00/45651 A | 8/2000 |
| WO | WO 00/49036 A1 | 8/2000 |
| WO | WO 00/49052 A1 | 8/2000 |
| WO | WO 00/49895 A1 | 8/2000 |
| WO | WO0056175 | 9/2000 |
| WO | WO0056176 A1 | 9/2000 |
| WO | WO 00/57725 A1 | 10/2000 |
| WO | WO 00/57726 A | 10/2000 |
| WO | WO 00/61759 A1 | 10/2000 |
| WO | WO0057726 | 10/2000 |
| WO | WO 00/64279 A1 | 11/2000 |
| WO | WO0064278 | 11/2000 |
| WO | WO0069282 A1 | 11/2000 |
| WO | WO0069283 A1 | 11/2000 |
| WO | WO0072701 A1 | 12/2000 |
| WO | WO 01/10241 A2 | 2/2001 |
| WO | WO0106872 A1 | 2/2001 |
| WO | WO0111988 A2 | 2/2001 |
| WO | WO0113740 A1 | 3/2001 |
| WO | WO0113741 A1 | 3/2001 |
| WO | WO01013742 A1 | 3/2001 |
| WO | WO 01/28357 A | 4/2001 |
| WO | WO0128357 | 4/2001 |
| WO | WO0128362 A1 | 4/2001 |
| WO | WO0128503 A1 | 4/2001 |
| WO | WO0140902 | 6/2001 |
| WO | WO 01/52671 A2 | 7/2001 |
| WO | WO 01/60842 A | 8/2001 |
| WO | WO 01/70049 A | 9/2001 |
| WO | WO0176389 A1 | 10/2001 |
| WO | WO0180666 A1 | 11/2001 |
| WO | WO 02/05660 A | 1/2002 |
| WO | WO 02/05661 A2 | 1/2002 |
| WO | WO0200041 | 1/2002 |
| WO | WO 02/11716 A | 2/2002 |
| WO | WO 02/067702 | 2/2002 |
| WO | WO 02/34073 A | 5/2002 |
| WO | WO 02/058482 A | 8/2002 |
| WO | WO 02/067699 A1 | 9/2002 |
| WO | WO 02/067700 A | 9/2002 |
| WO | WO 02/080850 A2 | 10/2002 |
| WO | WO02076433 | 10/2002 |
| WO | WO02080704 A1 | 10/2002 |
| WO | WO 02/087357 A1 | 11/2002 |
| WO | WO 02/092106 A1 | 11/2002 |
| WO | WO02087358 | 11/2002 |
| WO | WO 02087358 A1 | 11/2002 |
| WO | WO 02087359 | 11/2002 |
| WO | WO 02/096449 A | 12/2002 |
| WO | WO 02/100192 A1 | 12/2002 |
| WO | WO 03/007734 | 1/2003 |
| WO | WO03011306 A1 | 2/2003 |
| WO | WO 03/022208 A | 3/2003 |
| WO | WO 03/024600 A1 | 3/2003 |
| WO | WO 03/047502 A1 | 6/2003 |
| WO | WO 03/063613 A1 | 8/2003 |
| WO | WO03063614 A1 | 8/2003 |
| WO | WO 03/076453 A1 | 9/2003 |
| WO | WO 03/076454 A1 | 9/2003 |
| WO | WO03075661 A1 | 9/2003 |
| WO | WO 03/087116 A1 | 10/2003 |
| WO | WO030103415 A1 | 12/2003 |
| WO | WO2004000045 A2 | 12/2003 |
| WO | WO 2004/003236 A1 | 1/2004 |
| WO | WO 2004/005227 A1 | 1/2004 |
| WO | WO 2004/032950 A1 | 4/2004 |
| WO | WO2004037191 | 5/2004 |
| WO | WO2004041003 A1 | 5/2004 |
| WO | WO 2004/045541 | 6/2004 |
| WO | WO 2004/047663 A | 6/2004 |
| WO | WO2004050104 | 6/2004 |
| WO | WO 2004/073419 | 9/2004 |
| WO | WO 2004/078302 A | 9/2004 |
| WO | WO 2004/082664 A | 9/2004 |
| WO | WO2004075664 A1 | 9/2004 |
| WO | WO 2004/086885 A1 | 10/2004 |
| WO | WO 2004/089343 A | 10/2004 |
| WO | WO2004084642 A1 | 10/2004 |
| WO | WO2004084655 A1 | 10/2004 |
| WO | WO2004087096 A1 | 10/2004 |
| WO | WO 2004089113 A | 10/2004 |
| WO | WO 2004/096192 A1 | 11/2004 |
| WO | WO2004096175 A2 | 11/2004 |
| WO | WO 2004/107872 A1 | 12/2004 |
| WO | WO 2004/108767 A2 | 12/2004 |
| WO | WO 2004/110168 A1 | 12/2004 |
| WO | WO 2005/000325 A | 1/2005 |
| WO | WO2005001145 A1 | 1/2005 |
| WO | WO2005002536 | 1/2005 |
| WO | WO2005004636 A2 | 1/2005 |
| WO | WO2005004637 A1 | 1/2005 |
| WO | WO 2005/009147 A | 2/2005 |
| WO | WO 2005/013720 A2 | 2/2005 |
| WO | WO 2005/013728 A | 2/2005 |
| WO | WO 2005/013957 A | 2/2005 |
| WO | WO 2005/016022 A1 | 2/2005 |
| WO | WO2005009148 A2 | 2/2005 |
| WO | WO2005011639 | 2/2005 |
| WO | WO2005013728 A1 | 2/2005 |
| WO | WO2005014839 A2 | 2/2005 |
| WO | WO2005020721 A1 | 3/2005 |
| WO | WO 2005/033125 A2 | 4/2005 |
| WO | WO 2005048743 | 6/2005 |
| WO | WO 2005/063156 A | 7/2005 |
| WO | WO2005063200 | 7/2005 |
| WO | WO 2005/070390 A | 8/2005 |
| WO | WO 2005/072717 A | 8/2005 |
| WO | WO 2005/082170 A1 | 9/2005 |
| WO | WO 2005/082850 A1 | 9/2005 |
| WO | WO 2005/086646 A2 | 9/2005 |
| WO | WO 2005/089483 | 9/2005 |
| WO | WO 2005/089724 A | 9/2005 |
| WO | WO2005082417 | 9/2005 |
| WO | WO2005089483 A2 | 9/2005 |
| WO | WO 2005/094812 A | 10/2005 |
| WO | WO2005094611 | 10/2005 |
| WO | WO 2005/103304 A1 | 11/2005 |
| WO | WO2005102071 A1 | 11/2005 |
| WO | WO 2005105049 A2 | 11/2005 |
| WO | WO 2005/118619 A | 12/2005 |
| WO | WO2005115169 A1 | 12/2005 |
| WO | WO2005117608 A1 | 12/2005 |
| WO | WO2006009425 A2 | 1/2006 |
| WO | WO 2006/012763 A1 | 2/2006 |
| WO | WO 2006/015764 A | 2/2006 |
| WO | WO 2006/020686 A1 | 2/2006 |
| WO | WO 2006/020754 A1 | 2/2006 |
| WO | WO 2006/021007 A | 2/2006 |
| WO | WO2006015764 A1 | 2/2006 |
| WO | WO2006015880 | 2/2006 |
| WO | WO 2006/026298 A2 | 3/2006 |
| WO | WO 2006/027796 A | 3/2006 |
| WO | WO 2006/032967 A2 | 3/2006 |
| WO | WO 2006/033496 A1 | 3/2006 |
| WO | WO2006027796 | 3/2006 |
| WO | WO 2006/036418 A2 | 4/2006 |
| WO | WO 2006/038221 A | 4/2006 |
| WO | WO 2006/041216 A | 4/2006 |
| WO | WO 2006/043305 A1 | 4/2006 |

(56) References Cited

FOREIGN PATENT DOCUMENTS

| | | |
|---|---|---|
| WO | WO06041668 A1 | 4/2006 |
| WO | WO2006039768 | 4/2006 |
| WO | WO 2006/045742 A2 | 5/2006 |
| WO | WO2006045742 | 5/2006 |
| WO | WO2006065738 | 6/2006 |
| WO | WO 2006/072921 A | 7/2006 |
| WO | WO 2006/074278 A | 7/2006 |
| WO | WO2006072879 | 7/2006 |
| WO | WO2006072920 | 7/2006 |
| WO | WO2006072921 | 7/2006 |
| WO | WO 2006/083951 A | 8/2006 |
| WO | WO 2006/093229 A1 | 9/2006 |
| WO | WO 2006/093848 | 9/2006 |
| WO | WO 2006/102451 | 9/2006 |
| WO | WO2006093566 | 9/2006 |
| WO | WO2006097947 | 9/2006 |
| WO | WO2006101706 | 9/2006 |
| WO | WO 2006/112686 | 10/2006 |
| WO | WO 2006/118137 A | 11/2006 |
| WO | WO 2006/127935 | 11/2006 |
| WO | WO2006115680 | 11/2006 |
| WO | WO2006115970 | 11/2006 |
| WO | WO2006116009 | 11/2006 |
| WO | WO2006117029 | 11/2006 |
| WO | WO2006117602 | 11/2006 |
| WO | WO 2006/138512 | 12/2006 |
| WO | WO2006128269 | 12/2006 |
| WO | WO2006128493 | 12/2006 |
| WO | WO 2007/006320 A | 1/2007 |
| WO | WO2007001501 | 1/2007 |
| WO | WO2007011870 | 1/2007 |
| WO | WO 2007/022069 | 2/2007 |
| WO | WO2007014879 | 2/2007 |
| WO | WO 2007/027984 A | 3/2007 |
| WO | WO 2007/033064 A | 3/2007 |
| WO | WO 2007/033066 | 3/2007 |
| WO | WO2007027095 | 3/2007 |
| WO | WO2007027984 | 3/2007 |
| WO | WO2007033067 | 3/2007 |
| WO | WO 2007/038919 A1 | 4/2007 |
| WO | WO 2007/039294 A2 | 4/2007 |
| WO | WO 2007/040345 A1 | 4/2007 |
| WO | WO 2007/041035 A2 | 4/2007 |
| WO | WO 2007/041830 A1 | 4/2007 |
| WO | WO 2007/043796 A1 | 4/2007 |
| WO | WO 2007/043810 A1 | 4/2007 |
| WO | WO 2007/044526 A2 | 4/2007 |
| WO | WO 2007/046642 A1 | 4/2007 |
| WO | WO 2007/049873 A1 | 5/2007 |
| WO | WO 2007/051485 A1 | 5/2007 |
| WO | WO 2007/051542 A2 | 5/2007 |
| WO | WO 2007/051546 A1 | 5/2007 |
| WO | WO 2007/051547 A2 | 5/2007 |
| WO | WO 2007/058384 A1 | 5/2007 |
| WO | WO 2007/059953 A1 | 5/2007 |
| WO | WO 2007/061182 A1 | 5/2007 |
| WO | WO 2007/061243 A1 | 5/2007 |
| WO | WO 2007/061691 A2 | 5/2007 |
| WO | WO 2007/061888 A2 | 5/2007 |
| WO | WO 2007/062087 A2 | 5/2007 |
| WO | WO 2007/062266 A2 | 5/2007 |
| WO | WO2007054274 | 5/2007 |
| WO | WO 2007057924 A1 | 5/2007 |
| WO | WO2007062087 | 5/2007 |
| WO | WO 2007/063075 A1 | 6/2007 |
| WO | WO 2007/064505 A1 | 6/2007 |
| WO | WO 2007/064519 A1 | 6/2007 |
| WO | WO 2007/064521 A2 | 6/2007 |
| WO | WO 2007/064601 A2 | 6/2007 |
| WO | WO 2007/065076 A2 | 6/2007 |
| WO | WO 2007/066178 A2 | 6/2007 |
| WO | WO 2007/066192 A2 | 6/2007 |
| WO | WO 2007/066233 A2 | 6/2007 |
| WO | WO 2007/066234 A2 | 6/2007 |
| WO | WO 2007/066928 A1 | 6/2007 |
| WO | WO 2007/066991 A1 | 6/2007 |
| WO | WO 2007/067340 A1 | 6/2007 |
| WO | WO 2007/068403 A2 | 6/2007 |
| WO | WO 2007/070754 A2 | 6/2007 |
| WO | WO 2007/071037 A1 | 6/2007 |
| WO | WO 2007/073021 A1 | 6/2007 |
| WO | WO 2007070164 | 6/2007 |
| WO | WO 2007/073838 A1 | 7/2007 |
| WO | WO 2007/073909 A1 | 7/2007 |
| WO | WO 2007/075433 A2 | 7/2007 |
| WO | WO 2007/076024 A2 | 7/2007 |
| WO | WO 2007/076025 A2 | 7/2007 |
| WO | WO 2007/076170 A2 | 7/2007 |
| WO | WO 2007/076425 A2 | 7/2007 |
| WO | WO 2007/076856 A1 | 7/2007 |
| WO | WO 2007/076857 A1 | 7/2007 |
| WO | WO 2007/077210 A1 | 7/2007 |
| WO | WO 2007/078293 A | 7/2007 |
| WO | WO 2007/078895 A2 | 7/2007 |
| WO | WO 2007/079180 A2 | 7/2007 |
| WO | WO 2007/079333 A2 | 7/2007 |
| WO | WO 2007/081115 A1 | 7/2007 |
| WO | WO 2007/083858 A1 | 7/2007 |
| WO | WO 2007/084185 A | 7/2007 |
| WO | WO 2007/084290 A | 7/2007 |
| WO | WO 2007/084587 A2 | 7/2007 |
| WO | WO 2007/084617 A2 | 7/2007 |
| WO | WO 2007/084964 A2 | 7/2007 |
| WO | WO 2007/084983 A2 | 7/2007 |
| WO | WO2007078293 | 7/2007 |
| WO | WO2007084185 | 7/2007 |
| WO | WO2007085593 | 8/2007 |
| WO | WO2007098092 | 8/2007 |
| WO | WO2007107596 | 9/2007 |
| WO | WO 2007/068346 A1 | 11/2007 |
| WO | WO 2007/121604 | 11/2007 |
| WO | WO 2008/042661 A | 4/2008 |
| WO | WO 2008/049256 | 5/2008 |
| WO | WO 2008/049258 | 5/2008 |

OTHER PUBLICATIONS

Schiffman, S. S. et al., "Effect of repeated presentation on sweetness intensity of binary and ternary mixtures of sweeteners", *Chemical Senses* 2003, vol. 28, pp. 219-229.

Hirata, K. et al. "Analysis of Stevia Glycosides in Stevia Products of Natural Sweetening and Evaluation of their Chemical Quality", Ann. Rep. Tokyo Metr. Res. Lab. P.H., vol. 53, pp. 108-112, 2002.

Morita Kagaku Kogyo Co., Ltd., The rebaudio A9 series, http://www.morita-kagaku-kogyo.co.jp/a9.htm.

Morita Kagaku Kogyo Co., Ltd., The rebaudio J series, http://www.morita-kagaku-kogyo.co.jp/j.htm.

US 6,933,480, 8/2005, Kawahara et al. (withdrawn).

Disclosure Under 37 CFR 1.56 dated Dec. 18, 2008, filed for U.S. Appl. No. 11/556,062.

Annual Statistic Report on Soft Drinks, p. 1, 4, 5, 20 and 21 (Jun. 2000).

Annual Statistic Report on Soft Drinks, p. 118, 119, 220, and 221 (May 2005).

"Battle for Brazil, Brazil: Diet Pepsi, Diet Coke to compete since govt lifted ban on artificial sweeteners," Beverage Industry, Mar. 1989, pp. 37-38.

"Beverages," New Food Products in Japan, Jun. 1992.

"Beverages: Striker Grapefruit Taste Slightly Carbonated Type from Yakult Honsha," Com-line Consumer Goods, Apr. 15, 1999, pp. 990415100032.

"Brazil okays diet soft drinks, Brazil: Ministry of Health to allow soft drink mfrs to mkt diet versions of beverages," Chemical Week, Aug. 3, 1988, pp. 44.

Davidson, et al., "Pharmacotherapeutics for osteoporosis prevention and treatment," Journal of Midwifery & Women's Health, Elsevier, vol. 48, No. 1, Jan. 2003, pp. 39-52.

"High-power sweeteners from the stevia plant," Chemical Week, Nov. 14, 1984, pp. 42-461.

Pion Japanese internet publication, http://drink.vis.ne.jp/drink_data/syousai/pion-momo.htm.

(56) References Cited

OTHER PUBLICATIONS

Kyun Japanese internet publication, http://www2.plala.or.jp/kimyouan/trinken/50-99/92kyunn.htm.
International Search Report and Written Opinion for PCT/US08063843.
International Search Report and Written Opinion for PCTUS06044575.
International Search Report and Written Opinion for PCTUS06044576.
International Search Report and Written Opinion for PCTUS06044707.
International Search Report and Written Opinion for PCTUS06044723.
International Search Report and Written Opinion for PCTUS06044725.
International Search Report and Written Opinion for PCTUS06044726.
International Search Report and Written Opinion for PCTUS06044797.
International Search Report and Written Opinion for PCTUS07083374.
International Search Report and Written Opinion for PCTUS07083375.
International Search Report and Written Opinion for PCTUS07083376.
International Search Report and Written Opinion for PCTUS07083378.
International Search Report and Written Opinion for PCTUS07083379.
Japan Chemical Week, Apr. 17, 1986 (860417), 27(1359), p. 4, 6.
Kanemaru, et al, "Enhancement of Sucrose Sweeteners with Soluble Starch in Humans," Chem. Senses, 27:67-72 (2002).
Kawakami, A. et al., "Taste evaluations of angiotensin I converting enzyme inhibitors, Leu-Lys-Tyr analogues," International Food Information Service (IFIS), Frankfurt-Main, DE; 1995, vol. 59, No. 4, p. 709 (Abstract).
Kolb, et al., "Analysis of Sweet Diterpene glycosides from *Stevia rebaudiana*: Improved HPLC Method," J. Agric. Food Chem., vol. 49, No. 10 (2001).
Meyer, S., "Investigating Taste Interactions," Fruit Processing, Schoenborn, DE, vol. 12, No. 5, May 2002, pp. 224-227.
News Release, Mi Kuni Coca-Cola Bottling Co., Ltd, "Powerade," Apr. 18, 2005, at www.cocacola.co.jp/corporate/release/pdf/437.pdf.
Pereira, J. V., "Plant and plant-derived compounds employed in prevention of the osteoporosis," ACTA Farm Bonaerense, vol. 21, No. 3, 2002, pp. 223-234.
Sardesai, V.M., et al., "Natural and Synthetic Intense Sweeteners," Journal of Nutritional Biochemistry, Butterworth Publishers, Stoneham, GB, vol. 2, No. 5, May 1991, p. 237, col. 2.
Schiffman, S.S., et al., "Bitterness of sweeteners as a function of concentration," US National Library of Medicine (NLM), Bethesda, MD, US; 1995, Absract.
Schiffman, S.S., et al., "Investigation of synergism in binary mixtures of sweeteners," Brain Research Bulletin, Elsevier Science Ltd., Oxford, GB, vol. 38, No. 2, 1995, pp. 105-120.
Schiffman, S.S., et al., "Synergism among ternary mixtures of fourteen sweeteners," Chemical Sense, IRL Press, Oxford, GB, vol. 25, 2000, pp. 131-140.
Sherma, Joseph, "Quantitative TLC determination of stevioside and rebaudioside A in beverages," Journal of Liquid Chromatography, 1992, 15(17), 2981-8.
Tadhani, M., et al., "Preliminary studies on *Stevi rebaudiana* leaves: proximal composition, mineral analysis and phytochemical screening," J. Med. Sci., vol. 6, No. 3, 2006, pp. 321-326.
Yoshikawa, S., et al., "Taste of components of stevioside," International Food Information Service (IFIS), Frankfurt-Main, DE. (Abstract).
Sasaki, Kazuhito, "Application of Stevia Sweetener to Soft Drinks," *New Food Ind.*, 1983, pp. 38-43, vol. 25 No. 4, Sanyo Kokusaku Pulp Co. Ltd., Japan.

Kohda, Hiroshi, et al., "New Sweet Diterpene Glucosides from *Stevia rebaudiana*," Phytochemistry, 1976, pp. 981-983, vol. 15 No. 6, School of Medicine, Hiroshima Univ., Hiroshima, Japan.
Nabors, Lyn O'Brien, et al., "Alternative Sweeteners," *Food Science and Technology*, 1985, pp. 295-307, vol. 17, Marcel Dekker, Inc., New York, NY, USA.
"SteviaClear™ Liquid Stevia," Jun. 2005, Advertisement.
Abudula, Reziwanggu, et al., "Rebaudioside A Potently Stimulates insulin Secretion from Isolated Mice Islets: Studies on the Dose-Glucose-, and Calcium-Dependency," Metabolism, Oct. 2004, vol. 53 No. 10, Arhus University Hospital, Arhus, Denmark.
Mizutani, Kenji, et al., "Use of *Stevia rebaudiana* Sweeteners in Japan," *Stevia: The Genus Stevia*, 2002, pp. 178-195, A. Douglas Kinghorn, ed., Taylor and Francis, Inc., New York, NY, USA.
Kim, Jinwoong, et al., "Use of Stevioside and Cultivation of *Stevia rebaudiana* in Korea," *Stevia: The Genus Stevia*, 2002, pp. 196-202, A. Douglas Kinghorn, ed., Taylor and Francis, Inc., New York, NY, USA.
Chang, Shin S., et al., "Stability Studies of Stevioside and Rebaudioside A in Carbonated Beverages," J. Agri. Food. Chem., 1983, pp. 409-412., vol. 31, American Chemical Society, USA.
Goettemoeller, Jeffrey, "Stevia Sweet Recipes: Sugar Free—Naturally!" 1998, pp. 1-17, Vital Health Publishing, Bloomingdale, Illinois, USA.
Depuydt, Rita, "Baking with Stevia 11," 1998, pp. 5-6, 9-10, 15, 104, Sun Coast Enterprises, Oak View, California, USA.
The Ministry of Health and Welfare, Food Chemical Department, "List of Food Additives excluding chemical synthetics," 1989, The Government of Japan, Tokyo, Japan.
Geuns, Jan M. C., "Review: The Safety of Stevioside used as a Sweetener," in Proceedings of the first symposium, 'The Safety of Stevioside,' 2004, pp. 85-127, Laboratory of Functional Biology, KULeuven, Leuven, Belgium.
Food Standards Australia New Zealand, "Draft Assessment Report, Application A540, Steviol Glycosides as Intense Sweeteners," 2007, Canberra, Australia.
Sunrider Product Catalog, Apr. 1994, pp. 3, 5, The Sunrider Corporation, Torrance, CA, USA.
Sunrider Product Catalog, Apr. 1999, pp. 1-2, The Sunrider Corporation, Torrance, CA, USA.
Sunrider Product Catalog, Apr. 2000, pp. 1-2, The Sunrider Corporation, Torrance, CA, USA.
Sunrider Product Catalog, Jan. 2001, pp. 1, 12-13, The Sunrider Corporation, Torrance, CA, USA.
Sunrider Product Catalog, Jan. 2002, pp. 6-7, 18-19, The Sunrider Corporation, Torrance, CA, USA.
Sunrider Product Catalog, May 2003, pp. 10-11, 18-19, The Sunrider Corporation, Torrance, CA, USA.
Sunrider Product Catalog, Feb. 2005, pp. 7-8, 21-22, The Sunrider Corporation, Torrance, CA, USA.
Sunrider Product Catalog, 2006, pp. 7-8, 21-22, The Sunrider Corporation, Torrance, CA, USA.
Sunrider Product Catalog, 2007, pp. 8-9, 14-15, The Sunrider Corporation, Torrance, CA, USA.
The Sunrider Corporation, "Delicious Nutritious Whole Food Sunrider Recipes," 2004, http://healthregeneration.com/recipes.html.
The Sunrider Corporation, VitaFruit product advertising flyer, 1994, Torrance, CA, USA.
Sunwriter Newsletter, "The Truth About Trusweet," Jul. 1983, p. 2, The Sunrider Corporation, Torrance, CA, USA.
Sunwriter Newsletter, "The Truth About Trusweet," Apr. 1984, p. 2, The Sunrider Corporation, Torrance, CA, USA.
The SunSpot Newsletter, "SunCare is Available," May 1985, p. 2, The Sunrider Corporation, Torrance, CA, USA.
The SunSpot Newsletter, Jan. 1988, pp. 1-2, The Sunrider Corporation, Torrance, CA, USA.
The SunSpot Newsletter, Nov. 1993, pp. 1-2, vol. 11, No. 11, The Sunrider Corporation, Torrance, CA, USA.
The SunSpot Newsletter, Dec. 1993, pp. 1-2, vol. 11, No. 12, The Sunrider Corporation, Torrance, CA, USA.
The SunSpot Newsletter, Mar. 1995, pp. 1, 3, vol. 13, No. 3, The Sunrider Corporation, Torrance, CA, USA.

(56) References Cited

OTHER PUBLICATIONS

Sunwriter Newsletter, "Sunectar," Holiday Issue 1995, vol. 12, No. 5, The Sunrider Corporation, Torrance, CA, USA.
Sunwriter Newsletter, "Sunnydew," May/Jun. 1996, vol. 13, No. 3, The Sunrider Corporation, Torrance, CA, USA.
Sunwriter Newsletter, Sep./Oct. 1996, vol. 13, No. 5, The Sunrider Corporation, Torrance, CA, USA.
The SunSpot Newsletter, "VitaSpray," Sep. 1996, vol. 14, No. 9, The Sunrider Corporation, Torrance, CA, USA.
The SunSpot Newsletter, pp. 1-2, Nov. 1996, vol. 14, No. 10, The Sunrider Corporation, Torrance, CA, USA.
The SunSpot Newsletter, pp. 1-2, Aug. 1997, vol. 15, No. 8, The Sunrider Corporation, Torrance, CA, USA.
The SunSpot Newsletter, pp. 1-2, May 1998, vol. 16, No. 5, The Sunrider Corporation, Torrance, CA, USA.
The SunSpot Newsletter, pp. 1-3, Jul. 1998, vol. 16, No. 7, The Sunrider Corporation, Torrance, CA, USA.
The SunSpot Newsletter, pp. 1-2, Oct. 1998, vol. 16, No. 10, The Sunrider Corporation, Torrance, CA, USA.
The SunSpot Newsletter, pp. 1, 4, Mar. 1999, vol. 18, No. 3, The Sunrider Corporation, Torrance, CA, USA.
The SunSpot Newsletter, pp. 1-2, Jan. 1999, vol. 18, No. 1, The Sunrider Corporation, Torrance, CA, USA.
Sunwriter Newsletter, pp. 12, 14, 1999, vol. 16, No. 1, The Sunrider Corporation, Torrance, CA, USA.
The SunSpot Newsletter, pp. 1-2, Mar. 2000, vol. 19, No. 3, The Sunrider Corporation, Torrance, CA, USA.
The SunSpot Newsletter, pp. 1, 4, Oct. 2000, vol. 19, No. 10, The Sunrider Corporation, Torrance, CA, USA.
The SunSpot Newsletter, pp. 1-2, Apr. 2001, vol. 20, No. 4, The Sunrider Corporation, Torrance, CA, USA.
The SunSpot Newsletter, pp. 1-2, Jun. 2002, vol. 21, No. 6, The Sunrider Corporation, Torrance, CA, USA.
The SunSpot Newsletter, pp. 1-2, Oct. 2002, vol. 21, No. 10, The Sunrider Corporation, Torrance, CA, USA.
Director Update Newsletter, "Sunrider VitaFruit Liquid Concentrate," Nov. 1993, The Sunrider Corporation, Torrance, CA, USA.
Director Update Newsletter, Dec. 1993, The Sunrider Corporation, Torrance, CA, USA.
Director Update Newsletter, Jun. 1994, The Sunrider Corporation, Torrance, CA, USA.
Director Update Newsletter, Dec. 1994, The Sunrider Corporation, Torrance, CA, USA.
Director Update Newsletter, Apr. 1995, The Sunrider Corporation, Torrance, CA, USA.
Director Update Newsletter, Jun. 1995, The Sunrider Corporation, Torrance, CA, USA.
Director Update Newsletter, Jul. 1995, The Sunrider Corporation, Torrance, CA, USA.
Director Update Newsletter, Nov. 1995, The Sunrider Corp., Torrance, CA, USA.
Director Update Newsletter, Dec. 1995, The Sunrider Corporation, Torrance, CA, USA.
Director Update Newsletter, Feb. 1996, The Sunrider Corporation, Torrance, CA, USA.
Director Update Newsletter, May 1996, The Sunrider Corporation, Torrance, CA, USA.
Director Update Newsletter, Jun. 1996, The Sunrider Corporation, Torrance, CA, USA.
Director Update Newsletter, Jul. 1996, The Sunrider Corporation, Torrance, CA, USA.
Director Update Newsletter, Aug. 1996, The Sunrider Corporation, Torrance, CA, USA.
Director Update Newsletter, Sep. 1996, The Sunrider Corporation, Torrance, CA, USA.
Director Update Newsletter, Nov. 1996, The Sunrider Corporation, Torrance, CA, USA.
Director Update Newsletter, Feb. 2000, The Sunrider Corporation, Torrance, CA, USA.
Director Update Newsletter, Nov. 2001, The Sunrider Corporation, Torrance, CA, USA.
Director Update Newsletter, Aug. 2003, The Sunrider Corporation, Torrance, CA, USA.
Director Update Newsletter, Nov. 2004, The Sunrider Corporation, Torrance, CA, USA.
Director Update Newsletter, Aug. 2005, The Sunrider Corporation, Torrance, CA, USA.
The Sunrider Corporation, Trusweet Extract product packaging, 1982, Torrance, CA, USA.
The Sunrider Corporation, Sunectar Dietary Supplement product label, 1995, 1996, 2002, 2003, Torrance, CA, USA.
Sunrider International, SunCare Natural Facial Masque product label, 1989, 1990, 1991, 1992, 1994, 1995, Torrance, CA, USA.
Sunrider International, SunCare Herbal Skincare product label, 1991, 1993, 1992, 1995, Torrance, CA, USA.
The Sunrider Corporation, VitaFruit Lemon Liquid Herb Fruit Concentrate product label, 1993, 1994, 1995, 1996, 1997, 2000, 2001, 2002, 2003, 2006, Torrance, CA, USA.
The Sunrider Corporation, VitaSpray Dietary Supplement product label, Dec. 2002, Torrance, CA, USA.
The Sunrider Corporation, Sunnydew Dietary Supplement product label, Jun. 1999, 2002, 2003, 2006, Torrance, CA, USA.
The Sunrider Corporation, SunSmile Tabs product label, 1998, Torrance, CA, USA.
The Sunrider Corporation, Herbal Cal Tab Dietary Supplement product label, 1999, 2000, 2001, 2002, 2003, Torrance, CA, USA.
The Sunrider Corporation, Calli product label, 1983, Torrance, CA, USA.
The Sunrider Corporation, Alpha 20C product label, 1999, 2000, Torrance, CA, USA.
The Sunrider Corporation, Sunrise product label, 1999.
The Sunrider Corporation, Evergreen product label, 2000.
The Sunrider Corporation, Quinary product label, year not indicated.
The Sunrider Corporation, Fortune Delight product label, Mar. 2003, Torrance, CA, USA.
The Sunrider Corporation, NuPlus product label, 2002, 2003, Torrance, CA, USA.
Adechy, Miriam, "International Search Report and Written Opinion of the International Searching Authority," Apr. 11, 2007, PCT/US2006/044574, European Patent Office, Rijswijk, The Netherlands.
Georgopoulos, N., "International Search Report and Written Opinion of the International Searching Authority," Mar. 14, 2007, PCT/US2006/044518, European Patent Office, Rijswijk, The Netherlands.
Couzy, Francois, "International Search Report and Written Opinion of the International Searching Authority," Mar. 22, 2007, PCT/US2006/044724, European Patent Office, Rijswijk, The Netherlands.
Couzy, Francois, "International Search Report and Written Opinion of the International Searching Authority," Jun. 22, 2007, PCT/US2006/044802, European Patent Office, Rijswijk, The Netherlands.
Popa, Marian, "International Search Report and Written Opinion of the International Searching Authority," May 11, 2007, PCT/US2006/044592, European Patent Office, Rijswijk, The Netherlands.
Ipinazar, Paula, "Partial International Search Report of the International Searching Authority," Apr. 2007, PCT/US2006/044600, European Patent Office, Rijswijk, The Netherlands.
Heirbaut, Marc, "International Search Report and Written Opinion of the International Searching Authority," Oct. 31, 2007, PCT/US2006/044513, European Patent Office, Rijswijk, The Netherlands.
Smeets, Dieter, "International Search Report and Written Opinion of the International Searching Authority," Apr. 10, 2007, PCT/US2006/044785, European Patent Office, Rijswijk, The Netherlands.
Couzy, Francois, "International Search Report and Written Opinion of the International Searching Authority," Mar. 23, 2007, PCT/US2006/044727, European Patent Office, Rijswijk, The Netherlands.
Couzy, Francois, "International Search Report and Written Opinion of the International Searching Authority," Mar. 21, 2007, PCT/US2006/044591, European Patent Office, Rijswijk, The Netherlands.
Georgopoulos, N., "International Search Report and Written Opinion of the International Searching Authority," Jun. 13, 2007, PCT/US2006/044599, European Patent Office, Rijswijk, The Netherlands.

(56) References Cited

OTHER PUBLICATIONS

Popa, Marian, "International Search Report and Written Opinion of the International Searching Authority," May 4, 2007, PCT/US2006/044577, European Patent Office, Rijswijk, The Netherlands.
Popa, Marian, "International Search Report and Written Opinion of the International Searching Authority," Mar. 15, 2007, PCT/US2006/044783, European Patent Office, Rijswijk, The Netherlands.
Donovan-Beerman, T., "International Search Report and Written Opinion of the International Searching Authority," Mar. 30, 2007, PCT/US2006/044573, European Patent Office, Rijswijk, The Netherlands.
Popa, Marian, "International Search Report and Written Opinion of the International Searching Authority," Mar. 16, 2007, PCT/US2006/044705, European Patent Office, Rijswijk, The Netherlands.
Groh, Bjorn, "International Search Report and Written Opinion of the International Searching Authority," Oct. 24, 2007, PCT/US2006/044803, European Patent Office, Rijswijk, The Netherlands.
Smeets, Dieter, "International Search Report and Written Opinion of the International Searching Authority," Apr. 3, 2007, PCT/US2006/044590, European Patent Office, Rijswijk, The Netherlands.
Groh, Bjorn, "International Search Report and Written Opinion of the International Searching Authority," Apr. 16, 2007, PCT/US2006/044706, European Patent Office, Rijswijk, The Netherlands.
Couzy, Francois, "International Search Report and Written Opinion of the International Searching Authority," Apr. 13, 2007, PCT/US2006/044703, European Patent Office, Rijswijk, The Netherlands.
Rinaldi, Francesco, "International Search Report and Written Opinion of the International Searching Authority," Mar. 20, 2007, PCT/US2006/044798, European Patent Office, Rijswijk, The Netherlands.
Hartlieb, Ariane, "International Search Report and Written Opinion of the International Searching Authority," Aug. 21, 2007, PCT/US2006/044801, European Patent Office, Rijswijk, The Netherlands.
Hicks, K., et. al., "Phytosterols and Phytostanols: Functional Food Cholesterol Busters," Food Technology, Jan. 1, 2001, pp. 63-67, vol. 55, No. 1, Inst. of Food Technologists, Chicago, IL, USA.
Sardesai, V. M., et al., "Natural and Synthetic Intense Sweeteners," *Journal of Nutritional Biochemistry*, May 1991, pp. 236-244, vol. 2, No. 5, Butterworth Publishers, Stoneham, Great Britain.
Schiffman, S., et. al., "Investigation of Synergism in Binary Mixtures of Sweeteners,"*Brain Research Bulletin*, 1995, pp. 105-120, vol. 38, No. 2, XP002428872.
Moriyama, et al., "Soybean beta-conglycinin diet suppresses serun triglyceride levels in normal and genetically obese mice by induction of beta-oxidation, down regulation of fatty acid synthase, and inhibition of triglyceride absorption," *Bioscience, Biotechnology, and Biochemistry*, Dec. 2004, pp. 352-359, vol. 26, No. 6, XP018001511.
Nojiri, S., et al., "Determination of sugar alcohols in confectionaries by high-performance liquid chromatography after nitrobenzoylation," Journal of Chromatography, Sep. 29, 2000, pp. 195-200, vol. 893, No. 1, Elsevier Science Publishers, B.V., Amsterdam, The Netherlands.
Abad, M. J., et al., "Anti-Inflammatory Activity of two flavonoids from *Tanacetum microphyllum*," Journal of Natural Products, 1993, pp. 1164-1167, vol. 56, No. 7, Biosciences Information Service, Philadelphia, PA, USA.
Anon., "Sweet tasting amino acid, glycine, enhances flavor and provides functional properties," Food Processing USA, 1983, p. 90, vol. 44, No. 7, International Food Information Service, Frankfurt-Main, Germany.
Shamala, T. R., et al., "Honey—it is more than just sweet," Indian Food Industry, 1999, pp. 349-357, vol. 18, No. 6, Dept. of Food Microbiology, Central Food Technology, Research Institute, Mysore, India.
Rajbhandari, A., "The Flavonoids of *Stevia rebaudiana*," J. Nat. Prod., 1983, pp. 194-195, vol. 46, No. 2.
Geuns, Jan M. C., "Stevioside," Phytochemistry, Nov. 2003, pp. 913-921, vol. 64, No. 5, Pergamon Press, Great Britain.
Schiffman, S., et al., "Synergism among ternary mixtures of fourteen sweeteners," Chemical Senses, 2000, pp. 131-140, vol. 25, IRL Press, Oxford, Great Britain.
Franke, S. I. R., et al., "Influence of orange juice over the genotoxicity induced by alkylating agents: an in vivo analysis," Mutagenesis, Jun. 14, 2005, pp. 279-283, vol. 20, No. 4, IRL Press, Oxford, Great Britain.
Losada, M., et al., "Toward a healthier diet for the colon: The influence of fructooligosaccharides and lactobacilli on intestinal health," Jan. 2002, Biosciences Information Service, Philadelphia, PA, USA.
Grenby, T. H., "Intense Sweeteners for the Food Industry: An Overview," *Trends in Food Science and Technology*, Jan. 1991, pp. 2-6, vol. 2, No. 1, Elsevier Science Publishers, Great Britain.
N. N., "Rebaudioside A and Stevia Extract," retrieved from the Internet on Mar. 16, 2007, pp. 1-5, http://emperorsherbologist.com/rabaudioside_a.php.
Anon., "Sugar-free Cake Mix Preparation by combining maltoligosyl-sucrose, sorbitol, and Stevia extract with glycine and/or DL-alanine," WPI/Thomson, Nov. 10, 1981, XP002425501.
Schiffman, Susan S., et al., "Selective Inhibition of Sweetness by Na-PMP," Apr. 26, 1999, pp. 439-437, Oxford University Press.
Kinghorn, A. D. "Discovery of Terpenoid and Phenolic Sweeteners From Plants" 2002, vol. 74, No. 7, pp. 1169-1179.

* cited by examiner

CONDIMENTS WITH HIGH-POTENCY SWEETENER

RELATED APPLICATION DATA

The present application claims priority under 35 U.S.C. §119 to U.S. Provisional Application No. 60/739,302, entitled "Natural High-Potency Sweetener Compositions With Improved Temporal Profile And/Or Flavor Profile, Methods For Their Formulations, and Uses," filed on Nov. 23, 2005; U.S. Provisional Application No. 60/739,124, entitled "Synthetic Sweetener Compositions with Improved Temporal Profile and/or Flavor Profile, Methods for Their Formulation and Uses," filed on Nov. 23, 2005; and U.S. Provisional Application No. 60/805,216, entitled "Rebaudioside A composition and Method for Purifying Rebaudioside A," filed on Jun. 19, 2006. These applications are hereby incorporated by reference in their entirety.

FIELD OF THE INVENTION

The present invention relates generally to novel condiment compositions, including functional condiment compositions, comprising non-caloric or low-caloric natural and/or synthetic, high-potency sweeteners and methods for manufacture and use thereof. The present invention also relates to condiment compositions and methods that can improve the taste of condiment compositions comprising non-caloric or low-caloric natural and/or synthetic high-potency sweeteners by imparting a more sugar-like taste.

BACKGROUND OF THE INVENTION

The use of non-caloric high intensity sweeteners is increasing due to health concerns relating to increased levels of childhood obesity, type II diabetes, and related illnesses. Although natural caloric sweetener compositions such as sucrose, fructose, and glucose provide the most desirable taste to consumers, they are caloric. Therefore, alternative non-caloric or low-caloric sweeteners have been widely used as sugar or sucrose substitutes. However, these sucrose substitutes possess taste characteristics different than that of sugar (e.g. saccharin, aspartame, and sucralose) and exhibit undesirable taste characteristics (e.g., non-sugar like aftertastes).

Thus, there is need to provide a non-caloric or low-caloric condiments with a more sugar-like taste. High-potency sweeteners are generally non-caloric; however, they exhibit sweet tastes that have a different temporal profiles, maximal responses, flavor profiles, mouthfeels, and/or adaptation behaviors than that of sugar. For example, the sweet tastes of high-potency sweeteners are slower in onset and longer in duration than the sweet taste produced by sugar and thus change the taste balance of a food composition. Because of these differences, use of a high-potency sweetener to replace a bulk sweetener, such as sugar, in a food or beverage, causes an unbalanced temporal profile and/or flavor profile. In addition to the difference in temporal profile, high potency sweeteners generally exhibit (i) lower maximal response than sugar, (ii) off tastes including bitter, metallic, cooling, astringent, licorice-like taste, etc., and/or (iii) sweetness which diminishes on iterative tasting. It is well known to those skilled in the art of food/beverage formulation that changing the sweetener in a composition requires re-balancing of the flavor and other taste components (e.g., acidulants). If the taste profile of high-potency sweeteners could be modified to impart specific desired taste characteristics to be more sugar-like, the type and variety of compositions that may be prepared with that sweetener would be significantly expanded. Accordingly, it would be desirable to selectively modify the taste characteristics of high-potency sweeteners.

Thus, there is a need for a condiment composition comprising non-caloric or low-caloric natural and/or synthetic high-potency sweeteners and methods thereof. There is an additional need in the art to provide a condiment composition comprising non-caloric or low-caloric natural and/or synthetic high-potency sweeteners with a more sugar-like taste and methods thereof.

SUMMARY OF THE INVENTION

Generally, this invention addresses the above described need by providing a condiment composition having improved temporal profile and/or flavor profile, a method for improving the temporal profile and/or flavor profile, a condiment composition having improved temporal and/or flavor profile, and a method for improving the temporal profile and/or flavor profile for condiment compositions. In particular, this invention improves the temporal profile and/or flavor profile by imparting a more sugar-like temporal profile and/or flavor profile. More particularly, this invention comprises a condiment composition comprising a condiment base; at least one high-potency sweetener; and at least one sweet taste improving composition.

Objects and advantages of the invention will be set forth in part in the following description, or may be obvious from the description, or may be learned through practice of the invention. Unless otherwise defined, all technical and scientific terms and abbreviations used herein have the same meaning as commonly understood by one of ordinary skill in the art to which this invention pertains. Although methods and compositions similar or equivalent to those described herein can be used in practice of the present invention, suitable methods and compositions are described without intending that any such methods and compositions limit the invention herein.

DETAILED DESCRIPTION OF THE INVENTION

Figure 1:
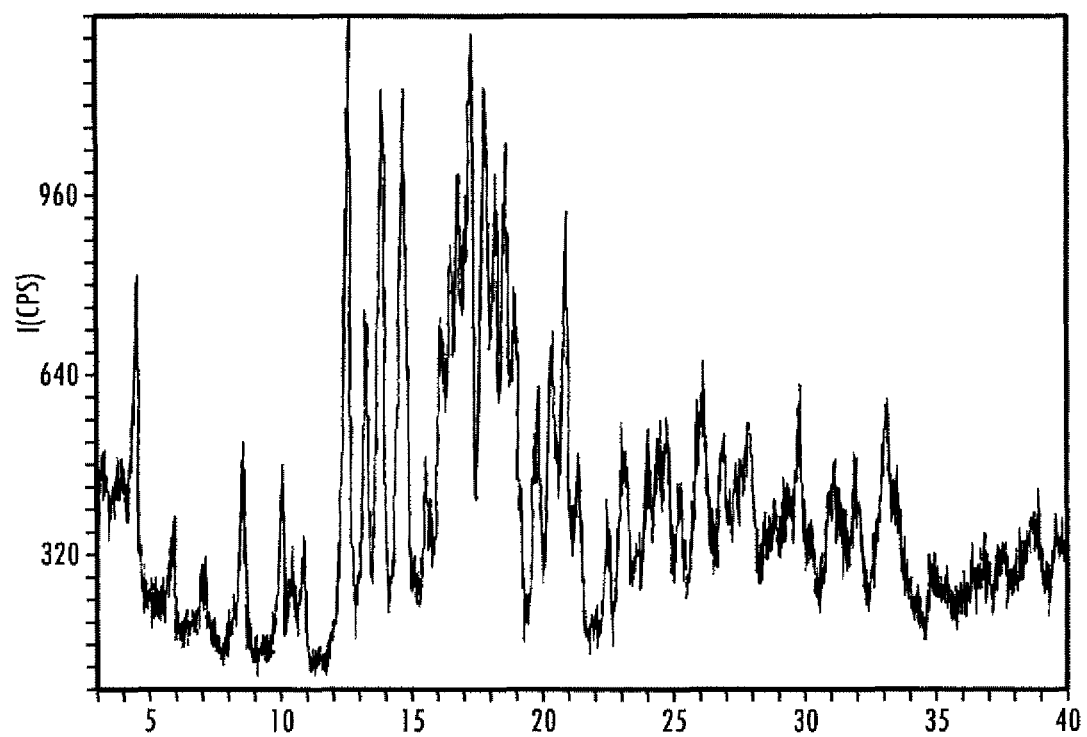
FIG. 1 is a powder x-ray diffraction scan of rebaudioside A polymorph Form 1 on a plot of the scattering intensity versus the scattering angle 2θ in accordance with an embodiment of this invention.

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

Generally described, embodiments of the present invention provide condiment compositions comprising at least one natural and/or synthetic high-potency sweetener, at least one sweet taste improving composition, and a condiment base.

I. Condiment Compositions

Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karayan, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, at least one natural and/or synthetic sweetener and sweet taste improving composition is used instead of traditional caloric sweeteners. Accordingly, a condiment composition desirably comprises at least one natural and/or synthetic high-potency sweetener in combination with at least one sweet taste improving composition and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

II. Sweetener Compositions

As described hereinabove, the condiment compositions comprise at least one natural and/or synthetic high-potency sweetener and at least one sweet taste improving composition. The combination of the at least one natural and/or synthetic high-potency sweetener and at least one sweet taste improving composition, as used herein, comprises the "sweetener composition." As used herein, a condiment base is synonymous with a "sweetenable composition." In addition, the combination of the sweetener composition and a condiment base comprises a "sweetened composition."

A. Natural High-Potency Sweeteners

Desirably, the sweetener composition comprises at least one natural and/or synthetic high-potency sweetener. As used herein the phrases "natural high-potency sweetener", "NHPS", "NHPS composition", and "natural high-potency sweetener composition" are synonymous. "NHPS" means any sweetener found in nature which may be in raw, extracted, purified, or any other form, singularly or in combination thereof and characteristically have a sweetness potency greater than sucrose, fructose, or glucose, yet have less calories. Non-limiting examples of NHPSs suitable for embodiments of this invention include rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, KR, RS, SR), curculin, glycyrrhizic acid and its salts, thaumatin, monellin, mabinlin, brazzein, hemandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I. NHPS also includes modified NHPSs. Modified NHPSs include NHPSs which have been altered naturally. For example, a modified NHPS includes, but is not limited to, NHPSs which have been fermented, contacted with enzyme, or derivatized or substituted on the NHPS. In one embodiment, at least one modified NHPS may be used in combination with at least one NHPS. In another embodiment, at least one modified NHPS may be used without a NHPS. Thus, modified NHPSs may be substituted for a NHPS or may be used in combination with NHPSs for any of the embodiments described herein. For the sake of brevity, however, in the description of embodiments of this invention, a modified NHPS is not expressly described as an alternative to an unmodified NHPS, but it should be understood that modified NHPSs can be substituted for NHPSs in any embodiment disclosed herein.

In one embodiment, extracts of a NHPS may be used in any purity percentage. In another embodiment, when a NHPS is used as a non-extract, the purity of the NHPS may range for example from about 25% to about 100%. According to other embodiments, the purity of the NHPS may range from about 50% to about 100% from about 70% to about 100%; from about 80% to about 100%; from about 90% to about 100%; from about 95% to about 100%; from about 95% to about 99.5%; from about 96% to about 100%; from about 97% to about 100%; from about 98% to about 100%; and from about 99% to about 100%.

Purity, as used here, represents the weight percentage of a respective NHPS compound present in a NHPS extract, in raw or purified form. In one embodiment, a steviolglycoside extract comprises a particular steviolglycoside in a particular purity, with the remainder of the stevioglycoside extract comprising a mixture of other steviolglycosides.

To obtain a particularly pure extract of a NHPS, such as rebaudioside A, it may be necessary to purify the crude extract to a substantially pure form. Such methods generally are known to those of ordinary skill in the art.

An exemplary method for purifying a NHPS, such as rebaudioside A, is described in the co-pending patent application Ser. No. 60/805,216, entitled "Rebaudioside A Composition and Method for Purifying Rebaudioside A," filed on Jun. 19, 2006, by inventors DuBois, et al., the disclosure of which is incorporated herein by reference in its entirety.

Briefly described, substantially pure rebaudioside A is crystallized in a single step from an aqueous organic solution comprising at least one organic solvent and water in an amount from about 10% to about 25% by weight, more particularly from about 15% to about 20% by weight. Organic solvents desirably comprise alcohols, acetone, and acetonitrile. Non-limiting examples of alcohols include ethanol, methanol, isopranol, 1-propanol, 1-butanol, 2-butanol, tert-butanol, and isobutanol. Desirably, the at least one organic solvent comprises a mixture of ethanol and methanol present in the aqueous organic solution in a weight ratio ranging from about 20 parts to about 1 part ethanol to 1 part methanol, more desirably from about 3 parts to about 1 part ethanol to 1 part methanol.

Desirably, the weight ratio of the aqueous organic solvent and crude rebaudioside A ranges from about 10 to about 4 parts aqueous organic solvent to 1 part crude rebaudioside A, more particularly from about 5 to about 3 parts aqueous organic solvent to 1 part crude rebaudioside A.

In an exemplary embodiment, the method of purifying rebaudioside A is carried out at approximately room temperature. In another embodiment, the method of purifying rebaudioside A further comprises the step of heating the rebaudioside A solution to a temperature in a range from about 20° C. to about 40° C., or in another embodiment to a reflux temperature, for about 0.25 hours to about 8 hours. In another exemplary embodiment, wherein the method for purifying rebaudioside A comprises the step of heating the rebaudioside A solution, the method further comprises the step of cooling the rebaudioside A solution to a temperature in the range from about 4° C. to about 25° C. for about 0.5 hours to about 24 hours.

According to particular embodiments, the purity of rebaudioside A may range from about 50% to about 100%; from about 70% to about 100%; from about 80% to about 100%; from about 90% to about 100%; from about 95% to about 100%; from about 95% to about 99.5%; about 96% to about 100%; from about 97% to about 100%; from about 98% to about 100%; and from about 99% to about 100%. According to particularly desirable embodiments, upon crystallization of crude rebaudioside A, the substantially pure rebaudioside A composition comprises rebaudioside A in a purity greater than about 95% by weight up to about 100% by weight on a dry basis. In other exemplary embodiments, substantially pure rebaudioside A comprises purity levels of rebaudioside A greater than about 97% up to about 100% rebaudioside A by weight on a dry basis, greater than about 98% up to about 100% by weight on a dry basis, or greater than about 99% up to about 100% by weight on a dry basis. The rebaudioside A solution during the single crystallization step may be stirred or unstirred.

In an exemplary embodiment, the method of purifying rebaudioside A further comprises the step of seeding (optional step) the rebaudioside A solution at an appropriate temperature with high-purity crystals of rebaudioside A sufficient to promote crystallization of the rebaudioside A to form pure rebaudioside A. An amount of rebaudioside A sufficient to promote crystallization of substantially pure rebaudioside A comprises an amount of rebaudioside A from about 0.0001% to about 1% by weight of the rebaudioside A present in the solution, more particularly from about 0.01% to about 1% by weight. An appropriate temperature for the step of seeding comprises a temperature in a range from about 18° C. to about 35° C.

In another exemplary embodiment, the method of purifying rebaudioside A further comprises the steps of separating and washing the substantially pure rebaudioside A composition. The substantially pure rebaudioside A composition may be separated from the aqueous organic solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the rebaudioside A solid-liquid separation device may be continuous, semi-continuous or in batch mode. The substantially pure rebaudioside A composition also may be washed on the separation device using various aqueous organic solvents and mixtures thereof. The substantially pure rebaudioside A composition can be dried partially or totally on the separation device using any number of gases, including, without limitation, nitrogen and argon, to evaporate residual liquid solvent. The substantially pure rebaudioside A composition may be removed automatically or manually from the separation device using liquids, gases or mechanical means by either dissolving the solid or maintaining the solid form.

In still another exemplary embodiment, the method of purifying rebaudioside A further comprises the step of drying the substantially pure rebaudioside A composition using techniques well known to those skilled in the art, non-limiting examples of which include the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the step of drying comprises drying the substantially pure rebaudioside A composition using a nitrogen or argon purge to remove the residual solvent at a temperature in a range from about 40° C. to about 60° C. for about 5 hours to about 100 hours.

In yet another exemplary embodiment, wherein the crude rebaudioside A mixture comprises substantially no rebaudioside D impurity, the method of purifying rebaudioside A further comprises the step of slurrying the composition of substantially pure rebaudioside A with an aqueous organic solvent prior to the step of drying the substantially pure rebaudioside A composition. The slurry is a mixture comprising a solid and an aqueous organic or organic solvent, wherein the solid comprises the substantially pure rebaudioside A composition and is only sparingly soluble in the aqueous organic or organic solvent. In an embodiment, the substantially pure rebaudioside A composition and aqueous organic solvent are present in the slurry in a weight ratio ranging from about 15 parts to 1 part aqueous organic solvent to 1 part substantially pure rebaudioside A composition. In one embodiment, the slurry is maintained at room temperature. In another embodiment, the step of slurrying comprises heating the slurry to a temperature in a range from about 20 to about 40° C. The substantially pure rebaudioside A composition is slurried for about 0.5 hours to about 24 hours, In still yet another exemplary embodiment, the method of purifying rebaudioside A further comprises the steps of separating the substantially pure rebaudioside A composition from the aqueous organic or organic solvent of the slurry and washing the substantially pure rebaudioside A composition followed by the step of drying the substantially pure rebaudioside A composition.

If further purification is desired, the method of purifying rebaudioside A described herein may be repeated or the substantially pure rebaudioside A composition may be purified further using an alternative purification method, such as the column chromatography.

It also is contemplated that other NHPSs may be purified using the purification method described herein, requiring only minor experimentation that would be obvious to those of ordinary skill in the art.

Figure 2:
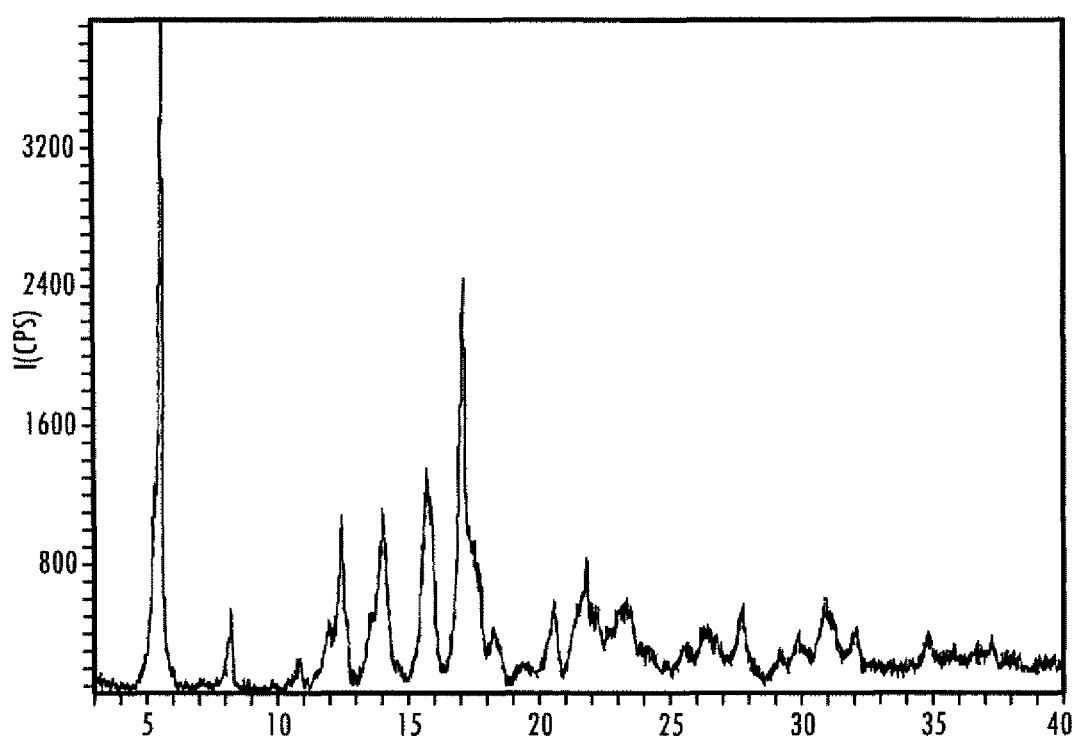
FIG. 2 is a powder x-ray diffraction scan of rebaudioside A polymorph Form 2 on a plot of the scattering intensity versus the scattering angle 2θ in accordance with an embodiment of this invention.
Figure 3:
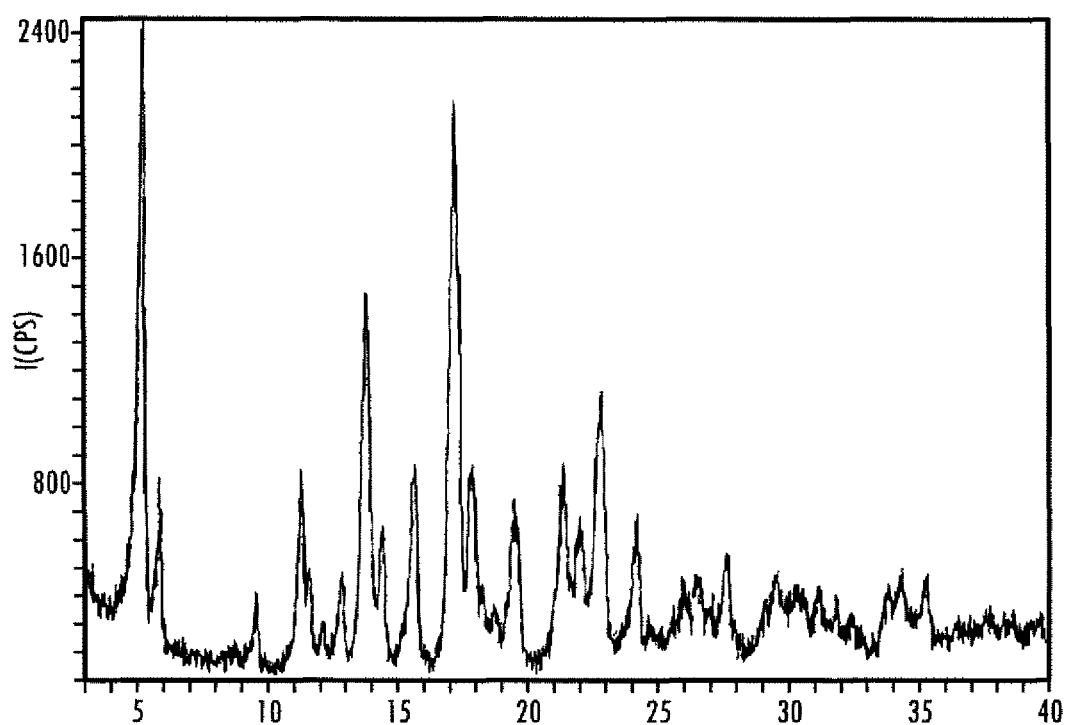
FIG. 3 is a powder x-ray diffraction scan of rebaudioside A polymorph Form 3A on a plot of the scattering intensity versus the scattering angle 2θ in accordance with an embodiment of this invention.
Figure 4:
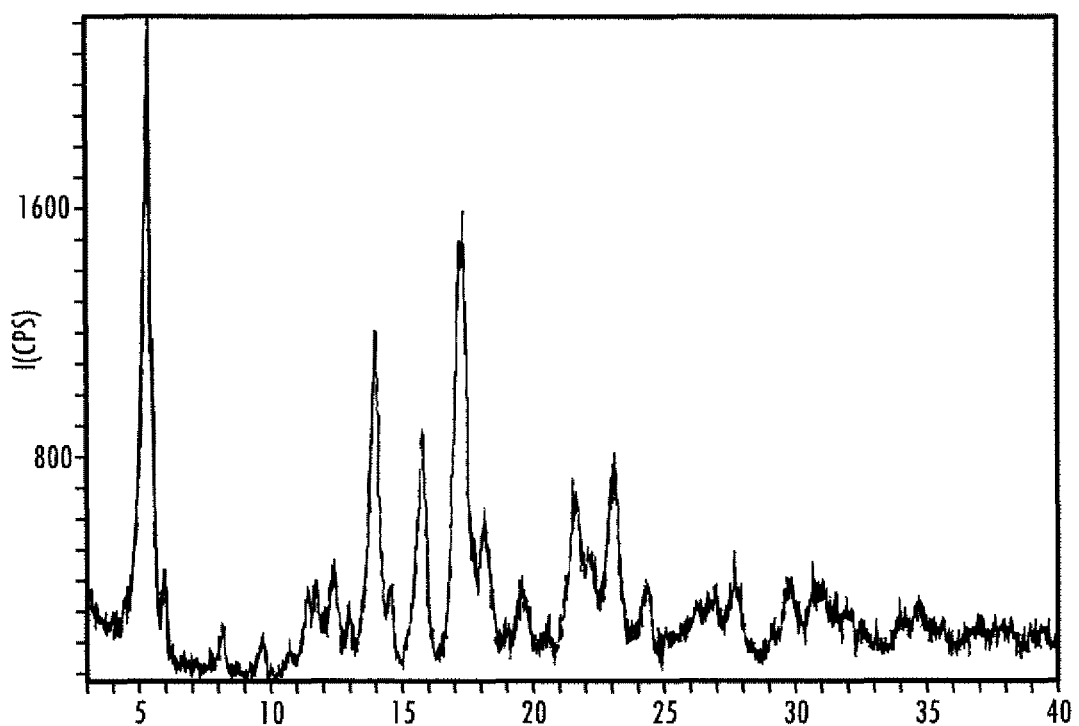
FIG. 4 is a powder x-ray diffraction scan of rebaudioside A polymorph Form 1B on a plot of the scattering intensity versus the scattering angle 2θ in accordance with an embodiment of this invention.
Figure 5:
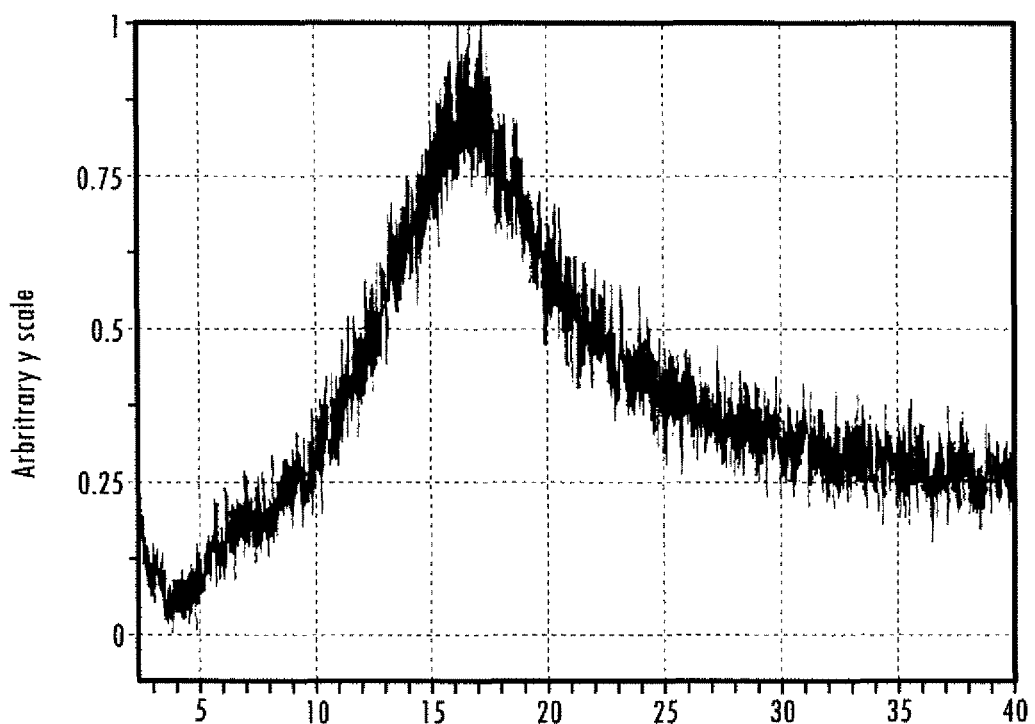
FIG. 5 is a powder x-ray diffraction scan of rebaudioside A polymorph Form 4 on a plot of the scattering intensity versus the scattering angle 2θ in accordance with an embodiment of this invention.

The purification of rebaudioside A by crystallization as described above results in the formation of at least four three different polymorphs: Form 1: a rebaudioside A hydrate; Form 2: an anhydrous rebaudioside A; and Form 3: a rebaudioside A solvate.; In addition to the at least three polymorph forms of rebaudioside A, the purification of rebaudioside A may result in the formation of an amorphous form of rebaudioside A,and Form 4: an amorphous rebaudioside A. The aqueous organic solution and temperature of the purification process influence the resulting polymorph and amorphous forms in the substantially pure rebaudioside A composition. FIGS. 1-5 are exemplary powder x-ray diffraction (XRPD) scans of the polymorph and amorphous forms of rebaudioside A: Form 1 (hydrate), Form 2 (anhydrate), Form 3A (methanol solvate), Form 3B (ethanol solvate), and Form 4 (amorphous), respectively.

The material properties of the four three rebaudioside A polymorphs and amorphous forms are summarized in the following table:

TABLE 1

Rebaudioside A Polymorph and Amorphous Forms

|  | Form 1 Polymorph | Form 2 Polymorph | Form 3 Polymorph | Form 4 Polymorph Amorphous |
|---|---|---|---|---|
| Rate of dissolution in H2O at 25° C. | Very low (<0.2%/60 minutes) | Intermediate (<30%/5 minutes) | High (>30%/5 minutes) | High (>35.0%/5 minutes) |
| Alcohol content | <0.5% | <1% | 1–3% | <0.05% |
| Moisture content | >5% | <1% | <3% | 6.74% |

The type of polymorph formed is dependent on the composition of the aqueous organic solution, the temperature of the crystallization step, and the temperature during the drying step. Form 1 and Form 3 are formed during the single crystallization step while Form 2 is formed during the drying step after conversion from Form 1 or Form 3.

Low temperatures during the crystallization step, in the range of about 20C to about 50° C., and a low ratio of water to the organic solvent in the aqueous organic solvent results in the formation of Form 3. High temperatures during the crystallization step, in the range of about 50° C. to about 80° C., and a high ratio of water to the organic solvent in the aqueous organic solvent results in the formation of the Form 1. Form 1 can be converted to Form 3 by slurrying in an anhydrous solvent at room temperature (2-16 hours) or at reflux for approximately (0.5-3 hours). Form 3 can be converted to Form 1 by slurrying the polymorph in water at room temperature for approximately 16 hours or at reflux for approximately 2-3 hours. Form 3 can be converted to the Form 2 during the drying process; however, increasing either the drying temperature above 70° C. or the drying time of a substantially pure rebaudioside A composition can result in decomposition of the rebaudioside A and increase the remaining rebaudioside B impurity in the substantially pure rebaudioside A composition. Form 2 can be converted to Form 1 with the addition of water.

Form 4 may be formed from Form 1, 2, 3, or combinations thereof, using methods well known to those of ordinary skill in the art. Non-limiting examples of such methods include melt-processing, ball milling, crystallization, lyohilization, cryo-grinding, and spray-drying. In a particular embodiment, Form 4 can be prepared from a substantially pure rebaudioside A composition obtained by the purification methods described hereinabove by spray-drying a solution of the substantially pure rebaudioside A composition.

B. Synthetic High-Potency Sweeteners

As used herein, the phrase "synthetic sweetener" refers to any compositions which are not found in nature and characteristically have a sweetness potency greater than sucrose, fructose, or glucose, yet have less calories. Non-limiting examples of synthetic sweeteners suitable for embodiments of this invention include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

C. Combinations of Natural and/or Synthetic High-Potency Sweeteners

The NHPS and synthetic sweeteners may be used individually or in combination with other N PS and/or synthetic sweeteners. For example, the sweetener composition may comprise a single NHPS or a single synthetic sweetener; a single NHPS in combination with a single synthetic sweetener; one or more NHPSs in combination with a single synthetic sweetener; a single NHPS in combination with one or more synthetic sweeteners; or one or more NHPSs in combination with one or more synthetic sweeteners. A plurality of natural and/or synthetic high-potency sweeteners may be used as long as the combined effect does not adversely affect the taste of the sweetener composition.

For example, particular embodiments comprise combinations of NHPSs, such as steviolglycosides. Non-limiting examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside E, rebaudioside F, stevioside, steviolbioside, dulcoside A, or combinations thereof.

Generally, according to a particular embodiment, rebaudioside A is present in the combination of high-potency sweeteners in an amount in the range of about 50 to about 99.5 weight percent of the combination of high-potency sweeteners, more desirably in the range of about 70 to about 90 weight percent, and still more desirably in the range of about 75 to about 85 weight percent.

In another particular embodiment, rebaudioside B is present in the combination of high-potency sweeteners in an amount in the range of about 1 to about 8 weight percent of the combination of high-potency sweeteners, more desirably in the range of about 2 to about 5 weight percent, and still more desirably in the range of about 2 to about 3 weight percent.

In another particular embodiment, rebaudioside C is present in the combination of high-potency sweeteners in an amount in the range of about 1 to about 10 weight percent of the combination of high-potency sweeteners, more desirably in the range of about 3 to about 8 weight percent, and still more desirably in the range of about 4 to about 6 weight percent.

In still another particular embodiment, rebaudioside E is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still another particular embodiment, rebaudioside F is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still yet another particular embodiment, dulcoside A is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In yet another particular embodiment, dulcoside B is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In another particular embodiment, stevioside is present in the combination of high-potency sweeteners in an amount in the range of about 0.5 to about 10 weight percent of the combination of high-potency sweeteners, more desirably in the range of about 1 to about 6 weight percent, and still more desirably in the range of about 1 to about 4 weight percent.

In still another particular embodiment, steviolbioside is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

According to a particularly desirable embodiment, the high-potency sweetener composition comprises a combination of rebaudioside A, stevioside, rebaudioside B, rebaudioside C, and rebaudioside F; wherein rebaudioside A is present in the combination of high-potency sweeteners in an amount in the range of about 75 to about 85 weight percent based on the total weight of the combination of high-potency sweeteners, stevioside is present in an amount in the range of about 1 to about 6 weight percent, rebaudioside B is present in an amount in the range of about 2 to about 5 weight percent, rebaudioside C is present in an amount in the range of about 3 to about 8 weight percent, and rebaudioside F is present in an amount in the range of about 0.1 to about 2 weight percent.

In addition, those of ordinary skill in the art should appreciate that the sweetener composition can be customized to obtain a desired calorie content. For example, a low-caloric or non-caloric NHPS may be combined with a caloric natural sweetener and/or other caloric additives to produce a sweetener composition with a preferred calorie content.

III. Sweet Taste Improving Compositions

The sweetener composition also comprises a sweet taste improving composition, non-limiting examples of which include carbohydrates, polyols, amino acids and their corresponding salts, polyamino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof.

In one embodiment, a single sweet taste improving composition may be used in combination with a single natural and/or synthetic high-potency sweetener. In another embodiment of the present invention, a single sweet taste improving composition may be used in combination with one or more natural and/or synthetic high-potency sweeteners. In yet another embodiment, one or more sweet taste improving compositions may be used in combination with a single natural and/or synthetic high-potency sweetener. In a further embodiment, there may be a plurality of sweet taste improving combinations used in combination with one or more natural and/or synthetic high-potency sweeteners.

In a particular embodiment, combinations of at least one natural and/or synthetic high-potency sweetener and at least one sweet taste improving composition suppress, reduce, or eliminate undesirable taste and impart sugar-like characteristics to the sweetener composition. As used herein, the phrase "undesirable taste" includes any taste property which is not imparted by sugars, e.g. glucose, sucrose, fructose, or similar saccharides. Non-limiting examples of undesirable tastes include delayed sweetness onset, lingering sweet aftertaste, metallic taste, bitter taste, cooling sensation taste or menthol-like taste, licorice-like taste, and/or the like.

A. Sweet Taste

In one embodiment, a sweetener composition exhibits a more sugar-like temporal and/or sugar-like flavor profile than a sweetener composition comprising at least one natural and/or synthetic high-potency sweetener, but without a sweet taste improving composition is provided. As used herein, the phrases "sugar-like characteristic," "sugar-like taste," "sugar-like sweet," "sugary," and "sugar-like" are synonymous. Sugar-like characteristics include any characteristic similar to that of sucrose and include, but are not limited to, maximal response, flavor profile, temporal profile, adaptation behavior, mouthfeel, concentration/response function behavior, tastant and flavor/sweet taste interactions, spatial pattern selectivity, and temperature effects. These characteristics are dimensions in which the taste of sucrose is different from the tastes of natural and synthetic high-potency sweeteners. Whether or not a characteristic is more sugar-like is determined by expert sensory panel assessments of sugar and compositions comprising at least one natural and/or synthetic high-potency sweetener, both with and without a sweet taste improving composition. Such assessments quantify similarities of the characteristics of compositions comprising at least one natural and/or synthetic high-potency sweetener, both with and without a sweet taste improving composition, with those comprising sugar. Suitable procedures for determining whether a composition has a more sugar-like taste are well known in the art.

In a particular embodiment, a panel of assessors is used to measure the reduction of sweetness linger. Briefly described, a panel of assessors (generally 8 to 12 individuals) is trained to evaluate sweetness perception and measure sweetness at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In a particular embodiment, the panel of assessors may be trained using the Spectrum™ Descriptive Analysis Method (Meilgaard et al, *Sensory Evaluation Techniques*, 3$^{rd}$ edition, Chapter 11). Desirably, the focus of training should be the recognition of and the measure of the basic tastes; specifically, sweet. In order to ensure accuracy and reproducibility of results, each assessor should repeat the measure of the reduction of sweetness linger about three to about five times per sample, taking at least a five minute break between each repetition and/or sample and rinsing well with water to clear the mouth.

Generally, the method of measuring sweetness comprises taking a 10 mL sample into the mouth, holding the sample in the mouth for 5 seconds and gently swirling the sample in the mouth, rating the sweetness intensity perceived at 5 seconds, expectorating the sample (without swallowing following expectorating the sample), rinsing with one mouthful of water (e.g., vigorously moving water in mouth as if with mouth wash) and expectorating the rinse water, rating the sweetness intensity perceived immediately upon expectorating the rinse water, waiting 45 seconds and, while wating those 45 seconds, identifying the time of maximum perceived sweetness intensity and rating the sweetness intensity at that time (moving the mouth normally and swallowing as needed), rating the sweetness intensity after another 10 seconds, rating the sweetness intensity after another 60 seconds (cumulative 120 seconds after rinse), and rating the sweetness intensity after still another 60 seconds (cumulative 180 seconds after rinse). Between samples take a 5 minute break, rinsing well with water to clear the mouth.

B. Types of Sweet Taste Improving Compositions

As described hereinabove, sweet taste improving compositions include carbohydrates, polyols, amino acids and their corresponding salts, polyamino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof.

As used herein, the term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Non-limiting examples of carbohydrates in embodiments of this invention include tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup. Additionally, the carbohydrates as used herein may be in either the D- or L-configuration.

The term "polyol", as used herein, refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain, 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of sweet taste improving polyol additives in embodiments of this invention include erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the sweetener composition.

Suitable sweet taste improving amino acid additives for use in embodiments of this invention include, but are not limited to, aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, or gamma- isomers), glutamine, hydroxyproline, taurine, norvaline, sarcosine, and their salt forms such as sodium or potassium salts or acid salts. The sweet taste improving amino acid additives also may be in the D- or L-configuration and in the mono-, di-, or tri- form of the same or different amino acids. Additionally, the amino acids may be α-, β-, γ-, δ-, and ε- isomers if appropriate. Combinations of the foregoing amino acids and their corresponding salts (e.g., sodium, potassium, calcium, magnesium salts or other alkali or alkaline earth metal salts thereof or acid salts) also are suitable sweet taste improving additives in embodiments of this invention. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, amino acids encompass both modified and unmodified amino acids. As used herein, modified amino acid also may encompass peptides and polypeptides (e.g., dipeptides, tripeptides, tetrapeptides, and pentapeptides) such as glutathione and L-alanyl-L-glutamine.

Suitable sweet taste improving polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., magnesium, calcium, potassium, or sodium salts such as L-glutamic acid mono sodium salt). The sweet taste improving polyamino acid additives also may be in the D- or L-configuration. Additionally, the polyamino acids may be α-, β-, γ-, δ-, and ε-isomers if appropriate. Combinations of the foregoing polyamino acids and their corresponding salts (e.g., sodium, potassium, calcium, magnesium salts or other alkali or alkaline earth metal salts thereof or acid salts) also are suitable sweet taste improving additives in embodiments of this invention. The polyamino acids described herein also may comprise co-polymers of different amino acids. The polyamino acids may be natural or synthetic. The polyamino acids also may be modified, such that at least one atom has been added, removed, substituted, or combinations thereof (e.g., N-alkyl polyamino acid or N-acyl polyamino acid). As used herein, polyamino acids encompass both modified and unmodified polyamino acids. In accordance with particular embodiments, modified polyamino acids include, but are not limited to polyamino acids of various molecular weights (MW), such as poly-L-α-lysine with a MW of 1,500, MW of 6,000, MW of 25,200, MW of 63,000, MW of 83,000, or MW of 300,000.

Suitable sweet taste improving sugar acid additives for use in embodiments of this invention include, but are not limited to, aldonic, uronic, aldaric, alginic, gluconic, glucuronic, glucaric, galactaric, galacturonic, and their salts (e.g., sodium, potassium, calcium, magnesium salts or other physiologically acceptable salts), and combinations thereof.

Suitable sweet taste improving nucleotide additives for use in embodiments of this invention include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, and their alkali or alkaline earth metal salts, and combinations thereof The nucleotides described herein also may comprise nucleotide-related additives, such as nucleosides or nucleic acid bases (e.g., guanine, cytosine, adenine, thymine, uracil).

Suitable sweet taste improving organic acid additives include any compound which comprises a —COOH moiety. Suitable sweet taste improving organic acid additives for use in embodiments of this invention include, but are not limited to, C2-C30 carboxylic acids, substituted hydroxyl C1-C30 carboxylic acids, benzoic acid, substituted benzoic acids (e.g. 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, glucosamine hydrochloride, glucono delta lactone, caffeic acid, bile acids, acetic acid, ascorbic acid, alginic acid, erythorbic acid, polyglutamic acid, and their alkali or alkaline earth metal salt derivatives thereof In addition, the sweet taste improving organic acid additives also may be in either the D- or L-configuration.

Suitable sweet taste improving organic acid salt additives include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), and adipic acid. The examples of the sweet taste improving organic acid salt additives described optionally may be substituted with one or more of the following moiety selected from the group consisting of hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phospho, phosphonato, and any other viable functional group, provided the substituted organic acid salt additive functions to improve the sweet taste of the sweetener composition.

Suitable sweet taste improving inorganic acid additives for use in embodiments of this invention include, but are not limited to, phosphoric acid, phosphorous acid, polyphosphoric acid, hydrochloric acid, sulfuric acid, carbonic acid, sodium dihydrogen phosphate, and their corresponding alkali or alkaline earth metal salts thereof (e.g., inositol hexaphosphate Mg/Ca).

Suitable sweet taste improving bitter compound additives for use in embodiments of this invention include, but are not limited to, caffeine, quinine, urea, bitter orange oil, naringin, quassia, and salts thereof.

Suitable sweet taste improving flavorant and flavoring ingredient additives for use in embodiments of this invention include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous, and include natural or synthetic substances or combinations thereof. Flavorants also include any other substance which imparts flavor, and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise, Holzminden™, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable sweet taste improving polymer additives for use in embodiments of this invention include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polyarginine, polypropylene glycol, polyethylene glycol, poly(ethylene glycol methyl ether), polyaspartic acid, polyglutamic acid, polyethyleneimine, alginic acid, sodium alginate, propylene glycol alginate, sodium hexametaphosphate (SHMP) and its salts, and sodium polyethyleneglycolalginate and other cationic and anionic polymers.

Suitable sweet taste improving protein or protein hydrolysate additives for use in embodiments of this invention include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable sweet taste improving surfactant additives for use in embodiments of this invention include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinlium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable sweet taste improving flavonoid additives for use in embodiments of this invention generally are classified as flavonols, flavones, flavanones, flavan-3-ols, isoflavones, or anthocyanidins. Non-limiting examples of flavonoid additives include catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-Ei Gen F.F.I., Inc., Osaka, Japan)), neohesperidin, naringin, neohesperidin dihydrochalcone, and the like.

Suitable sweet taste improving alcohol additives for use in embodiments of this invention include, but are not limited to, ethanol.

Suitable sweet taste improving astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

Suitable sweet taste improving vitamins include nicotinamide (Vitamin B3) and pyridoxal hydrochloride (Vitamin B6).

The sweet taste improving compositions also may comprise natural and/or synthetic high-potency sweeteners. For example, wherein the sweetener composition comprises at least one NHPS, the at least one sweet taste improving composition may comprise a synthetic high-potency sweetener, non-limiting examples of which include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

The sweet taste improving compositions also may be in salt form which may be obtained using standard procedures well known in the art. The term "salt" also refers to complexes that retain the desired chemical activity of the sweet taste improving compositions of the present invention and are safe for human or animal consumption in a generally acceptable range. Alkali metal (for example, sodium or potassium) or alkaline earth metal (for example, calcium or magnesium) salts also can be made. Salts also may include combinations of alkali and alkaline earth metals. Non-limiting examples of such salts are (a) acid addition salts formed with inorganic acids and salts formed with organic acids; (b) base addition salts formed with metal cations such as calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b). Thus, any salt forms which may be derived from the sweet taste improving compositions may be used with the embodiments of the present invention as long as the salts of the sweet taste improving additives do not adversely affect the taste of the sweetener compositions comprising the at least one natural and/or synthetic high-potency sweetener. The salt forms of the additives can be added to the natural and/or synthetic sweetener composition in the same amounts as their acid or base forms.

In particular embodiments, suitable sweet taste improving inorganic salts useful as sweet taste improving additives include, but are not limited to, sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, mono-, di-, tri-basic sodium or potassium salts of phosphoric acid (e.g., inorganic phosphates), salts of hydrochloridic acid (e.g., inorganic chlorides), sodium carbonate, sodium bisulfate, and sodium bicarbonate. Furthermore, in particular embodiments, suitable organic salts useful as sweet taste improving additives include, but are not limited to, choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, amiloride HCl, monosodium glutamate (MSG), adenosine monophosphate salt, magnesium gluconate, potassium tartrate (monohydrate), and sodium tartrate (dihydrate).

C. Combinations of Sweet Taste Improving Compositions

It has been discovered that combinations of at least one natural and/or synthetic high-potency sweetener and at least one sweet taste improving composition improve the temporal profile and/or flavor profile, including the osmotic taste, to be more sugar-like. One of ordinary skill in the art, with the teachings of the present invention, may arrive at all the possible combinations of natural and/or synthetic high-potency sweeteners and sweet taste improving compositions. For example, non-limiting combinations of the natural and/or synthetic high-potency sweetener and sweet taste improving compositions include:

1. at least one natural and/or synthetic high-potency sweetener and at least one carbohydrate;
2. at least one natural and/or synthetic high-potency sweetener and at least one polyol;
3. at least one natural and/or synthetic high-potency sweetener and at least one amino acid;
4. at least one natural and/or synthetic high-potency sweetener and at least one other sweet taste improving additive;
5. at least one natural and/or synthetic high-potency sweetener, at least one carbohydrate, at least one polyol, at least one amino acid, and at least one other sweet taste improving additive;
6. at least one natural and/or synthetic high-potency sweetener, at least one carbohydrate, and at least one polyol;
7. at least one natural and/or synthetic high-potency sweetener, at least one carbohydrate, and at least one amino acid;
8. at least one natural and/or synthetic high-potency sweetener, at least one carbohydrate, and at least one other sweet taste improving additive;
9. at least one natural and/or synthetic high-potency sweetener, at least one polyol, and at least one amino acid;
10. at least one natural and/or synthetic high-potency sweetener, at least one polyol, and at least one other sweet taste improving additive;
11. at least one natural and/or synthetic high-potency sweetener, at least one amino acid, and at least one other sweet taste improving additive;
12. at least one natural and/or synthetic high-potency sweetener, at least one carbohydrate, at least one polyol, and at least one amino acid;
13. at least one natural and/or synthetic high-potency sweetener, at least one carbohydrate, at least one polyol, and at least one other sweet taste improving additive;
14. at least one natural and/or synthetic high-potency sweetener, at least one polyol, at least one amino acid, and at least one other sweet taste improving additive; and
15. at least one natural and/or synthetic high-potency sweetener, at least one carbohydrate, at least one amino acid, and at least one other sweet taste improving additive.

These fifteen major combinations further may be broken down into further combinations in order to improve the overall taste of the natural and/or synthetic high-potency sweetener or the sweetened compositions comprising the natural and/or synthetic high-potency sweetener.

As explained above, the sweet taste improving composition is selected from the group consisting of polyols, carbohydrates, amino acids, other sweet taste improving additives, and combinations thereof. The other sweet taste improving additives useful in embodiments of this invention are described hereinabove. In one embodiment, a single sweet taste improving composition may be used with a single natural or synthetic high-potency sweetener and a condiment base. In another embodiment of the present invention, a single sweet taste improving composition may be used with one or more natural and/or synthetic high-potency sweeteners and a condiment base. In yet another embodiment, one or more sweet taste improving compositions may be used with a single natural or synthetic high-potency sweetener and a condiment base. In a further embodiment, there may be a plurality of sweet taste improving compositions used in combination with one or more natural and/or synthetic high-potency sweeteners and a condiment base. Thus, non-limiting examples of sweet taste improving composition combinations for embodiments of this invention include:

i. at least one polyol, at least one carbohydrate, at least one amino acid, and at least one other sweet taste improving additive;
ii. at least one polyol, at least one carbohydrate, and at least one other sweet taste improving additive;
iii. at least one polyol and at least one other sweet taste improving additive;
iv. at least one polyol and at least one carbohydrate;
v. at least one carbohydrate and at least one other sweet taste improving additive;
vi. at least one polyol and at least one amino acid;
vii at least one carbohydrate and at least one amino acid;
viii. at least one amino acid and at least one other sweet taste improving additive.

Other sweet taste improving composition combinations in accordance with embodiments of this invention include:

1. at least one polyol, at least one carbohydrate, and at least one amino acid;
2. at least one polyol, at least one carbohydrate, and at least one polyamino acid;
3. at least one polyol, at least one carbohydrate, and at least one sugar acid;
4. at least one polyol, at least one carbohydrate, and at least one nucleotide;
5. at least one polyol, at least one carbohydrate, and at least one organic acid;
6. at least one polyol, at least one carbohydrate, and at least one inorganic acid;
7. at least one polyol, at least one carbohydrate, and at least one bitter compound;
8. at least one polyol, at least one carbohydrate, and at least one flavorant or flavoring ingredient;
9. at least one polyol, at least one carbohydrate, and at least one polymer;
10. at least one polyol, at least one carbohydrate, and at least one protein or protein hydrolysate or protein or protein hydrolysate with low molecular weight amino acid;
11. at least one polyol, at least one carbohydrate, and at least one surfactant;
12. at least one polyol, at least one carbohydrate, and at least one flavonoid;
13. at least one polyol, at least one carbohydrate, and at least one alcohol;
14. at least one polyol, at least one carbohydrate, and at least one emulsifier;
15. at least one polyol, at least one carbohydrate, and at least one inorganic salt,
16. at least one polyol, at least one carbohydrate, and at least one organic salt,
17. at least one polyol, at least one carbohydrate, and at least one amino acid, and at least one other sweet taste improving additive;

18. at least one polyol, at least one carbohydrate, and at least one polyamino acid, and at least one other sweet taste improving additive;
19. at least one polyol, at least one carbohydrate, and at least one sugar acid, and at least one other sweet taste improving additive;
20. at least one polyol, at least one carbohydrate, and at least one nucleotide, and at least one other sweet taste improving additive;
21. at least one polyol, at least one carbohydrate, and at least one organic acid, and at least one other sweet taste improving additive;
22. at least one polyol, at least one carbohydrate, and at least one inorganic acid, and at least one other sweet taste improving additive;
23. at least one polyol, at least one carbohydrate, and at least one bitter compound, and at least one other sweet taste improving additive;
24. at least one polyol, at least one carbohydrate, and at least one flavorant or flavoring ingredient, and at least one other sweet taste improving additive;
25. at least one polyol, at least one carbohydrate, and at least one polymer, and at least one other sweet taste improving additive;
26. at least one polyol, at least one carbohydrate, and at least one protein or protein hydrolysate, and at least one other sweet taste improving additive;
27. at least one polyol, at least one carbohydrate, and at least one surfactant, and at least one other sweet taste improving additive;
28. at least one polyol, at least one carbohydrate, and at least one flavonoid, and at least one other sweet taste improving additive;
29. at least one polyol, at least one carbohydrate, and at least one alcohol, and at least one other sweet taste improving additive;
30. at least one polyol, at least one carbohydrate, at least one amino acid, and at least one polyamino acid;
31. at least one polyol, at least one carbohydrate, at least one amino acid, at least one polyamino acid, and at least one sugar acid;
32. at least one polyol, at least one carbohydrate, at least one amino acid, at least one polyamino acid, at least one sugar acid, and at least one nucleotide;
33. at least one polyol, at least one carbohydrate, at least one amino acid, at least one polyamino acid, at least one sugar acid, at least one nucleotide, and at least one organic acid;
34. at least one polyol, at least one carbohydrate, at least one amino acid, at least one polyamino acid, at least one sugar acid, at least one nucleotide, at least one organic acid, and at least one inorganic acid;
35. at least one polyol, at least one carbohydrate, at least one amino acid, at least one polyamino acid, at least one sugar acid, at least one nucleotide, at least one organic acid, at least one inorganic acid, and at least one bitter compound;
36. at least one polyol, at least one carbohydrate, at least one amino acid, at least one polyamino acid, at least one sugar acid, at least one nucleotide, at least one organic acid, at least one inorganic acid, at least one bitter compound, and at least one polymer;
37. at least one polyol, at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
40. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
41. at least one polyol, at least one carbohydrate, at least one amino acid, and at least one sugar acid;
42. at least one polyol, at least one carbohydrate, at least one amino acid, and at least one nucleotide;
43. at least one polyol, at least one carbohydrate, at least one amino acid, and at least one organic acid;
44. at least one polyol, at least one carbohydrate, at least one amino acid, and at least one inorganic acid;
45. at least one polyol, at least one carbohydrate, at least one amino acid, and at least one bitter compound;
46. at least one polyol, at least one carbohydrate, at least one amino acid, and at least one polymer;
47. at least one polyol, at least one carbohydrate, at least one amino acid, and at least one protein or protein hydrolysate;
48. at least one polyol, at least one carbohydrate, at least one amino acid, and at least one surfactant;
49. at least one polyol, at least one carbohydrate, at least one amino acid, and at least one flavonoid;
50. at least one polyol, at least one carbohydrate, at least one amino acid, and at least one alcohol;
51. at least one polyol, at least one carbohydrate, at least one polyamino acid, and at least one sugar acid;
52. at least one polyol, at least one carbohydrate, at least one polyamino acid, and at least one nucleotide;
53. at least one polyol, at least one carbohydrate, at least one polyamino acid, and at least one organic acid;
54. at least one polyol, at least one carbohydrate, at least one polyamino acid, and at least one inorganic acid;
55. at least one polyol, at least one carbohydrate, at least one polyamino acid, and at least one bitter compound;
56. at least one polyol, at least one carbohydrate, at least one polyamino acid, and at least one polymer;
57. at least one polyol, at least one carbohydrate, at least one polyamino acid, and at least one protein or protein hydrolysate;
58. at least one polyol, at least one carbohydrate, at least one polyamino acid, and at least one surfactant;
59. at least one polyol, at least one carbohydrate, at least one polyamino acid, and at least one flavonoid;
60. at least one polyol, at least one carbohydrate, at least one polyamino acid, and at least one alcohol;
61. at least one polyol, at least one carbohydrate, at least one sugar acid, and at least one nucleotide;

62. at least one polyol, at least one carbohydrate, at least one sugar acid, and at least one organic acid;
63. at least one polyol, at least one carbohydrate, at least one sugar acid, and at least one inorganic acid;
64. at least one polyol, at least one carbohydrate, at least one sugar acid, and at least one bitter compound;
65. at least one polyol, at least one carbohydrate, at least one sugar acid, and at least one polymer;
66. at least one polyol, at least one carbohydrate, at least one sugar acid, and at least one protein or protein hydrolysate;
67. at least one polyol, at least one carbohydrate, at least one sugar acid, and at least one surfactant;
68. at least one polyol, at least one carbohydrate, at least one sugar acid, and at least one flavonoid;
69. at least one polyol, at least one carbohydrate, at least one sugar acid, and at least one alcohol;
70. at least one polyol, at least one carbohydrate, at least one nucleotide, and at least one organic acid;
71. at least one polyol, at least one carbohydrate, at least one nucleotide, and at least one inorganic acid;
72. at least one polyol, at least one carbohydrate, at least one nucleotide, and at least one bitter compound;
73. at least one polyol, at least one carbohydrate, at least one nucleotide, and at least one polymer;
74. at least one polyol, at least one carbohydrate, at least one nucleotide, and at least one protein or protein hydrolysate;
75. at least one polyol, at least one carbohydrate, at least one nucleotide, and at least one surfactant;
76. at least one polyol, at least one carbohydrate, at least one nucleotide, and at least one flavonoid;
77. at least one polyol, at least one carbohydrate, at least one nucleotide, and at least one alcohol;
78. at least one polyol, at least one carbohydrate, at least one organic acid, and at least one inorganic acid;
79. at least one polyol, at least one carbohydrate, at least one organic acid, and at least one bitter compound;
80. at least one polyol, at least one carbohydrate, at least one organic acid, and at least one polymer;
81. at least one polyol, at least one carbohydrate, at least one organic acid, and at least one protein or protein hydrolysate;
82. at least one polyol, at least one carbohydrate, at least one organic acid, and at least one surfactant;
83. at least one polyol, at least one carbohydrate, at least one organic acid, and at least one flavonoid;
84. at least one polyol, at least one carbohydrate, at least one organic acid, and at least one alcohol;
85. at least one polyol, at least one carbohydrate, at least one inorganic acid, and at least one bitter compound;
86. at least one polyol, at least one carbohydrate, at least one inorganic acid, and at least one polymer;
87. at least one polyol, at least one carbohydrate, at least one inorganic acid, and at least one protein or protein hydrolysate;
88. at least one polyol, at least one carbohydrate, at least one inorganic acid, and at least one surfactant;
89. at least one polyol, at least one carbohydrate, at least one inorganic acid, and at least one flavonoid;
90. at least one polyol, at least one carbohydrate, at least one inorganic acid, and at least one alcohol;
91. at least one polyol, at least one carbohydrate, at least one bitter compound, and at least one polymer;
92. at least one polyol, at least one carbohydrate, at least one bitter compound, and at least one protein or protein hydrolysate;
93. at least one polyol, at least one carbohydrate, at least one bitter compound, and at least one surfactant;
94. at least one polyol, at least one carbohydrate, at least one bitter compound, and at least one flavonoid;
95. at least one polyol, at least one carbohydrate, at least one bitter compound, and at least one alcohol;
96. at least one polyol, at least one carbohydrate, at least one polymer, and at least one protein or protein hydrolysate;
97. at least one polyol, at least one carbohydrate, at least one polymer, and at least one surfactant;
98. at least one polyol, at least one carbohydrate, at least one polymer, and at least one flavonoid;
99. at least one polyol, at least one carbohydrate, at least one polymer, and at least one alcohol;
100. at least one polyol, at least one carbohydrate, at least one protein or protein hydrolysate, and at least one surfactant;
101. at least one polyol, at least one carbohydrate, at least one protein or protein hydrolysate, and at least one flavonoid;
102. at least one polyol, at least one carbohydrate, at least one surfactant, and at least one flavonoid;
103. at least one polyol, at least one carbohydrate, at least one surfactant, and at least one alcohol; and
104. at least one polyot, at least one carbohydrate, at least one flavonoid, and at least one alcohol.

Other sweet taste improving composition combinations in accordance with embodiments of this invention include:
1. at least one polyol and at least one amino acid;
2. at least one polyol and at least one polyamino acid;
3. at least one polyot and at least one sugar acid;
4. at least one polyol and at least one nucleotide;
5. at least one polyol and at least one organic acid;
6. at least one polyol and at least one inorganic acid;
7. at least one polyol and at least one bitter compound;
8. at least one polyol and at least one flavorant or flavoring ingredient;
9. at least one polyol and at least one polymer;
10. at least one polyol and at least one protein or protein hydrolysate;
11. at least one polyol and at least one surfactant;
12. at least one polyol and at least one flavonoid;
13. at least one polyol and at least one alcohol;
14. at least one polyol and at least one emulsifier;
15. at least one polyol and at least one inorganic salt;
16. at least one polyol and at least one organic salt;
17. at least one polyol and at least one protein or protein hydrolysate or mixture of low molecular weight amino acids;
18. at least one polyol, at least one amino acid, and at least one other sweet taste improving additive;
19. at least one polyol, at least one polyamino acid, and at least one other sweet taste improving additive;
20. at least one polyol, at least one sugar acid, and at least one other sweet taste improving additive;
21. at least one polyol, at least one nucleotide, and at least one other sweet taste improving additive;
22. at least one polyol, at least one organic acid, and at least one other sweet taste improving additive;
23. at least one polyol, at least one inorganic acid, and at least one other sweet taste improving additive;
24. at least one polyol, at least one bitter compound, and at least one other sweet taste improving additive;
25. at least one polyol, at least one flavorant or flavoring ingredient, and at least one other sweet taste improving additive;

26. at least one polyol, at least one polymer, and at least one other sweet taste improving additive;
27. at least one polyol, at least one protein or protein hydrolysate, and at least one other sweet taste improving additive;
28. at least one polyol, at least one surfactant, and at least one other sweet taste improving additive;
29. at least one polyol, at least one flavonoid, and at least one other sweet taste improving additive;
30. at least one polyol, at least one alcohol, and at least one other sweet taste improving additive;
31. at least one polyol, at least one amino acid, and at least one polyamino acid;
32. at least one polyol, at least one amino acid, at least one polyamino acid, and at least one sugar acid;
33. at least one polyol, at least one amino acid, at least one polyamino acid, at least one sugar acid, and at least one nucleotide;
34. at least one polyol, at least one amino acid, at least one polyamino acid, at least one sugar acid, at least one nucleotide, and at least one organic acid;
35. at least one polyol, at least one amino acid, at least one polyamino acid, at least one sugar acid, at least one nucleotide, at least one organic acid, and at least one inorganic acid;
36. at least one polyol, at least one amino acid, at least one polyamino acid, at least one sugar acid, at least one nucleotide, at least one organic acid, at least one inorganic acid, and at least one bitter compound;
37. at least one polyol, at least one amino acid, at least one polyamino acid, at least one sugar acid, at least one nucleotide, at least one organic acid, at least one inorganic acid, at least one bitter compound, and at least one polymer;
38. at least one polyol, at least one amino acid, at least one polyamino acid, at least one sugar acid, at least one nucleotide, at least one organic acid, at least one inorganic acid, at least one bitter compound, at least one polymer, and at least one protein or protein hydrolysate;
39. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
40. at least one poyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
41. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one ilavonoid, and at least one alcohol;
42. at least one polyol, at least one amino acid, and at least one sugar acid;
43. at least one polyol, at least one amino acid, and at least one nucleotide;
44. at least one polyol, at least one amino acid, and at least one organic acid;
45. at least one polyol, at least one amino acid, and at least one inorganic acid;
46. at least one polyol, at least one amino acid, and at least one bitter compound;
47. at least one polyol, at least one amino acid, and at least one polymer;
48. at least one polyol, at least one amino acid, and at least one protein or protein hydrolysate;
49. at least one polyol, at least one amino acid, and at least one surfactant;
50. at least one polyol, at least one amino acid, and at least one flavonoid;
51. at least one polyol, at least one amino acid, and at least one alcohol;
52. at least one polyol, at least one polyamino acid, and at least one sugar acid;
53. at least one polyol, at least one polyamino acid, and at least one nucleotide;
54. at least one polyol, at least one polyamino acid, and at least one organic acid;
55. at least one polyol, at least one polyamino acid, and at least one organic salt;
56. at least one polyol, at least one polyamino acid, and at least one inorganic acid;
57. at least one polyol, at least one polyamino acid, and at least one inorganic salt;
58. at least one polyol, at least one polyamino acid, and at least one bitter compound;
59. at least one polyol, at least one polyamino acid, and at least one polymer;
60. at least one polyol, at least one polyamino acid, and at least one protein or protein hydrolysate;
61. at least one polyol, at least one polyamino acid, and at least one surfactant;
62. at least one polyol, at least one polyamino acid, and at least one flavonoid;
63. at least one polyol, at least one polyamino acid, and at least one alcohol;
64. at least one polyol, at least one sugar acid, and at least one nucleotide;
65. at least one polyol, at least one sugar acid, and at least one organic acid;
66. at least one polyol, at least one sugar acid, and at least one inorganic acid;
67. at least one polyol, at least one sugar acid, and at least one bitter compound;
68. at least one polyol, at least one sugar acid, and at least one polymer;
69. at least one polyol, at least one sugar acid, and at least one protein or protein hydrolysate;
70. at least one polyol, at least one sugar acid, and at least one surfactant;
71. at least one polyol, at least one sugar acid, and at least one flavonoid;
72. at least one polyol, at least one sugar acid, and at least one alcohol;
73. at least one polyol, at least one nucleotide, and at least one organic acid;
74. at least one polyol, at least one nucleotide, and at least one inorganic acid;
75. at least one polyol, at least one nucleotide, and at least one bitter compound;
76. at least one polyol, at least one nucleotide, and at least one polymer;
77. at least one polyol, at least one nucleotide, and at least one protein or protein hydrolysate;
78. at least one polyol, at least one nucleotide, and at least one surfactant;

79. at least one polyol, at least one nucleotide, and at least one flavonoid;
80. at least one polyol, at least one nucleotide, and at least one alcohol;
81. at least one polyol, at least one organic acid, and at least one inorganic acid;
82. at least one polyol, at least one organic acid, and at least one bitter compound;
83. at least one polyol, at least one organic acid, and at least one polymer;
84. at least one polyol, at least one organic acid, and at least one protein or protein hydrolysate;
85. at least one polyol, at least one organic acid, and at least one surfactant;
86. at least one polyol, at least one organic acid, and at least one flavonoid;
87. at least one polyol, at least one organic acid, and at least one alcohol;
88. at least one polyol, at least one inorganic acid, and at least one bitter compound;
89. at least one polyol, at least one inorganic acid, and at least one polymer;
90. at least one polyol, at least one inorganic acid, and at least one protein or protein hydrolysate;
91. at least one polyol, at least one inorganic acid, and at least one surfactant;
92. at least one polyol, at least one inorganic acid, and at least one flavonoid;
93. at least one polyol, at least one inorganic acid, and at least one alcohol;
94. at least one polyol, at least one bitter compound, and at least one polymer;
95. at least one polyol, at least one bitter compound, and at least one protein or protein hydrolysate;
96. at least one polyol, at least one bitter compound, and at least one surfactant;
97. at least one polyol, at least one bitter compound, and at least one flavonoid;
98. at least one polyol, at least one bitter compound, and at least one alcohol;
99. at least one polyol, at least one polymer, and at least one protein or protein hydrolysate;
100. at least one polyol, at least one polymer, and at least one surfactant;
101. at least one polyol, at least one polymer, and at least one flavonoid;
102. at least one polyol, at least one polymer, and at least one alcohol;
103. at least one polyol, at least one protein or protein hydrolysate, and at least one surfactant;
104. at least one polyol, at least one protein or protein hydrolysate, and at least one flavonoid;
105. at least one polyol, at least one surfactant, and at least one flavonoid;
106. at least one polyol, at least one surfactant, and at least one alcohol;
107. at least one polyol, at least one flavonoid, and at least one alcohol;
108. at least one sweet taste improving additive and erythritol;
109. at least one sweet taste improving additive and maltitol;
110. at least one sweet taste improving additive and mannitol;
111. at least one sweet taste improving additive and sorbitol;
112. at least one sweet taste improving additive and lactitol;
113. at least one sweet taste improving additive and xylitol;
114. at least one sweet taste improving additive and isomalt;
115. at least one sweet taste improving additive and propylene glycol;
116. at least one sweet taste improving additive and glycerol;
117. at least one sweet taste improving additive and palatinose;
118. at least one sweet taste improving additive and reduced isomalto-oligosaccharides;
119. at least one sweet taste improving additive and reduced xylo-oligosaccharides;
120. at least one sweet taste improving additive and reduced gentio-oligosaccharides;
121. at least one sweet taste improving additive and reduced maltose syrups
122. at least one sweet taste improving additive and reduced glucose syrup;
123. at least one sweet taste improving additive, erythritol, and at least one other polyol;
124. at least one sweet taste improving additive, maltitol, and at least one other polyol;
125. at least one sweet taste improving additive, mannitol, and at least one other polyol;
126. at least one sweet taste improving additive, sorbitol, and at least one other polyol;
127. at least one sweet taste improving additive, lactitol, and at least one other polyol;
128. at least one sweet taste improving additive, xylitol, and at least one other polyol;
129. at least one sweet taste improving additive, isomalt, and at least one other polyol;
130. at least one sweet taste improving additive, propylene glycol, and at least one other polyol;
131. at least one sweet taste improving additive, glycerol, and at least one other polyol;
132. at least one sweet taste improving additive, palatinose, and at least one other polyol;
133. at least one sweet taste improving additive, reduced isomalto-oligosaccharides, and at least one other polyol;
134. at least one sweet taste improving additive, reduced xylo-oligosaccharides, and at least one other polyol;
135. at least one sweet taste improving additive, reduced gentio-oligosaccharides, and at least one other polyol;
136. at least one sweet taste improving additive, reduced maltose syrup, and at least one other polyol; and
137. at least one sweet taste improving additive, reduced glucose syrup, and at least one other polyol.

Other sweet taste improving composition combinations in accordance with embodiments of this invention include.
1. at least one polyol and tagatose;
2. at least one polyol and trehalose;
3. at least one polyol and galactose;
4. at least one polyol and rhamnose;
5. at least one polyol and dextrin;
6. at least one polyol and cyclodextrin;
7. at least one polyol and α-cyclodextrin, β-cyclodextrin, or γ-cyclodextrin;
8. at least one polyol and maltodextrin;
9. at least one polyol and dextran;
10. at least one polyol and sucrose;
11. at least one polyol and glucose;
12. at least one polyol and fructose;
13. at least one polyol and threose;

14. at least one polyol and arabinose;
15. at least one polyol and xylose;
16. at least one polyol and lyxose;
17. at least one polyol and allose;
18. at least one polyol and altrose;
19. at least one polyol and mannose;
20. at least one polyol and idose;
21. at least one polyol and talose;
22. at least one polyol and lactose;
23. at least one polyol and maltose;
24. at least one polyol and invert sugar;
25. at least one polyol and trehalose;
26. at least one polyol and isotrehalose;
27. at least one polyol and neotrehalose;
28. at least one polyol and palatinose;
29. at least one polyol and galactose;
30. at least one polyol and beet oligosaccharides;
31. at least one polyol and isomalto-oligosaecharides;
32. at least one polyol and isomaltose;
33. at least one polyol and isomaltotriose;
34. at least one polyol and panose;
35. at least one polyol and xylo-oligosaccharides;
36. at least one polyol and xylotriose;
37. at least one polyol and xylobiose;
38. at least one polyol and gentio-oligoscaccharides;
39. at least one polyol and gentiobiose;
40. at least one polyol and gentiotriose;
41. at least one polyol and gentiotetraose;
42. at least one polyol and sorbose;
43. at least one polyol and nigero-oligosaccharides;
44. at least one polyol and palatinose oligosaccharides;
45. at least one polyol and fucose;
46. at least one polyol and fructooligosaccharides;
47. at least one polyol and kestose;
48. at least one polyol and nystose;
49. at least one polyol and maltotetraol;
50. at least one polyol and maltotriol;
51. at least one polyol and malto-oligosaccharides;
52. at least one polyol and maltotriose;
53. at least one polyol and maltotetraose;
54. at least one polyol and maltopentaose;
55. at least one polyol and maltohexaose;
56. at least one polyol and maltoheptaose;
57. at least one polyol and lactulose;
58. at least one polyol and melibiose;
59. at least one polyol and raffinose;
60. at least one polyol and rhamnose;
61. at least one polyol and ribose;
62. at least one polyol and isomerized liquid sugars;
63. at least one polyol and high fructose corn syrup (e.g. HFCS55, HFCS42, or HFCS90) or starch syrup;
64. at least one polyol and coupling sugars;
65. at least one polyol and soybean oligosaccharides;
66. at least one polyol and glucose syrup;
67. at least one polyol, tagatose, and at least one other carbohydrate;
68. at least one polyol, trehalose, and at least one other carbohydrate;
69. at least one polyol, galactose, and at least one other carbohydrate;
70. at least one polyol, rhamnose, and at least one other carbohydrate;
71. at least one polyol, dextrin, and at least one other carbohydrate;
72. at least one polyol, cyclodextrin, and at least one other carbohydrate;
73. at least one polyol, β-cyclodextrin, and at least one other carbohydrate;
74. at least one polyol, maltodextrin, and at least one other carbohydrate;
75. at least one polyol, dextran, and at least one other carbohydrate;
76. at least one polyol, sucrose, and at least one other carbohydrate;
77. at least one polyol, glucose, and at least one other carbohydrate;
78. at least one polyol, fructose, and at least one other carbohydrate;
79. at least one polyol, threose, and at least one other carbohydrate;
80. at least one polyol, arabinose, and at least one other carbohydrate;
81. at least one polyol, xylose, and at least one other carbohydrate;
82. at least one polyol, lyxose, and at least one other carbohydrate;
83. at least one polyol, allose, and at least one other carbohydrate;
84. at least one polyol, altrose, and at least one other carbohydrate;
85. at least one polyol, mannose, and at least one other carbohydrate;
86. at least one polyol, idose, and at least one other carbohydrate;
87. at least one polyol, talose, and at least one other carbohydrate;
88. at least one polyol, lactose, and at least one other carbohydrate;
89. at least one polyol, maltose, and at least one other carbohydrate;
90. at least one polyol, invert sugar, and at least one other carbohydrate;
91. at least one polyol, trehalose, and at least one other carbohydrate;
92. at least one polyol, isotrehalose, and at least one other carbohydrate;
93. at least one polyol, neotrehalose, and at least one other carbohydrate;
94. at least one polyol, palatinose, and at least one other carbohydrate;
95. at least one polyol, galactose, and at least one other carbohydrate;
96. at least one polyol, beet oligosaccharides, and at least one other carbohydrate;
97. at least one polyol, isomalto-oligosaccharides, and at least one other carbohydrate;
98. at least one polyol, isomaltose, and at least one other carbohydrate;
99. at least one polyol, isomaltotriose, and at least one other carbohydrate;
100. at least one polyol, panose, and at least one other carbohydrate;
101. at least one polyol, xylo-oligosaccharides, and at least one other carbohydrate;
102. at least one polyol, xylotriose, and at least one other carbohydrate;
103. at least one polyol, xylobiose, and at least one other carbohydrate;
104. at least one polyol, gentio-oligoscaccharides, and at least one other carbohydrate;
105. at least one polyol, gentiobiose, and at least one other carbohydrate;

106. at least one polyol, gentiotriose, and at least one other carbohydrate;
107. at least one polyol, gentiotetraose, and at least one other carbohydrate;
108. at least one polyol, sorbose, and at least one other carbohydrate;
109. at least one polyol, nigero-oligosaccharides, and at least one other carbohydrate;
110. at least one polyol, palatinose oligosaccharides, and at least one other carbohydrate;
111. at least one polyol, fucose, and at least one other carbohydrate;
112. at least one polyol, fructooligosaccharides, and at least one other carbohydrate;
113. at least one polyol, kestose, and at least one other carbohydrate;
114. at least one polyol, nystose, and at least one other carbohydrate;
115. at least one polyol, maltotetraol, and at least one other carbohydrate;
116. at least one polyol, maltotriol, and at least one other carbohydrate;
117. at least one polyol, malto-oligosaccharides, and at least one other carbohydrate;
118. at least one polyol, maltotriose, and at least one other carbohydrate;
119. at least one polyol, maltotetraose, and at least one other carbohydrate;
120. at least one polyol, maltopentaose, and at least one other carbohydrate;
121. at least one polyol, maltohexaose, and at least one other carbohydrate;
122. at least one polyol, maltoheptaose, and at least one other carbohydrate;
123. at least one polyol, lactulose, and at least one other carbohydrate;
124. at least one polyol, melibiose, and at least one other carbohydrate;
125. at least one polyol, raffinose, and at least one other carbohydrate;
126. at least one polyol, rhamnose, and at least one other carbohydrate;
127. at least one polyol, ribose, and at least one other carbohydrate;
128. at least one polyol, isomerized liquid sugars, and at least one other carbohydrate;
129. at least one polyol, high fructose corn syrup (e.g. HFCS55, HFCS42, or HFCS90) or starch syrup, and at least one other carbohydrate;
130. at least one polyol, coupling sugars, and at least one other carbohydrate;
131. at least one polyol, soybean oligosaccharides, and at least one other carbohydrate;
132. at least one polyol, glucose syrup, and at least one other carbohydrate;
133. at least one carbohydrate and erythritol;
134. at least one carbohydrate and maltitol;
135. at least one carbohydrate and mannitol;
136. at least one carbohydrate and sorbitol;
137. at least one carbohydrate and lactitol;
138. at least one carbohydrate and xylitol;
139. at least one carbohydrate and isomalt;
140. at least one carbohydrate and propylene glycol;
141. at least one carbohydrate and glycerol;
142. at least one carbohydrate and palatinose;
143. at least one carbohydrate and reduced isomalto-oligosaccharides;
144. at least one carbohydrate and reduced xylo-oligosaccharides;
145. at least one carbohydrate and reduced gentio-oligosaccharides;
146. at least one carbohydrate and reduced maltose syrup;
147. at least one carbohydrate and reduced glucose syrup;
148. at least one carbohydrate, erythritol, and at least one other polyol;
149. at least one carbohydrate, maltitol, and at least one other polyol;
150. at least one carbohydrate, mannitol, and at least one other polyol;
151. at least one carbohydrate, sorbitol, and at least one other polyol;
152. at least one carbohydrate, lactitol, and at least one other polyol,
153. at least one carbohydrate, xylitol, and at least one other polyol;
154. at least one carbohydrate, isomalt, and at least one other polyol;
155. at least one carbohydrate, propylene glycol, and at least one other polyol;
156. at least one carbohydrate, glycerol, and at least one other polyol;
157. at least one carbohydrate, palatinose, and at least one other polyol;
158. at least one carbohydrate, reduced isomalto-oligosaccharides, and at least one other polyol;
159. at least one carbohydrate, reduced xvlo-oligosaccharides, and at least one other polyol;
160. at least one carbohydrate, reduced gentio-oligosaccharides, and at least one other polyol;
161. at least one carbohydrate, reduced maltose syrup, and at least one other polyol; and
162. at least one carbohydrate, reduced glucose syrup, and at least one other polyol.

Other sweet taste improving composition combinations in accordance with embodiments of this invention include:
1. at least one carbohydrate and at least one amino acid;
2. at least one carbohydrate and at least one polyamino acid;
3. at least one carbohydrate and at least one sugar acid;
4. at least one carbohydrate and at least one nucleotide;
5. at least one carbohydrate and at least one organic acid;
6. at least one carbohydrate and at least one inorganic acid;
7. at least one carbohydrate and at least one bitter compound;
8. at least one carbohydrate and at least one flavorant or flavoring ingredient;
9. at least one carbohydrate and at least one polymer;
10. at least one carbohydrate and at least one protein or protein hydrolysate;
11. at least one carbohydrate and at least one surfactant;
12. at least one carbohydrate and at least one flavonoid;
13. at least one carbohydrate and at least one alcohol;
14. at least one carbohydrate and at least one protein or protein hydrolysate or mixture of low molecular weight amino acids;
15. at least one carbohydrate and at least one emulsifier;
16. at least one carbohydrate and at least one inorganic salt;
17. at least one carbohydrate, at least one amino acid, and at least one other sweet taste improving additive;
18. at least one carbohydrate, at least one polyamino acid, and at least one other sweet taste improving additive;
19. at least one carbohydrate, at least one sugar acid, and at least one other sweet taste improving additive;

20. at least one carbohydrate, at least one nucleotide, and at least one other sweet taste improving additive;
21. at least one carbohydrate, at least one organic acid, and at least one other sweet taste improving additive;
22. at least one carbohydrate, at least one inorganic acid, and at least one other sweet taste improving additive;
23. at least one carbohydrate, at least one bitter compound, and at least one other sweet taste improving additive;
24. at least one carbohydrate, at least one flavorant or flavoring ingredient, and at least one other sweet taste improving additive;
25. at least one carbohydrate, at least one polymer, and at least one other sweet taste improving additive;
26. at least one carbohydrate, at least one protein or protein hydrolysate, and at least one other sweet taste improving additive;
27. at least one carbohydrate, at least one surfactant, and at least one other sweet taste improving additive;
28. at least one carbohydrate, at least one flavonoid, and at least one other sweet taste improving additive;
29. at least one carbohydrate, at least one alcohol, and at least one other sweet taste improving additive;
30. at least one carbohydrate, at least one amino acid, and at least one polyamino acid;
31. at least one carbohydrate, at least one amino acid, at least one polyamino acid, and at least one sugar acid;
32. at least one carbohydrate, at least one amino acid, at least one polyamino acid, at least one sugar acid, and at least one nucleotide;
33. at least one carbohydrate, at least one amino acid, at least one polyamino acid, at least one sugar acid, at least one nucleotide, and at least one organic acid;
34. at least one carbohydrate, at least one amino acid, at least one polyamino acid, at least one sugar acid, at least one nucleotide, at least one organic acid, and at least one inorganic acid;
35. at least one carbohydrate, at least one amino acid, at least one polyamino acid, at least one sugar acid, at least one nucleotide, at least one organic acid, at least one inorganic acid, and at least one bitter compound;
36. at least one carbohydrate, at least one amino acid, at least one polyamino acid, at least one sugar acid, at least one nucleotide, at least one organic acid, at least one inorganic acid, at least one bitter compound, and at least one polymer;
37. at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
40. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
41. at least one carbohydrate, at least one amino acid, and at least one sugar acid;
42. at least one carbohydrate, at least one amino acid, and at least one nucleotide;
43. at least one carbohydrate, at least one amino acid, and at least one organic acid;
44. at least one carbohydrate, at least one amino acid, and at least one inorganic acid;
45. at least one carbohydrate, at least one amino acid, and at least one bitter compound;
46. at least one carbohydrate, at least one amino acid, and at least one polymer;
47. at least one carbohydrate, at least one amino acid, and at least one protein or protein hydrolysate;
48. at least one carbohydrate, at least one amino acid, and at least one surfactant;
49. at least one carbohydrate, at least one amino acid, and at least one flavonoid;
50. at least one carbohydrate, at least one amino acid, and at least one alcohol;
51. at least one carbohydrate, at least one polyamino acid, and at least one sugar acid;
52. at least one carbohydrate, at least one polyamino acid, and at least one nucleotide;
53. at least one carbohydrate, at least one polyamino acid, and at least one organic acid;
54. at least one carbohydrate, at least one polyamino acid, and at least one inorganic acid;
55. at least one carbohydrate, at least one polyamino acid, and at least one bitter compound;
56. at least one carbohydrate, at least one polyamino acid, and at least one polymer;
57. at least one carbohydrate, at least one polyamino acid, and at least one protein or protein hydrolysate;
58. at least one carbohydrate, at least one polyamino acid, and at least one surfactant;
59. at least one carbohydrate, at least one polyamino acid, and at least one flavonoid;
60. at least one carbohydrate, at least one polyamino acid, and at least one alcohol;
61. at least one carbohydrate, at least one sugar acid, and at least one nucleotide;
62. at least one carbohydrate, at least one sugar acid, and at least one organic acid;
63. at least one carbohydrate, at least one sugar acid, and at least one inorganic acid;
64. at least one carbohydrate, at least one sugar acid, and at least one bitter compound;
65. at least one carbohydrate, at least one sugar acid, and at least one polymer;
66. at least one carbohydrate, at least one sugar acid, and at least one protein or protein hydrolysate;
67. at least one carbohydrate, at least one sugar acid, and at least one surfactant;
68. at least one carbohydrate, at least one sugar acid, and at least one flavonoid;
69. at least one carbohydrate, at least one sugar acid, and at least one alcohol;
70. at least one carbohydrate, at least one nucleotide, and at least one organic acid;
71. at least one carbohydrate, at least one nucleotide, and at least one inorganic acid;
72. at least one carbohydrate, at least one nucleotide, and at least one bitter compound;

73. at least one carbohydrate, at least one nucleotide, and at least one polymer;
74. at least one carbohydrate, at least one nucleotide, and at least one protein or protein hydrolysate;
75. at least one carbohydrate, at least one nucleotide, and at least one surfactant;
76. at least one carbohydrate, at least one nucleotide, and at least one flavonoid;
77. at least one carbohydrate, at least one nucleotide, and at least one alcohol;
78. at least one carbohydrate, at least one organic acid, and at least one inorganic acid;
79. at least one carbohydrate, at least one organic acid, and at least one bitter compound;
80. at least one carbohydrate, at least one organic acid, and at least one polymer;
81. at least one carbohydrate, at least one organic acid, and at least one protein or protein hydrolysate;
82. at least one carbohydrate, at least one organic acid, and at least one surfactant;
83. at least one carbohydrate, at least one organic acid, and at least one favonoid;
84. at least one carbohydrate, at least one organic acid, and at least one alcohol;
85. at least one carbohydrate, at least one inorganic acid, and at least one bitter compound;
86. at least one carbohydrate, at least one inorganic acid, and at least one polymer;
87. at least one carbohydrate, at least one inorganic acid, and at least one protein or protein hydrolysate;
88. at least one carbohydrate, at least one inorganic acid, and at least one surfactant;
89. at least one carbohydrate, at least one inorganic acid, and at least one flavonoid;
90. at least one carbohydrate, at least one inorganic acid, and at least one alcohol;
91 at least one carbohydrate, at least one bitter compound, and at least one polymer;
92. at least one carbohydrate, at least one bitter compound, and at least one protein or protein hydrolysate;
93. at least one carbohydrate, at least one bitter compound, and at least one surfactant;
94. at least one carbohydrate, at least one bitter compound, and at least one flavonoid;
95. at least one carbohydrate, at least one bitter compound, and at least one alcohol;
96. at least one carbohydrate, at least one polymer, and at least one protein or protein hydrolysate;
97. at least one carbohydrate, at least one polymer, and at least one surfactant;
98. at least one carbohydrate, at least one polymer, and at least one flavonoid;
99. at least one carbohydrate, at least one polymer, and at least one alcohol;
100. at least one carbohydrate, at least one protein or protein hydrolysate, and at least one surfactant;
101. at least one carbohydrate, at least one protein or protein hydrolysate, and at least one lavonoid;
102. at least one carbohydrate, at least one surfactant, and at least one flavonoid;
103. at least one carbohydrate, at least one surfactant, and at least one alcohol;
104. at least one carbohydrate, at least one flavonoid, and at least one alcohol;
105. at least one sweet taste improving additive and D-tagatose;
106. at least one sweet taste improving additive and trehalose;
107. at least one sweet taste improving additive and D-galactose;
108. at least one sweet taste improving additive and rhamnose;
109. at least one sweet taste improving additive and dextrin,
110. at least one sweet taste improving additive and cyclodextrin;
111. at least one sweet taste improving additive and β-cyclodextrin;
112. at least one sweet taste improving additive and maltodextrin;
113. at least one sweet taste improving additive and dextran;
114. at least one sweet taste improving additive and sucrose;
115. at least one sweet taste improving additive and glucose;
116. at least one sweet taste improving additive and fructose;
117. at least one sweet taste improving additive and threose;
118. at least one sweet taste improving additive and arabinose;
119. at least one sweet taste improving additive and xylose;
120. at least one sweet taste improving additive and lyxose;
121. at least one sweet taste improving additive and allose;
122. at least one sweet taste improving additive and altrose;
123. at least one sweet taste improving additive and mannose;
124. at least one sweet taste improving additive and idose;
125. at least one sweet taste improving additive and talose;
126. at least one sweet taste improving additive and lactose;
127. at least one sweet taste improving additive and maltose;
128. at least one sweet taste improving additive and invert sugar;
129. at least one sweet taste improving additive and trehalose;
130. at least one sweet taste improving additive and isotrehalose;
131. at least one sweet taste improving additive and neotrehalose;
132. at least one sweet taste improving additive and palatinose;
133. at least one sweet taste improving additive and galactose;
134. at least one sweet taste improving additive and beet oligosaccharides; 135. at least one sweet taste improving additive and isomalto-oligosaccharides;
136. at least one sweet taste improving additive and isomaltose;
137. at least one sweet taste improving additive and isomaltotriose;
138. at least one sweet taste improving additive and panose;
139. at least one sweet taste improving additive and xylo-oligosaccharides;
140. at least one sweet taste improving additive and xylotriose;
141. at least one sweet taste improving additive and xylobiose;
142. at least one sweet taste improving additive and gentio-oligosaccaccharides;

143. at least one sweet taste improving additive and gentiobiose;
144. at least one sweet taste improving additive and gentiotriose;
145. at least one sweet taste improving additive and gentiotetraose;
146. at least one sweet taste improving additive and sorbose;
147. at least one sweet taste improving additive and nigero-oligosaccharides;
148. at least one sweet taste improving additive and palatinose oligosaccharides;
149. at least one sweet taste improving additive and fucose;
150. at least one sweet taste improving additive and fructooligosaccharides;
151. at least one sweet taste improving additive and kestose;
152. at least one sweet taste improving additive and nystose;
153. at least one sweet taste improving additive and maltotetraol;
154. at least one sweet taste improving additive and maltotriol;
155. at least one sweet taste improving additive and maltooligosaccharides;
156. at least one sweet taste improving additive and maltotriose;
157. at least one sweet taste improving additive and maltotetraose;
158. at least one sweet taste improving additive and maltopentaose;
159. at least one sweet taste improving additive and maltohexaose;
160. at least one sweet taste improving additive and maltoheptaose;
161. at least one sweet taste improving additive and lactulose;
162. at least one sweet taste improving additive and melibiose;
163. at least one sweet taste improving additive and raffinose;
164. at least one sweet taste improving additive and rhamnose;
165. at least one sweet taste improving additive and ribose;
166. at least one sweet taste improving additive and isomerized liquid sugars;
167. at least one sweet taste improving additive and high fructose corn syrup (e.g., HFCS55, HFCS42, or HFCS90) or starch syrup;
168. at least one sweet taste improving additive and coupling sugars;
169. at least one sweet taste improving additive and soybean oligosaccharides;
170. at least one sweet taste improving additive and glucose syrup;
171. at least one sweet taste improving additive, D-tagatose, and at least one other carbohydrate;
172. at least one sweet taste improving additive, trehalose, and at least one other carbohydrate;
173. at least one sweet taste improving additive, D-galactose, and at least one other carbohydrate;
174. at least one sweet taste improving additive, rhamnose, and at least one other carbohydrate;
175. at least one sweet taste improving additive, dextrin, and at least one other carbohydrate;
176. at least one sweet taste improving additive, cyclodextrin, and at least one other carbohydrate;
177. at least one sweet taste improving additive, β-cyclodextrin, and at least one other carbohydrate;
178. at least one sweet taste improving additive, maltodextrin, and at least one other carbohydrate;
179. at least one sweet taste improving additive, dextran, and at least one other carbohydrate;
180. at least one sweet taste improving additive, sucrose, and at least one other carbohydrate;
181. at least one sweet taste improving additive, glucose, and at least one other carbohydrate;
182. at least one sweet taste improving additive, fructose, and at least one other carbohydrate;
183 at least one sweet taste improving additive, threose, and at least one other carbohydrate;
184. at least one sweet taste improving additive, arabinose, and at least one other carbohydrate;
185. at least one sweet taste improving additive, xylose, and at least one other carbohydrate:
186. at least one sweet taste improving additive, lyxose, and at least one other carbohydrate;
187. at least one sweet taste improving additive, allose, and at least one other carbohydrate;
188. at least one sweet taste improving additive, altrose, and at least one other carbohydrate;
189. at least one sweet taste improving additive, mannose, and at least one other carbohydrate;
190. at least one sweet taste improving additive, idose, and at least one other carbohydrate;
191. at least one sweet taste improving additive, talose, and at least one other carbohydrate;
192. at least one sweet taste improving additive, lactose, and at least one other carbohydrate;
193. at least one sweet taste improving additive, maltose, and at least one other carbohydrate;
194. at least one sweet taste improving additive, invert sugar, and at least one other carbohydrate;
195. at least one sweet taste improving additive, trehalose, and at least one other carbohydrate;
196. at least one sweet taste improving additive, isotrehalose, and at least one other carbohydrate;
197. at least one sweet taste improving additive, neotrehalose, and at least one other carbohydrate;
198. at least one sweet taste improving additive, palatinose, and at least one other carbohydrate;
199. at least one sweet taste improving additive, galactose, and at least one other carbohydrate;
200. at least one sweet taste improving additive, beet oligosaccharides, and at least one other carbohydrate;
201. at least one sweet taste improving additive, isomaltooligosaccharides, and at least one other carbohydrate;
202. at least one sweet taste improving additive, isomaltose, and at least one other carbohydrate;
203. at least one sweet taste improving additive, isomaltotriose, and at least one other carbohydrate;
204. at least one sweet taste improving additive, panose, and at least one other carbohydrate;
205. at least one sweet taste improving additive, xylooligosaccharides, and at least one other carbohydrate;
206. at least one sweet taste improving additive, xylotriose, and at least one other carbohydrate;
207. at least one sweet taste improving additive, xylobiose, and at least one other carbohydrate;
208. at least one sweet taste improving additive, gentiooligoscaccharides, and at least one other carbohydrate;
209. at least one sweet taste improving additive, gentiobiose, and at least one other carbohydrate;

210. at least one sweet taste improving additive, gentiotriose, and at least one other carbohydrate;
211. at least one sweet taste improving additive, gentiotetraose, and at least one other carbohydrate;
212. at least one sweet taste improving additive, sorbose, and at least one other carbohydrate;
213. at least one sweet taste improving additive, nigero-oligosaccharides, and at least one other carbohydrate;
214. at least one sweet taste improving additive, palatinose oligosaccharides, and at least one other carbohydrate;
215. at least one sweet taste improving additive, fucose, and at least one other carbohydrate;
216. at least one sweet taste improving additive, fructooligosaccharides, and at least one other carbohydrate;
217. at least one sweet taste improving additive, kestose, and at least one other carbohydrate;
218. at least one sweet taste improving additive, nystose, and at least one other carbohydrate;
219. at least one sweet taste improving additive, maltotetraol, and at least one other carbohydrate;
220. at least one sweet taste improving additive, maltotriol, and at least one other carbohydrate;
221. at least one sweet taste improving additive, malto-oligosaccharides, and at least one other carbohydrate;
222. at least one sweet taste improving additive, maltotriose, and at least one other carbohydrate;
223. at least one sweet taste improving additive, maltotetraose, and at least one other carbohydrate;
224. at least one sweet taste improving additive, maltopentaose, and at least one other carbohydrate;
225. at least one sweet taste improving additive, maltohexaose, and at least one other carbohydrate;
226. at least one sweet taste improving additive, maltoheptaose, and at least one other carbohydrate;
227. at least one sweet taste improving additive, lactulose, and at least one other carbohydrate;
228. at least one sweet taste improving additive, melibiose, and at least one other carbohydrate;
229. at least one sweet taste improving additive, raffinose, and at least one other carbohydrate;
230. at least one sweet taste improving additive, rhamnose, and at least one other carbohydrate;
231. at least one sweet taste improving additive, ribose, and at least one other carbohydrate;
232. at least one sweet taste improving additive, isomerized liquid sugars, and at least one other carbohydrate;
233. at least one sweet taste improving additive, high fructose corn syrup (e.g. HFCS55, HFCS42, or HFCS90) or starch syrup, and at least one other carbohydrate;
234. at least one sweet taste improving additive, coupling sugars, and at least one other carbohydrate;
235. at least one sweet taste improving additive, soybean oligosaccharides, and at least one other carbohydrate; and
236. at least one sweet taste improving additive, glucose syrup, and at least one other carbohydrate.

In another embodiment, the condiment composition comprises at least one natural and/or synthetic high-potency sweetener and a condiment base in combination with a plurality of sweet taste improving additives, desirably 3 or more sweet taste improving additives, and even more desirably 4 or more sweet taste improving additives, wherein each sweet taste improving additive is present in an amount such that no one sweet taste improving additive imparts a substantial off taste to the sweetener composition. In other words, the amounts of the sweet taste improving additives in the sweetener composition are balanced so that no one sweet taste improving additive imparts a substantial off taste to the sweetener composition.

According to a particular embodiment of this invention, the sweetener composition provided herein comprises at least one sweet taste improving composition in the sweetener composition in an amount effective for the sweetener composition to impart an osmolarity of at least 10 mOsmoles/L to an aqueous solution of the sweetener composition, wherein the at least one natural and/or synthetic high-potency sweetener is present in the aqueous solution in an amount sufficient to impart a maximum sweetness intensity equivalent to that of a 10% aqueous solution of sucrose by weight. As used herein, "mOsmoles/L" refers to milliosmoles per liter. According to another embodiment, the sweetener composition comprises at least one sweet taste improving composition in an amount effective for the sweetener composition to impart an osmolarity of 10 to 500 mOsmoles/L, preferably 25 to 500 mOsmoles/L preferably, more preferably 100 to 500 mOsmoles/L, more preferably 200 to 500 mOsmoles/L, and still more preferably 300 to 500 mOsmoles/L to an aqueous solution of the sweetener composition, wherein the at least one natural and/or synthetic high-potency sweetener is present in the aqueous solution in an amount sufficient to impart a maximum sweetness intensity equivalent to that of a 10% aqueous solution of sucrose by weight. Wherein a plurality of sweet taste improving compositions are combined with at least one natural and/or synthetic high-potency sweetener, the osmolarity imparted is that of the total combination of the plurality of sweet taste improving compositions.

Osmolarity refers to the measure of osmoles of solute per liter of solution, wherein osmole is equal to the number of moles of osmotically active particles in an ideal solution (e.g., a mole of glucose is one osmole), whereas a mole of sodium chloride is two osmoles (one mole of sodium and one mole of chloride). Thus, in order to improve in the quality of taste of the sweetener composition, the osmotically active compounds or the compounds which impart osmolarity must not introduce significant off taste to the formulation.

In one embodiment, suitable sweet taste improving carbohydrate additives for the present invention have a molecular weight less than or equal to 500 and desirably have a molecular weight from 50 to 500. In particular embodiments, suitable carbohydrates with a molecular weight less than or equal to 500 include, but are not limited to, sucrose, fructose, glucose, maltose, lactose, mannose, galactose, and tagatose. Generally, in accordance with desirable embodiments of this invention, a sweet taste improving carbohydrate additive is present in the sweetener compositions in an amount from about 1,000 to about 100,000 ppm. (Throughout this specification, the term ppm means parts per million by weight or volume. For example, 500 ppm means 500 mg in a liter.) In accordance with other desirable embodiments of this invention, a sweet taste improving carbohydrate additive is present in the sweetened compositions in an amount from about 2,500 to about 10,000 ppm. In another embodiment, suitable sweet taste improving carbohydrate additives for imparting osmolarities ranging from about 10 mOsmoles/IL to about 500 mOsmoles/L to a sweetenable composition include, but are not limited to, sweet taste improving carbohydrate additives with a molecular weight ranging from about 50 to about 500.

In one embodiment, suitable sweet taste improving polyol additives have a molecular weight less than or equal to 500 and desirably have a molecular weight from 76 to 500. In particular embodiments, suitable sweet taste improving polyol additives with a molecular weight less than or equal to 500 include, but are not limited to, erythritol, glycerol, and propylene glycol. Generally, in accordance with desirable embodiments of this invention, a sweet taste improving polyol additive is present in the sweetener compositions in an amount from about 100 ppm to about 80,000 ppm. In accordance with other desirable embodiments of this invention, a sweet taste improving polyol additive is present in sweetened compositions in an amount from about 400 to about 80,000 ppm. In a sub-embodiment, suitable sweet taste improving polyol additives for imparting osmolarities ranging from about 10 mOsmoles/L to about 500 mOsmoles/L to a sweetenable composition include, but are not limited to, sweet taste improving polyol additives with a molecular weight ranging from about 76 to about 500.

In accordance with still other desirable embodiments of this invention, a sweet taste improving polyol additive is present in sweetener compositions in an amount from about 400 to about 80,000 ppm of the total sweetener composition, more particularly from about about 5,000 to about 40,000 ppm, and still more particularly from about 10,000 to about 35,000 ppm. Desirably, the at least one natural and/or synthetic high-potency sweetener and at least one sweet taste improving polyol additive are present in the sweetener composition in a ratio from about 1:4 to about 1:800, respectively; more particularly from about 1:20 to about 1:600; even more particularly from about 1:50 to about 1:300; and still more particularly from about 1:75 to about 1:150.

Generally, in accordance with another embodiment of this invention, a suitable sweet taste improving alcohol additive is present in the sweetener compositions in an amount from about 625 to about 10,000 ppm. In another embodiment, suitable sweet taste improving alcohol additives for imparting osmolarities ranging from about 10 mOsmoles/L to about 500 mOsmoles/L to a sweetenable composition include, but are not limited to, sweet taste improving alcohol additives with a molecular weight ranging from about 46 to about 500. A non-limiting example of sweet taste improving alcohol additive with a molecular weight ranging from about 46 to about 500 includes ethanol.

In one embodiment, suitable sweet taste improving amino acid additives have a molecular weight of less than or equal to 250 and desirably have a molecular weight from 75 to 250. In particular embodiments, suitable sweet taste improving amino acid additives with a molecular weight less than or equal to 250 include, but are not limited to, glycine, alanine, serine, valine, leucine, isoleucine, proline, theanine, and threonine. Preferred sweet taste improving amino acid additives include those which are sweet tasting at high concentrations, but desirably are present in embodiments of this invention at amounts below or above their sweetness taste detection threshold. Even more preferred are mixtures of sweet taste improving amino acid additives at amounts below or above their sweetness taste detection threshold. Generally, in accordance with desirable embodiments of this invention, a sweet taste improving amino acid additive is present in the sweetener compositions in an amount from about 100 ppm to about 25,000 ppm, more particularly from about 1,000 to about 10,000 ppm, and still more particularly from about 2,500 to about 5,000 ppm. In accordance with other desirable embodiments of this invention, a sweet taste improving amino acid additive is present in the sweetened compositions in an amount from about 250 ppm to about 7,500 ppm. In a sub-embodiment, suitable sweet taste improving amino acid additives for imparting osmolarities ranging from about 10 mOsmoles/L to about 500 mOsmoles/L to a sweetenable composition include, but are not limited to, sweet taste improving amino acid additives with a molecular weight ranging from about 75 to about 250.

Generally, in accordance with yet another embodiment of this invention, a suitable sweet taste improving amino acid salt additive is present in the sweetener compositions in an amount from about 25 to about 10,000 ppm, more particularly from about 1,000 to about 7,500 ppm, and still more particularly from about 2,500 to about 5,000 ppm. In another embodiment, suitable sweet taste improving amino acid salt additives for imparting osmolarities ranging from about 10 mOsmoles/L to about 500 mOsmoles/L to a sweetenable composition include, but are not limited to, sweet taste improving amino acid salt additives with a molecular weight ranging from about 75 to about 300. Non-limiting examples of sweet taste improving amino acid salt additives with a molecular weight ranging from about 75 to about 300 include salts of glycine, alanine, serine, theanine, and threonine.

Generally, in accordance with still another embodiment of this invention, a suitable sweet taste improving protein or protein hydroyslate additive is present in the sweetener compositions in an amount from about 200 to about 50,000 ppm. In another embodiment, suitable sweet taste improving protein or protein hydrolysate additives for imparting osmolarities ranging from about 10 mOsmoles/L to about 500 mOsmoles/L to a sweetenable composition include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include proteins or protein hydrolysates containing glycine, alanine, serine, and threonine.

Generally, in accordance with another embodiment of this invention, a suitable sweet taste improving inorganic acid additive is present in the sweetener compositions in an amount from about 25 to about 5,000 ppm. In another embodiment, suitable sweet taste improving inorganic acid additives for imparting osmolarities ranging from about 10 mOsmoles/L to about 500 mOsmoles/L to a sweetenable composition include, but are not limited to, phosphoric acid, HCl, and $H_2SO_4$ and any other inorganic acid additives which are safe for human or animal consumption when used in a generally acceptable range. In a sub-embodiment, suitable sweet taste improving inorganic acid additives for imparting osmolarities ranging from about 10 mOsmoles/L to about 500 mOsmoles/L to a sweetenable composition include, but are not limited to, sweet taste improving inorganic acid additives with a molecular weight range from about 36 to about 98.

Generally, in accordance with still another embodiment of this invention, a suitable sweet taste improving inorganic acid salt additive is present in the sweetener compositions in an amount from about 25 to about 5,000 ppm. In another embodiment, suitable sweet taste improving inorganic acid salt additives for imparting osmolarities ranging from about 10 mOsmoles/L to about 500 mOsmoles/L to a sweetenable composition include, but are not limited to, salts of inorganic acids, for example sodium, potassium, calcium, and magnesium salts of phosphoric acid, and any other alkali or alkaline earth metal salts of other inorganic acids (e.g., sodium bisulfate) which are safe for human or animal consumption when used in a generally acceptable range. In a sub-embodiment, suitable suitable sweet taste improving inorganic acid salt additives for imparting osmolarities ranging from about 10 mOsmoles/L to about 500 mOsmoles/L to a sweetenable composition include, but are not limited to, sweet taste improving inorganic acid salt additives with a molecular weight range from about 58 to about 120.

Generally, in accordance with still another embodiment of this invention, a suitable sweet taste improving organic acid additive is present in the sweetener compositions in an amount from about 10 to about 5,000 ppm. In another embodiment, suitable sweet taste improving organic acid additives for imparting osmolarities ranging from about 10 mOsmoles/L to about 500 mOsmoles/L to a sweetenable composition include, but are not limited to, creatine, citric acid, malic acid, succinic acid, hydroxycitric acid, tartaric acid, fumaric acid, gluconic acid, glutaric acid, adipic acid, and any other sweet taste improving organic acid additives which are safe for human or animal consumption when used in a generally acceptable range. In one embodiment, the sweet taste improving organic acid additive comprises a molecular weight range from about 60 to about 208.

Generally, in accordance with still another embodiment of this invention, a suitable sweet taste improving organic acid salt additive is present in the sweetener compositions in an amount from about 20 to about 10,000 ppm. In another embodiment, suitable sweet taste improving organic acid salt additives for imparting osmolarities ranging from about 10 mOsmoles/L to about 500 mOsmoles/L to a sweetenable composition include, but are not limited to, salts of sweet taste improving organic acid additives, such as sodium, potassium, calcium, magnesium, and other alkali or alkaline metal salts of citric acid, malic acid, tartaric acid, fumaric acid, gluconic acid, glutaric acid, adipic acid, hydroxycitric acid, succinic acid, and salts of any other sweet taste improving organic acid additives which are safe for human or animal consumption when used in a generally acceptable range. In one embodiment, the sweet taste improving organic acid salt additive comprises a molecular weight range from about 140 to about 208.

Generally, in accordance with yet another embodiment of this invention, a suitable sweet taste improving organic base salt additive is present in the sweetener compositions in an amount from about 10 to about 5,000 ppm. In another embodiment, suitable sweet taste improving organic base salt additives for imparting osmolarities ranging from about 10 mOsmoles/L to about 500 mOsmoles/L to a sweetenable composition include, but are not limited to, inorganic and organic acid salts of organic bases such as glucosamine salts, choline salts, and guanidine salts.

Generally, in accordance with yet another embodiment of this invention, a suitable sweet taste improving astringent additive is present in the sweetener compositions in an amount from about 25 to about 1,000 ppm. In another embodiment, suitable sweet taste improving astringent additives for imparting osmolarities ranging from about 10 mOsmoles/L to about 500 mOsmoleslL to a sweetenable composition include, but are not limited to, tannic acid, tea polyphenols, catechins, aluminum sulfate, $AlNa(SO_4)_2$, $AlK(SO_4)_2$ and other forms of alum.

Generally, in accordance with yet another embodiment of this invention, a suitable sweet taste improving nucleotide additive is present in the sweetener compositions in an amount from about 5 to about 1,000 ppm. In another embodiment, suitable sweet taste improving nucleotide additives for imparting osmolarities ranging from about 10 mOsmoles/L to about 500 mOsmoles/L to a sweetenable composition include, but are not limited to, adenosine monophosphate.

Generally, in accordance with yet another embodiment of this invention, a suitable sweet taste improving polyamino acid additive is present in the sweetener compositions in an amount from about 30 to about 2,000 ppm. In another embodiment, suitable sweet taste improving polyamino acid additives for imparting osmolarities ranging from about 10 mOsmoles/L to about 500 mOsmoles/L to a sweetenable composition include, but are not limited to, poly-L-lysine (e.g., poly-L-α-lysine or poly-L-ε-lysine), poly-L-ornithine (e.g., poly-L-α-ornithine or poly-L-ε-ornithine), and poly-L-arginine.

Generally, in accordance with yet another embodiment of this invention, a suitable sweet taste improving polymer additive is present in the sweetener compositions in an amount from about 30 to about 2,000 ppm. In another embodiment, suitable sweet taste improving polymer additives for imparting osmolarities ranging from about 10 mOsmoles/L to about 500 mOsmoles/L to a sweetenable composition include, but are not limited to, chitosan, sodium hexametaphosphate and its salts, pectin, hydrocolloids such as gum acacia senegal, propylene glycol, polyethylene glycol, and poly(ethylene glycol methyl ether).

Generally, in accordance with yet another embodiment of this invention, a suitable sweet taste improving surfactant additive is present in the sweetener compositions in an amount from about 1 to about 5,000 ppm. In another embodiment, suitable sweet taste improving surfactant additives for imparting osmolarities ranging from about 10 mOsmoles/L to about 500 mOsmoles/L to a sweetenable composition include, but are not limited to, polysorbates, choline chloride, sodium taurocholate, lecithins, sucrose oleate esters, sucrose stearate esters, sucrose palmitate esters, and sucrlose laurate esters.

Generally, in accordance with yet another embodiment of this invention, a suitable sweet taste improving flavonoid additive is present in the sweetener compositions in an amount from about 0.1 to about 1,000 ppm. In another embodiment, suitable sweet taste improving flavonoid additives for imparting osmolarities ranging from about 10 mOsmoles/L to about 500 mOsmoles/L to a sweetenable composition include, but are not limited to, naringin, catechins, rutins, neohesperidin, and neohesperidin dihydrochalcone.

In a preferred embodiment, non-limiting examples of sweet taste improving compositions enhancing the natural and/or synthetic high-potency sweetener's osmotic taste to be more sugar-like include sweet taste improving carbohydrate additives, sweet taste improving alcohol additives, sweet taste improving polyol additives, sweet taste improving amino acid additives, sweet taste improving amino acid salt additives, sweet taste improving inorganic acid salt additives, sweet taste improving polymer additives, and sweet taste improving protein or protein hydrolysate additives.

In another embodiment, suitable sweet taste improving carbohydrate additives for improving the osmotic taste of the natural and/or synthetic high-potency sweetener to be more sugar-like include, but are not limited to, sweet taste improving carbohydrate additives with a molecular weight ranging from about 50 to about 500. Non-limiting examples of sweet taste improving carbohydrate additives with a molecular weight ranging from about 50 to about 500 include sucrose, fructose, glucose, maltose, lactose, mannose, galactose, ribose, rhamnose, trehalose, HFCS, and tagatose.

In another embodiment, suitable sweet taste improving polyol additives for improving the osmotic taste of natural and/or synthetic high-potency sweetener to be more sugar-like include, but are not limited to, sweet taste improving polyol additives with a molecular weight ranging from about 76 to about 500. Non-limiting examples of sweet taste improving polyol additives with a molecular weight ranging from about 76 to about 500 include erythritol, glycerol, and propylene glycol. In a sub-embodiment, other suitable sweet taste improving polyol additives include sugar alcohols.

In another embodiment, suitable sweet taste improving alcohol additives for improving the osmotic taste of natural and/or synthetic high-potency sweetener to be more sugar-like include, but are not limited to, sweet taste improving alcohol additives with a molecular weight ranging from about 46 to about 500. A non-limiting example of sweet taste improving alcohol additive with a molecular weight ranging from about 46 to about 500 includes ethanol.

In another embodiment, suitable sweet taste improving amino acid additives for improving the osmotic taste of natural and/or synthetic high-potency sweetener to be more sugar-like include, but are not limited to sweet taste improving amino acid additives with a molecular weight ranging from about 75 to about 250. Non-limiting examples of sweet taste improving amino acid additives with a molecular weight ranging from about 75 to about 250 include glycine, alanine, serine, leucine, valine, isoleucine, proline, hydroxyproline, glutamine, theanine, and threonine.

In another embodiment, suitable sweet taste improving amino acid salt additives for improving the osmotic taste of natural and/or synthetic high-potency sweetener to be more sugar-like include, but are not limited to, sweet taste improving amino acid salt additives with a molecular weight ranging from about 75 to about 300. Non-limiting examples of sweet taste improving amino acid salt additives with a molecular weight ranging from about 75 to about 300 include salts of glycine, alanine, serine, leucine, valine, isoleucine, proline, hydroxyproline, glutamine, theanine, and threonine.

In another embodiment, suitable sweet taste improving protein or protein hydrolysate additives for improving the osmotic taste of natural and/or synthetic high-potency sweetener to be more sugar-like include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include protein or protein hydrolysates containing glycine, alanine, serine, leucine, valine, isoleucine, proline, and threonine.

In another embodiment, suitable sweet taste improving inorganic acid salt additives for improving the osmotic taste of natural and/or synthetic high-potency sweetener to be more sugar-like include, but are not limited to, sodium chloride, potassium chloride, magnesium chloride, $KH_2PO_4$ and $NaH_2PO_4$. Suitable sweet taste improving inorganic acid salt additives for improving the osmotic taste may comprise a molecular weight from about 58 to about 120.

In another embodiment, suitable sweet taste improving bitter additives for improving the osmotic taste of the natural and/or synthetic high-potency sweetener to be more sugar-like include, but are not limited to, caffeine, quinine, urea, quassia, tannic acid, and naringin.

IV. Condiment Compositions

In one embodiment, a condiment composition is provided comprising a condiment base and at least one natural and/or synthetic high-potency sweetener in combination with at least one sweet taste improving nucleotide additive chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof.

In one embodiment, a condiment composition is provided comprising a condiment base and at least one natural and/or synthetic high-potency sweetener in combination with at least one sweet taste improving carbohydrate additive chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup.

In another embodiment, a condiment composition is provided comprising a condiment base and at least one natural and/or synthetic high-potency sweetener in combination with at least one sweet taste improving polyol additive chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a condiment composition is provided comprising a condiment base and at least one natural and/or synthetic high-potency sweetener in combination with at least one sweet taste improving amino acid additive chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving polyamino acid additive chosen from poly-L-aspartic acid, poly-L-lysine (e.g., poly-L-α-lysine or poly-L-ϵ-lysine), poly-L-ornithine (e.g., poly-L-α-omithine or poly-L-ϵ-ornithine), poly-L-arginine, other polymeric forms of amino acids, or salts thereof.

In another embodiment, a condiment composition is provided comprising a condiment base and at least one natural and/or synthetic high-potency sweetener in combination with at least one sweet taste improving sugar acid additive chosen from aldonic, uronic, aldaric, alginic, gluconic, glucuronic, glucaric, galactaric, galacturonic, or salts thereof.

In another embodiment, a condiment composition is provided comprising a condiment base and at least one natural and/or synthetic high-potency sweetener in combination with at least one sweet taste improving organic acid additive chosen from C2-C30 carboxylic acids, substituted hydroxyl C1-C30 carboxylic acids, benzoic acid, substituted benzoic acids (e.g., 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, glutaric acid, creatine, adipic acid, hydroxycitric acid, malic acid, fruitaric acid, fumaric acid, maleic acid, succinic acid, chlorogenic acid, salicylic acid, caffeic acid, bile acids, acetic acid, ascorbic acid, alginic acid, erythorbic acid, polyglutamic acid, or salts thereof.

In another embodiment, a condiment composition is provided comprising a condiment base and at least one natural and/or synthetic high-potency sweetener in combination with at least one sweet taste improving inorganic acid additive chosen from phosphoric acid, phosphorous acid, polyphosphoric acid, hydrochloric acid, sulfuric acid, carbonic acid, sodium dihydrogen phosphate, or salts thereof.

In another embodiment, a condiment composition is provided comprising a condiment base and at least one natural and/or synthetic high-potency sweetener in combination with at least one sweet taste improving bitter compound additive chosen from caffeine, quinine, urea, bitter orange oil, naringin, quassia, or salts thereof.

In another embodiment, a condiment composition is provided comprising a condiment base and at least one natural and/or synthetic high-potency sweetener in combination with at least one sweet taste improving flavorant additive chosen from vanillin, vanilla extract, mango extract, cinnamon, citrus, coconut, ginger, viridiflorol, almond, menthol, grape skin extract, or grape seed extract. In another particular embodiment, the at least one sweet taste improving flavorant additive comprises a proprietary sweetener chosen from Döhler™ Natural Flavoring Sweetness Enhancer K14323 (Döhler™, Darmstadt, Germany), Symrise™ Natural Flavor Mask for Sweeteners 161453 or 164126 (Symrise™, Holzminden, Germany), Natural Advantage™ Bitterness Blockers 1, 2, 9 or 10 (Natural Advantage™, Freehold, N.J., U.S.A.), or Sucramask™ (Creative Research Management, Stockton, Calif., U.S.A.)

In another embodiment, a condiment composition is provided comprising a condiment base and at least one natural and/or synthetic high-potency sweetener in combination with at least one sweet taste improving polymer additive chosen from chitosan, pectin, pectic, pectinic, polyuronic, polygalacturonic acid, starch, food hydrocolloid or crude extracts thereof (e.g., gum acacia senegal, gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly (ethylene glycol methyl ether), polyarginine, polyaspartic acid, polyglutamic acid, polyethyleneimine, alginic acid, sodium alginate, propylene glycol alginate, sodium polyethyleneglycolalginate, sodium hexametaphosphate and its salts, or other cationic and anionic polymers.

In another embodiment, a condiment composition is provided comprising a condiment base and at least one natural and/or synthetic high-potency sweetener in combination with at least one sweet taste improving protein hydrolysate additive chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, theanine, asparagine, glutamine, arginine, valine, isoleucine, leucine, norvaline, methionine, proline, tyrosine, hydroxyproline, or the like).

In another embodiment, a condiment composition is provided comprising a condiment base and at least one natural and/or synthetic high-potency sweetener in combination with at least one sweet taste improving surfactant additive chosen from polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride, hexadecyltrimethyl onium bromide, sodium cholate, carbamoyl, choline chloride, sodium glycocholate, sodium taurocholate, sodium taurodeoxycholate, lauric arginate, sodium stearoyl lactylate, lecithins, sucrose oleate esters, sucrose stearate esters, sucrose palmitate esters, sucrose laurate esters, and other emulsifiers, or the like.

In another embodiment, a condiment composition is provided comprising a condiment base and at least one natural and/or synthetic high-potency sweetener in combination with at least one sweet taste improving flavonoid additive chosen from catechins, polyphenols, rutins, neohesperidin, naringin, neohesperidin dihydrochalcone, or the like.

In another embodiment, a condiment composition is provided comprising a condiment base and at least one natural and/or synthetic high-potency sweetener in combination with ethanol.

In another embodiment, a condiment composition is provided comprising a condiment base and at least one natural and/or synthetic high-potency sweetener in combination with at least one sweet taste improving astringent compound additive chosen from tannic acid, europium chloride ($EuCl_3$), gadolinium chloride ($GdCl_3$), terbium chloride ($TbCl_3$), alum, tannic acid, and polyphenols (e.g., tea polyphenol).

In another embodiment, a condiment composition is provided comprising a condiment base and at least one natural and/or synthetic high-potency sweetener in combination with at least one sweet taste improving inorganic salt additive chosen from sodium chloride, potassium chloride, sodium dihydrogen phosphate, sodium sulfate, potassium citrate, europium chloride ($EuCl_3$), gadolinium chloride ($GdCl_3$), terbium chloride ($TbCl_3$), magnesium sulfate, magnesium phosphate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a condiment composition is provided comprising a condiment base and at least one natural and/or synthetic high-potency sweetener in combination with at least one sweet taste improving organic salt additive chosen from choline chloride, gluconic acid sodium salt, gluconic acid potassium salt, guanidine HCl, amiloride HCl, glucosamine HCl, monosodium glutamate (MSG), adenosine monophosphate salt, magnesium gluconate, potassium tartrate, and sodium tartrate.

In another embodiment, a condiment composition is provided comprising a condiment base and at least one natural and/or synthetic high-potency sweetener in combination with at least one sweet taste improving nucleotide additive, at least one sweet taste improving carbohydrate additive, and at least one sweet taste improving amino acid additive; wherein the at least one nucleotide additive is chosen from inosine monophosphate ("IMP"), guanosine monophosphate ("GMP"), adenosine monophosphate ("AMP") cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, omithine, methionine, carnitine, aminobutyric acid (alpha-, beta-, and gamma-isomers), glutamine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving nucleotide additive and at least one sweet taste improving carbohydrate additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, genetiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup.

In another embodiment, a condiment composition is provided comprising a condiment base and at least one natural and/or synthetic high-potency sweetener in combination with at least one sweet taste improving nucleotide additive and at least one sweet taste improving polyol additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a condiment composition is provided comprising a condiment base and at least one natural and/or synthetic high-potency sweetener in combination with at least one sweet taste improving nucleotide additive and at least one sweet taste improving amino acid; wherein the at least one nucleotide additive is chosen from inosine monophosphate ("IMP"), guanosine monophosphate ("CMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, omithine, methionine, carnitine, aminobutyric acid (alpha-, beta-, and gamma-isomers), glutarnine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving carbohydrate additive, at least one sweet taste improving polyol additive, and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, eysteine, cystine, alanine, valine, tyrosine, leucine, isoleucine, asparagine, serine, lysine, histidine, omithine, methionine, camitine, aminobutyric acid (alpha-, beta-, and gamma-isomers), glutamine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving carbohydrate additive and at least one sweet taste improving polyol additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaecharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a condiment composition is provided comprising a condiment base and at least one natural and/or synthetic high-potency sweetener in combination with at least one sweet taste improving carbohydrate additive and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaecharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, omithine, methionine, camitine, aminobutyric acid (alpha-, beta-, and gamma-isomers), glutamine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving polyol additive and at least one sweet taste improving amino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, omithine, methionine, carnitine, aminobutyric acid (alpha-, beta-, and gamma-isomers), glutamine, hydroxyproline, taurine, norvaline, sarcosine, or salts thereof.

In another embodiment, a condiment composition is provided comprising a condiment base and at least one natural and/or synthetic high-potency sweetener in combination with at least one sweet taste improving polyol additive and at least one sweet taste improving inorganic salt additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one inorganic salt additive is chosen from sodium chloride, potassium chloride, sodium dihydrogen phosphate, sodium sulfate, potassium citrate, europiumn chloride (LuCl$_3$), gadolinium chloride (GdCl$_3$), terbium chloride (TbCl$_3$), magnesium sulfate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a condiment composition is provided comprising a condiment base and at least one natural and/or synthetic high-potency sweetener in combination with at least one sweet taste improving carbohydrate additive and at least one sweet taste improving inorganic salt additive; wherein the at least one carbohydrate additive is chosen from tagatose, trehalose, galactose, rhamnose, cyclodextrin (e.g., α-cyelodextrin, β-cyclodextrin, and γ-cyclodextrin), maltodextrin (including resistant maltodextrins such as Fibersol- 2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one inorganic salt additive is chosen from sodium chloride, potassium chloride, sodium dihydrogen phosphate, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a condiment composition is provided comprising a condiment base and at least one natural and/or synthetic high-potency sweetener in combination with at least one sweet taste improving carbohydrate additive, at least one sweet taste improving amino acid additive, and at least one sweet taste improving inorganic salt additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomattose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof, and wherein the at least one inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a condiment composition is provided comprising a condiment base and at least one natural and/or synthetic high-potency sweetener in combination with at least one sweet taste improving polyol additive and at least one sweet taste improving polyamino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one polyamino acid additive is chosen from poly-L-aspartic acid, poly-L-lysine (e.g., poly-L-cα-lysine or poly-L-ϵ-lysine), poly-L-omithine (e.g., poly-L-α-omithine or poly-L-ϵ-ornithine), poly-L-arginine, and other polymeric forms of amino acids, or salts thereof.

In another embodiment, a condiment composition is provided comprising a condiment base and at least one natural and/or synthetic high-potency sweetener in combination with at least one sweet taste improving protein or protein hydrolysate additive and at least one sweet taste improving inorganic salt additive; wherein the at least one sweet taste improving protein or protein hydrolysate additive is chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, theanine, asparagine, glutamine, arginine, valine, isoleucine, leucine, norvaline, methionine, proline, tyrosine, hydroxyproline, or the like), collagen (e.g., gelatin), partially hydrolyzed collagen (e.g., hydrolyzed fish collagen), and collagen hydrolysates (e.g., porcine collagen hydrolysate); and wherein the at least one sweet taste improving inorganic salt additive is chosen from sodium chloride, potassium chloride, sodium sulfate, potassium citrate, europium chloride ($EuCl_3$), gadolinium chloride ($GdCl_3$), terbium chloride ($TbCl_3$), magnesium phosphate, magnesium sulfate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a condiment composition is provided comprising a condiment base and rebaudioside A in combination with at least one natural and/or synthetic high-potency sweetener other than rebaudioside-A and at least one sweet taste improving composition.

In another particular embodiment, a condiment composition is provided comprising a condiment base and rebaudioside A in combination with at least one synthetic high-potency sweetener, wherein the at least one synthetic high-potency sweetener functions as a sweet taste improving composition. Non-limiting examples of suitable sweet taste improving synthetic sweetener additives include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4- hydroxyphenyl)propyl]-L-α-aspartyl]-L-phenylalanine 1-methyl ester, salts thereof, and the like.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, cyclamate, saccharin, aspartame, acesulfame potassium or other salts, or neotame, in combination with at least one sweet taste improving amino acid additive and at least one sweet taste improving polyol additive is provided. In a particular embodiment, the at least one sweet taste improving amino acid additive is present in an amount from about 100 ppm to about 25,000 ppm of the composition, and the at least one sweet taste improving polyol additive is present in an amount from about 400 to about 80,000 ppm of the composition. In a still more particular embodiment, the at least one sweet taste improving amino acid additive is glycine or alanine, and the at least one sweet taste improving polyol additive is erythritol.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving protein or protein hydrolysate additive is provided. In a particular embodiment, the at least one sweet taste improving amino acid additive is present in an amount from about 100 to about 25,000 ppm of the composition, and the at least one sweet taste improving protein or protein hydrolysate additive is present in an amount from about 200 ppm to about 50,000 ppm of the composition. In a still more particular embodiment, the at least one sweet taste improving amino acid additive is glycine or lysine, and the at least one sweet taste improving protein or protein hydrolysate additive is a protein, a hydrolysate, or a reaction product of a hydrolysate of a protein containing glycine, alanine, serine, leucine, valine, isoleucine, proline, or threonine.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving protein or protein hydrolysate additive and at least one sweet taste improving polyol additive is provided. In a particular embodiment, the at least one sweet taste improving protein or protein hydrolysate additive is present in an amount from about 200 ppm to about 50,000 ppm of the composition, and at least one sweet taste improving polyol additive is present in an amount from about 400 to about 80,000 ppm of the composition. In a still more particular embodiment, the at least one sweet taste improving protein or protein hydrolysate additive is a protein, a hydrolysate, or a reaction product of a hydrolysate of proteins containing glycine, alanine, serine, leucine, valine, isoleucine, proline, or threonine, and the at least one sweet taste improving polyol additive is erythritol.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving carbohydrate additive is provided. In a particular embodiment, the at least one sweet taste improving carbohydrate additive is present in an amount from about 1,000 to about 100,000 ppm of the composition. In a still more particular embodiment, the sweetener composition comprises REBA and glucose, sucrose, HFCS, or D-fructose in an amount from about 10,000 ppm to about 80,000 ppm of the composition.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polyol additive is provided. In a particular embodiment, the at least one sweet taste improving polyol additive is present in an amount from about 400 to about 80,000 ppm of the composition. In another particular embodiment, the at least one sweet taste improving polyol additive is present in an amount from about 5,000 to about 60,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with propylene glycol, erythritol, or combinations thereof.

In one embodiment, a condiment composition comprising a condiment base and a sweetener composition comprising rebaudioside-A (REBA) (with at least 50% REBA in a steviol glycoside mixture) in combination with at least one sweet taste improving polyol additive is provided. Desirably, the at least one sweet taste improving polyol additive comprises erythritol. In a particular embodiment of the sweetener composition, rebaudioside A is present in an amount from about 100 to about 3,000 ppm and the erythritol is present in an amount from about 400 to about 80,000 ppm of the total sweetener composition. In another embodiment of the sweetener composition, rebaudioside A is present in an amount from about 100 to about 3,000 ppm and the erythritol is present in an amount from about 5,000 to about 40,000 ppm of the total sweetener composition. In still another embodiment of the sweetener composition, rebaudioside A is present in an amount from about 100 to about 3,000 ppm and the erythritol is present in an amount from about 10,000 to about 35,000 ppm of the total sweetener composition. In another particular embodiment of the sweetener composition, rebaudioside A and erythritol are present in the sweetener composition in a ratio from about 1:4 to about 1:800, respectively. In yet another particular embodiment of the sweetener composition, rebaudioside A and erythritol are present in the sweetener composition in a ratio from about 1:20 to about 1:600, respectively; more particularly from about 1:50 to about 1:300; and still more particularly from about 1:75 to about 1:150.

In another embodiment, a condiment composition comprising a condiment base and a sweetener composition comprising rebaudioside-A (REBA), stevia, stevioside, mogroside IV, mogroside V, Luo Han Guo sweetener, monatin, or curculin, in combination with at least one sweet taste improving synthetic sweetener additive is provided. In a particular embodiment, the condiment composition comprises a condiment base and a sweetener comprising rebaudioside-A (REBA) in combination with saccharin or acesulfame potassium or other salts in an amount from about 10 ppm to about 100 ppm of the composition.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving carbohydrate additive and at least one sweet taste improving polyol additive is provided. In a particular embodiment, the at least one sweet taste improving carbohydrate additive is present in an amount from about 1,000 to about 100,000 ppm of the composition and at least one sweet taste improving polyol additive is present in an amount from about 400 to about 80,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with tagatose, fructose or sucrose and erythritol.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving inorganic salt additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with NaCl, KCl, $NaHSO_4 \cdot H_2O$, $NaH_2PO_4$, $MgSO_4$, $KAl(SO_4)_2$ (alum), magnesium phosphate, magnesium chloride, KCl and $KH_2PO_4$, or other combinations thereof. A particularly desirable embodiment comprises the a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with a mixture of inorganic salt additives, such as chlorides, phosphates, and sulfates of sodium, magnesium, potassium, and calcium (e.g., sodium chloride and potassium chloride; potassium phosphate and potassium chloride; sodium chloride and sodium phosphate; calcium phosphate and calcium sulfate; magnesium chloride and magnesium phosphate; and calcium phosphate, calcium sulfate, and potassium sulfate).

In a particular embodiment, a condiment composition comprising a condiment base and a sweetener composition comprises aspartame, acesfulame potassium or other salts, and sucralose in combination with at least one sweet taste improving inorganic salt additive. In a particular embodiment, the at least one sweet taste improving inorganic salt additive is present in an amount in the range of about 25 to about 5,000 ppm of the composition. Non-limiting examples include a condiment base and a sweetener composition comprising aspartame, acesulfame potassium, and sucralose in combination with magnesium chloride; a condiment base and a sweetener composition comprising aspartame, acesulfame potassium, and sucralose in combination with magnesium sulfate; or a condiment base and a sweetener composition comprising aspartame, acesulfame potassium, and sucralose in combination with magnesium sulfate and sodium chloride.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving organic acid salt additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with choline chloride in citrate buffer, D-gluconic acid sodium salt, guanidine HCl, D-glucosamine HCl, amiloride HCl, or combinations thereof.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving organic acid additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fumaric acid, malic acid, tartaric acid, citric acid, adipic acid, ascorbic acid, tannic acid, succinic acid, glutaric acid, or combinations thereof.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive is provided. In a particular embodiment, the at least one sweet taste improving amino acid additive is present in an amount from about 100 to about 25,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine, L-alanine, L-serine, L-threonine, β-alanine, aminobutyric acid (alpha-, beta-, or gamma-isomers), L-aspartic acid, L-glutamic acid, L-lysine, glycine and L-alanine mixture, salt derivatives or combinations thereof.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving surfactant additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with dioctyl sulfosuccinate sodium, cetylpyridinium chloride, hexadecyltrimethylammonium bromide, sucrose oleate, polysorbate 20, polysorbate 80, lecithin, or combinations thereof.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polymer additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with cationic polymer such as polyethyleneimine, poly-L-lysine (e.g., poly-L-α-lysine or poly-L-ε-lysine), poly-L-ornithine (e.g., poly-L-α-ornithine or poly-L-ε-ornithine), chitosan, or combinations thereof.

In one embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polymer additive and at least one sweet taste improving polyol additive is provided. In a particular embodiment, the at least one sweet taste improving polymer additive is present in an amount from about 30 to about 2,000 ppm of the composition, and the at least one sweet taste improving polyol additive is present in an amount from about 400 to about 80,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with a hydrocolloid, such as a gum acacia seyal, and erythritol.

In one embodiment, a condiment composition comprising a condiment base and a sweetener composition comprising rebaudioside-A (EBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving protein or protein hydrolysate additive is provided. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with bovine serua albumin (BSA), whey protein or combinations thereof.

In one embodiment, a condiment composition comprising a condiment base and a sweetener composition comprising rebaudioside-A (EBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving inorganic acid salt additive is provided. In a particular embodiment, the at least one sweet taste improving amino acid additive is present in an amount from about 100 to about 25,000 ppm of the composition and the at least one sweet taste improving inorganic acid salt additive is present in an amount from about 25 to about 5,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and alum; a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and potassium chloride; a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and sodium chloride; a condiment base and a sweetener composition comprising REBA in combination with glycine, potassium dihydrogen phosphate, and potassium chloride; and rebaudioside-A (REBA), stevia, stevioside, morgroside IV, morgroside V, Lo Han Guo, monatin, curculin, sucralose, saccharin, aspartame, acesulfame potassium or other salts, or neotame, in combination with glycine, sodium chloride, and potassium chloride.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving carbohydrate additive and at least one sweet taste improving inorganic acid salt additive is provided. In a particular embodiment, the at least one sweet taste improving carbohydrate additive is present in an amount from about 1,000 to about 100,000 ppm of the composition and the at least one sweet taste improving inorganic acid salt additive is present in an amount from about 25 ppm to about 5,000 ppm. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose and alum; a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose and potassium chloride; a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose and sodium chloride; a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose, potassium phosphate, and potassium chloride; and a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose, sodium chloride, and potassium chloride.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving bitter additive and at least one sweet taste improving inorganic salt additive is provided. A non-limiting example include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with urea and sodium chloride.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving polyamino acid additive is provided. In a particular embodiment, the at least one sweet taste improving amino acid additive is present in an amount from about 100 to about 25,000 ppm of the composition and the at least one sweet taste improving polyamino acid additive is present in an amount from about 30 to about 2,000 ppm of the composition. Non-limiting examples include a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and poly-L-α-lysine; and a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and poly-L-ε-lysine.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving organic acid additive is provided. In a particular embodiment, the at least one sweet taste improving amino acid additive is present in an amount from about 100 to about 25,000 ppm of the composition and the at least one sweet taste improving organic acid additive is present in an amount from about 10 to about 5,000 ppm of the composition. A non-limiting example includes a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and sodium gluconate.

In another embodiment, a condiment composition comprising a condiment base and a sweetener composition comprising rebaudioside-A (REBA), stevia, stevioside, mogroside IV mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving carbohydrate additive is provided. In a particular embodiment, the at least one sweet taste improving amino acid additive is present in an amount from about 100 to about 25,000 ppm of the composition and the at least one sweet taste improving carbohydrate additive is present in an amount from about 1,000 to about 100,000 ppm of the composition. A non-limiting example includes a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with L-alanine and fructose.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive, at least one sweet taste improving polyol additive, at least one sweet taste improving inorganic salt additive, and at least one sweet taste improving organic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, the at least one sweet taste improving inorganic salt additive is present in an amount from about 25 to about 5,000 ppm of the composition, and the at least one sweet taste improving organic acid salt additive is present in an amount from about 20 to about 10,000 ppm of the composition. A non-limiting example includes a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with erythritol, glycine, KCl, KH$_2$PO$_4$, and choline chloride.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive, at least one sweet taste improving carbohydrate additive, and at least one sweet taste improving polyol additive is provided. In a particular embodiment, the at least one sweet taste improving amino acid additive is present in an amount from about 100 to about 25,000 ppm of the composition, the at least one sweet taste improving carbohydrate additive is present in an amount from about 1,000 to about 100,000 ppm of the composition, and the at least one sweet taste improving polyol additive is present in an amount from about 400 to about 80,000 ppm of the composition. A non-limiting example includes a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with L-alanine, fructose, and erythritol.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive, at least one sweet taste improving polyol additive, and at least one sweet taste improving inorganic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, and the at least one sweet taste improving inorganic acid salt additive is present in an amount from about 25 to about 5,000 ppm of the composition. A non-limiting example includes a condiment base and a sweetener composition comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with erythritol, glycine, KCl, and $KH_2PO_4$.

In another embodiment, a condiment composition comprising a condiment base and a sweetener composition comprising rebaudioside-A (REBA), stevia, stevioside, mogroside IV, mogroside V, Luo Han Guo sweetener, monatin, curculin, glycyrrihizin such as mono-ammonium glycyrhizic acid salt hydrate, sucralose, saccharin, cyclamate, aspartame, acesulfame potassium or other salts, or neotame, in combination with a sweet taste improving inorganic acid salt additive is provided. A non-limiting example includes a condiment base and a sweetener composition comprising rebaudioside-A (REBA), stevia, stevioside, mogroside TV, mogroside V, Luo Han Guo sweetener, monatin, curculin, glycyrrihizin such as mono-ammonium glycyrrhizic acid salt hydrate, sucralose, saccharin, cyclamate, aspartame, acesulfame potassium or other salts, or neotame, in combination with sodium chloride.

The desired weight ratio of the natural and/or synthetic high-potency sweetener to sweet taste improving composition(s) in the sweetener composition will depend on the particular natural and/or synthetic high-potency sweetener, and the sweetness and other characteristics desired in the final product. Natural and/or synthetic high-potency sweeteners vary greatly in their potency, ranging from about 30 times more potent than sucrose to about 8,000 times more potent-than sucrose on a weight basis. In general, the weight ratio of the natural and/or synthetic high-potency sweetener to sweet taste improving composition may for example range from range between 10,000:1 and 1:10,000; a further non-limiting example may range from about 9,000:1 to about 1:9,000; yet another example may range from about 8,000:1 to about 1:8,000; a further example may range from about 7,000:1 to about 1:7,000; another example may range from about 6,000:1 to about 1:6000; in yet another example may range from about 5,000:1 to about 1:5,000; in yet another example may range from about 4,000:1 to about 1:4,000; in yet another example may range from about 3,000:1 to about 1:3,000; in yet another example may range from about 2,000:1 to about 1:2,000; in yet another example may range from about 1,500:1 to about 1:1,500; in yet another example may range from about 1,000:1 to about 1:1,000; in yet another example may range from about 900:1 to about 1:900; in yet another example may range from about 800:1 to about 1:800; in yet another example may range from about 700:1 to about 1:700; in yet another example may range from about 600:1 to about 1:600; in yet another example may range from about 500:1 to about 1:500; in yet another example may range from about 400:1 to about 1:400; in yet another example may range from about 300:1 to about 1:300; in yet another example may range from about 200:1 to about 1:200; in yet another example may range from about 150:1 to about 1:150; in yet another example may range from about 100:1 to about 1:100; in yet another example may range from about 90:1 to about 1:90; in yet another example may range from about 80:1 to about 1:80; in yet another example may range from about 70:1 to about 1:70; in yet another example may range from about 60:1 to about 1:60; in yet another example may range from about 50:1 to about 1:50; in yet another example may range from about 40:1 to about 1:40; in yet another example may range from about 30:1 to about 1:30; in yet another example may range from about 20:1 to about 1:20; in yet another example may range from about 15:1 to about 1:15; in yet another example may range from about 10:1 to about 1:10; in yet another example may range from about 9:1 to about 1:9; in yet another example may range from about 8:1 to about 1:8; in yet another example may range from about 7:1 to about 1:7; in yet another example may range from about 6:1 to about 1:6; in yet another example may range from about 5:1 to about 1:5; in yet another example may range from about 4:1 to about 1:4; in yet another example may range from about 3:1 to about 1:3; in yet another example may range from about 2:1 to about 1:2; and in yet another example may be about 1:1; depending on the particular natural and/or synthetic high-potency sweetener selected.

It is contemplated that the combination of at least one natural and/or synthetic high-potency sweetener to at least one sweet taste improving composition may be carried out in any pH range that does not materially or adversely affect the taste of the sweetener composition. A non-limiting example of the pH range may be from about 2 to about 8. A further example includes a pH range from about 2 to about 5.

One of ordinary skill in the art may combine at least one natural and/or synthetic high-potency sweetener, at least one sweet taste improving composition, and sweetenble composition in any manner. For example, at least one natural and/or synthetic high-potency sweetener may be added to the sweetenble composition before the at least one sweet taste improving composition. In another example, at least one natural and/or synthetic high-potency sweetener may be added to the sweetenble composition after the at least one sweet taste improving composition. In yet another example, at least one natural and/or synthetic high-potency sweetener may be added to the sweetenble composition simultaneously with the at least one sweet taste improving composition.

In yet another embodiment, at least one natural and/or synthetic high-potency sweetener may be combined with the at least one sweet taste improving composition prior to being added to a sweetenble composition. For example, the at least one natural and/or synthetic high-potency sweetener may be in a pure, diluted, or concentrated form as a liquid (e.g., solution), solid (e.g., powder, chunk, pellet, grain, block, crystalline, or the like), suspension, gas state, or combinations thereof may be contacted with the at least one sweet taste improving composition which may be in a pure, diluted, or concentrated form as a liquid (e.g., solution), solid (e.g., powder, chunk, pellet, grain, block, crystalline, or the like), suspension, gas state, or combinations thereof before both are contacted with a sweetenble composition. In yet another embodiment, when there are more than one natural and/or synthetic high-potency sweeteners or more than one sweet taste improving composition in the sweeteneable composition, each component of the sweetenable composition may be added simultaneously, in an alternating pattern, in a random pattern, or any other pattern.

Generally, the amount of natural and/or synthetic high-potency sweetener present in a sweetened composition varies widely depending on the desired sweetness. Those of ordinary skill in the art can readily discern the appropriate amount of sweetener to put in the sweetened composition. In a particular embodiment, the at least one natural and/or synthetic high-potency sweetener is present in the sweetened composition in an amount in the range of about 1 to about 5,000 ppm of the sweetened composition and the at least one sweet taste improving composition is present in the sweetened composition in an amount in the range of about 0.1 to about 100,000 ppm of the sweetened composition.

In accordance with particular embodiments, suitable amounts of natural high-potency sweeteners for sweetened compositions comprise amounts in the range from about 100 ppm to about 3,000 ppm for rebaudioside A; from about 50 ppm to about 3,000 ppm for stevia; from about 50 ppm to about 3,000 ppm for stevioside; from about 50 ppm to about 3,000 ppm for mogroside IV; from about 50 ppm to about 3,000 ppm for mogroside V; from about 50 ppm to about 3,000 ppm for Luo Han Guo sweetener; from about 5 ppm to about 300 ppm for monatin, from about 5 ppm to about 200 ppm for thaumatin; and from about 50 ppm to about 3,000 ppm for mono-ammonium glycyrrhizic acid salt hydrate.

In accordance with particular embodiments, suitable amounts of synthetic high-potency sweeteners for sweetened compositions comprise a range from about 1 ppm to about 60 ppm for alitame; from about 10 ppm to about 600 ppm for aspartame; from about 1 ppm to about 20 ppm for neotame; from about 10 ppm to about 500 ppm for acesulfame potassium; from about 50 ppm to about 5,000 ppm for cyclamate; from about 10 ppm to about 500 ppm for saccharin; from about 5 ppm to about 250 ppm for sucralose; from about 1 ppm to about 20 ppm for N—[N-[3-(3-hydroxy-4-methoxyphenyl)propyl]-L-α-aspartyll]-L-phenylalanine 1-methyl ester; from about 1 ppm to about 20 ppm for N—[N-[3-(3-hydroxy-4-methoxyphenyl)-3-methylbutyl]-L-α-aspartyl]-L-phenylalanine 1-methyl ester; and from about 1 ppm to about 20 ppm for N—[N-[3-(3-methoxy-4-hydroxyphenyl)propyl]-L-α-aspartyl]-L-phenylalanine 1-methyl ester.

The condiment compositions provided herein may be made using any suitable methods known to those of ordinary skill in the art.

V. Examples

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, %'s are by weight.

Example Set A

The following non-limiting examples provide recipes for several exemplary embodiments of low calorie condiments provided herein. In each example, 1 tsp of the combination of rebaudioside A and erythritol is equivalent to 1 tsp of sugar.

Example A1

Mustard

A condiment base comprising ground mustard seed, adjuvants (e.g., water and/or vinegar), and spices (e.g., tumeric) is combined with a rebaudioside A sweetener composition comprising rebaudioside A and erythritol.

Example A2

Ketchup

A condiment base comprising tomatoes or a tomato product (e.g., tomato paste), adjuvants (e.g., water), and spices (e.g., salt, onions, and garlic), is combined with a rebaudioside A sweetener composition comprising rebaudioside A and erythritol.

Example A3

Mayonnaise

A condiment base comprising a natural or lightly hydrogenated vegetable oil (e.g., corn, soybean, sunflower seed, cotton-seed, grapeseed, sesame, or rapeseed) combined with egg yolks and flavored with salt, mustard, vinegar, and citrus juice is combined with a rebaudioside A sweetener composition comprising rebaudioside A and erythritol.

Example A4

Oil and Vinegar Salad Dressing

A condiment base comprising ½ cup water, ½ cup vegetable oil, ¼ cup vinegar, ½ tsp salt, and ½ tsp pepper is combined with 1 tsp of a rebaudioside A sweetener composition comprising rebaudioside A and erythritol.

Example A5

Caesar Salad Dressing

A condiment base comprising 1 egg, raw, 3 Tbsp lemon juice, 1 large clove garlic, 1 cup olive oil, ¼ to ½ cup grated Parmesan or Romano cheese, 4 Tbsp anchovy paste, and ¼ tsp salt and pepper to taste is combined with 1 tsp of a rebaudioside A sweetener composition comprising rebaudioside A and erythritol.

Example A6

French Salad Dressing

A condiment base comprising ½ cup vegetable oil, ¼ cup water, 3 Tbsp vinegar, ½ tsp salt, ½ tsp whey, ⅓ tsp modified food starch, and a pinch of paprika is combined with ⅓ cup of a rebaudioside A sweetener composition comprising rebaudioside A and erythritol.

Example A7

Ranch Salad Dressing

A condiment base comprising ½ cup water, ½ cup vegetable oil, 3 Tbsp vinegar, 1 egg yolk, 2 Tbsp buttermilk, ½ tsp salt, ½ tsp whey, ½ tsp modified food starch, and ¼ teaspoon maltodextrin is combined with 3 Tbsp of a rebaudioside A sweetener composition comprising rebaudioside A and erythritol.

Example A8

Bleu Cheese Salad Dressing

A condiment base comprising ½ cup vegetable oil, ¼ cup vinegar, ¼ cup water, 3 Tbsp blue cheese, 1 egg yolk, and 1 tsp lactic acid is combined with 2 Tbsp or a rebaudioside A sweetener composition comprising rebaudioside A and erythritol.

The following Examples B1-B3, C1-C3, D, E1-E3, and F illustrate methods of making purified rebaudioside A in accordance with particular embodiments of this invention:

Example Set B

TABLE 2

Summary of Examples B1-3

|    | Crude Rebaudioside A (g) | Ethanol (95%)(mL) | Solvent Methanol (99%)(mL) | Water (mL) | Heating T (° C.) | Drying T (° C.) | Yield (g) | HPLC Purity (wt/wt %) |
|----|--------------------------|-------------------|----------------------------|------------|------------------|-----------------|-----------|-----------------------|
| B1 | 400                      | 1200              | 400                        | 320        | 50               | 50              | 130       | 98.9                  |
| B2 | 100                      | 320               | 120                        | 50         | 30-40            | 60              | 72        | 98.3                  |
| B3 | 50                       | 160               | 60                         | 25         | ~30              | 60              | 27.3      | 98.2                  |

Example B1

Crude rebaudioside A (77.4% purity) mixture was obtained from a commercial source. The impurities (6.2% stevioside, 5.6% rebaudioside C, 0.6% rebaudioside F, 1.0% other steviolglycosides, 3.0% rebaudioside D, 4.9% rebaudioside B, 0.3% steviolbioside) were identified and quantified using HPLC on dry basis, moisture content 4.7%.

Crude rebaudioside A (400 g), ethanol (95%, 1200 mL), methanol (99%, 400 mL) and water (320 mL) were combined and heated to 50° C. for 10 minutes. The clear solution was cooled to 22° C. for 16 hours. The white crystals were filtered and washed twice with ethanol (2×200 mL, 95%) and dried in a vacuum oven at 50° C. for 16-24 hours der reduced pressure (20 mm).

The final composition of substantially pure rebaudioside A (130 g) comprised 98.91% rebaudioside A, 0.06% stevioside, 0.03% rebaudioside C, 0.12% rebaudioside F, 0.13% other steviolglycosides, 0.1% rebaudioside D, 0.49% rebaudioside B and 0.03% steviolbioside, all by weight.

Example B2

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (100 g), ethanol (95%, 320 mL), methanol (99%, 120 mL) and water (50 mL) were combined and heated to 30-40° C. for 10 minutes. The clear solution was cooled to 22° C. for 16 hours. The white crystals were filtered and washed twice with ethanol (2×50 mL, 95%). The wet filter cake (88 g) was slurried in ethanol (95%, 1320 mL) for 16 hours, filtered, washed with ethanol (95%, 2 x 100 mL) and dried in a vacuum oven at 60° C. for 16-24 hours under reduced pressure (20 mm).

The final composition of substantially pure rebaudioside A (72 g) comprised 98.29% rebaudioside A, 0.03% stevioside, 0.02% rebaudioside C, 0.17% rebaudioside F, 0.06% rebaudioside D and 1.09% rebaudioside B. Steviolbioside was not detected by HPLC.

Example B3

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (50 g), ethanol (95%, 160 mL), methanol (99%, 60 mL) and water (25 mL) were combined and heated to approximately 30° C. for 10 minutes. The clear solution was cooled to 22° C. for 16 hours. The white crystals were filtered and washed twice with ethanol (2×25 mL, 95% ). The wet filter cake (40 g) was slurried in methanol (99%, 600 mL) for 16 hours, filtered, washed with methanol (99%, 2×25 mL) and dried in a vacuum oven at 60° C. for 16-24 hours under reduced pressure (20 mm).

The final composition of substantially pure rebaudioside A (27.3g) comprised 98.22% rebaudioside A, 0.04% stevioside, 0.04% rebaudioside C, 0.18% rebaudioside F, 0.08% rebaudioside D and 1.03% rebaudioside B. Steviolbioside was not detected by HPLC.

Example Set C

TABLE 3

Summary of Examples C1-3

|    | Crude Rebaudioside A (g) | Solvent             |                         |            | Wash Solvent           | Yield (g) | HPLC Purity (%) |
|----|--------------------------|---------------------|-------------------------|------------|------------------------|-----------|-----------------|
|    |                          | Ethanol (95%)(mL)   | Organic Co-solvent (mL) | Water (mL) |                        |           |                 |
| C1 | 5                        | 15                  | Methanol (6)            | 3.5        | EtOH/MeOH (3:1 v/v)    | 2.6       | >99             |
| C2 | 5                        | 15                  | Methanol (5)            | 4          | EtOH/MeOH (3:1 v/v)    | 2.3       | >99             |
| C3 | 5                        | 16                  | Methanol (6)            | 2.5        | *EtOH/MeOH (8:3 v/v)   | 3.2       | >98             |

Example C1

A mixture of crude rebaudioside A (80.37% purity, 5 g), ethanol (95%, 15 mL), methanol (5 mL) and water (3.5 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to get 2.6 g of purified product (>99% by HPLC).

Example C2

A mixture of crude rebaudioside A (80.37% purity, 5 g), ethanol (95%, 15 mL), methanol (5 mL) and water (4.0 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to get 2.3 g of purified product (>99% by HPLC).

Example C3

A mixture of crude rebaudioside A (80.37% purity, 5 g), ethanol (95%, 16 mL), methanol (6 mL) and water (2.5 mL) were combined and heated to reflux for 10 minutes. The clear solution was cooled to 22° C. for 2 hours. During this time crystals starts to appear. The mixture is stirred at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to get 3.2 g of purified product (>98% by HPLC).

Example D

TABLE 4

Summary of Example D

| | | Solvent | | | | |
|---|---|---|---|---|---|---|
| | Crude Rebaudioside A (g) | Organic Solvent (mL) | Water (mL) | Wash Solvent | Yield (g) | HPLC Purity (%) |
| D | 50 | EtOH (160) | 40 | EtOH | 19.8 | 99.5 |

A mixture of crude rebaudioside A (80.37% purity, 50 g), ethanol (95%, 160 mL) and water (40 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to get 19.8 g of purified product (99.5% by HPLC).

Example E

Example E1

A mixture of crude rebaudioside A (41% purity, 50 g), ethanol (95%, 160 mL), methanol (99.8%, 60 mL) and water (25 mL) were combined by stirring at 22° C. A white product crystallized out in 5-20 hours. The mixture was stirred for additional 48 hours. The white crystalline product was filtered and washed twice with ethanol (95%, 25 mL). The wet cake of white crystalline product then was slurried in methanol (99.8%, 200 mL) for 16 hours, filtered, washed twice with methanol (99.8%, 25 mL), and dried in a vacuum oven at 60° C. for 16-24 hours under reduced pressure (20 mm) to give 12.7 g of purified product (>97% by HPLC).

Example E2

A mixture of crude rebaudioside A (48% purity, 50 g), ethanol (95%, 160 mL), methanol (99.8%, 60 mL) and water (25 mL) was combined by stirring at 22° C. The white product crystallized out in 3-6 hours. The mixture was stirred for additional 48 hours. The white crystalline product was filtered and washed twice with ethanol (95%, 25 mL). The wet cake of white crystalline product then was slurried in methanol (99.8%, 300 mL) for 16 hours, filtered, washed twice with methanol (99.8%, 25 mL) and dried in a vacuum oven at 60° C. for 16-24 hours under reduced pressure (20 mm) to give 18.6 g of purified product (>97% by HPLC).

Example E3

A mixture of crude rebaudioside A (55% purity, 50 g), ethanol (95%, 160 mL), methanol (99.8%, 60 mL) and water (25 mL) was combined by stirring at 22° C. The white product crystallized out in 15-30 minutes. The mixture was stirred for an additional 48 hours. The white crystalline product was filtered and washed twice with ethanol (95%, 25 mL). The wet cake of white crystalline product was slurried in methanol (99.8%, 350 mL) for 16 hours, filtered, washed twice with methanol (99.8%, 25 mL) and dried in a vacuum oven at 60° C. for 16-24 hours under reduced pressure (20 mm) to give 22.2 g of purified product (>97% by HPLC).

Example F

A solution of rebaudioside A (>97% pure by HPLC) was prepared in double distilled water (12.5 gm in 50 mL, 25% concentration) by stirring the mixture at 40° C. for 5 minutes. An amorphous form of rebaudioside A was formed by immediately using the clear solution for spray drying with the Lab-Plant spray drier SD-04 instrument (Lab-Plant Ltd., West Yorkshire, U.K.). The solution was fed through the feed pump into the nozzle atomizer which atomized it into a spray of droplets with the help of a constant flow of nitrogen/air.

TABLE 5

Summary of Examples E1-3

| | Crude Rebaudioside A (g) | Ethanol (95%)(mL) | Organic Co-solvent (mL) | Water (mL) | Methanol Slurry (mL) | Yield (g) | HPLC Purity (%) |
|---|---|---|---|---|---|---|---|
| E1 | 50 | 160 | Methanol (60) | 25 | 200 | 12.7 | >97 |
| E2 | 50 | 160 | Methanol (60) | 25 | 300 | 18.6 | >97 |
| E3 | 50 | 160 | Methanol (60) | 25 | 350 | 22.2 | >97 |

Moisture was evaporated from the droplets under controlled temperature conditions (about 90 to about 97° C.) and airflow conditions in the drying chamber and resulted in the formation of dry particles. This dry powder (11-12 g, $H_2O$ 6.74%) was discharged continuously from the drying chamber and was collected in a bottle. The solubility in water at room temperature was determined to be >35.0%.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A condiment composition comprising a condiment base, rebaudioside A and erythritol, wherein:
   the rebaudioside A has a purity greater than about 97% by weight on a dry basis;
   the weight ratio of rebaudioside A to erythritol is about 1:75 to about 1:150, and
   the condiment base is selected from the group consisting of ketchup, mustard, mayonnaise, barbecue sauce, chili sauce, chutney, cocktail sauce, curry, dip, fish sauce, horseradish, hot sauce, jelly, jam, marmalade, preserve, peanut butter, relish, remoulade, salad dressing, salsa, sauerkraut, soy sauce, steak sauce, syrup, tartar sauce, Worcestershire sauce or combinations thereof.

2. The condiment composition of claim 1, wherein the rebaudioside A is present in an amount from about 100 ppm to about 3,000 ppm.

3. The condiment composition of claim 1, further comprising at least one steviolglycoside selected from the group consisting of rebaudioside B, rebaudioside C, rebaudioside E, rebaudioside F, dulcoside A, dulcoside B, stevioside, steviolbioside and combinations thereof.

4. The condiment composition of claim 1, wherein the rebaudioside A is substantially free of steviolbioside as measured by HPLC.

5. The condiment composition of claim 1, wherein the rebaudioside A has a rate of dissolution greater than about 30%/5 minutes in water at 25° C.

6. The condiment composition of claim 1, further comprising at least one sweet taste improving composition selected from the group consisting of carbohydrates, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins, protein hydrolysates, surfactants, emulsifiers, flavonoids, alcohols, synthetic sweeteners or combinations thereof.

* * * * *